United States Patent
Van Der Horst et al.

(10) Patent No.: US 8,455,623 B2
(45) Date of Patent: Jun. 4, 2013

(54) COMPOSITIONS AND METHODS FOR DIAGNOSING AND TREATING CANCER

(75) Inventors: Edward Thein Htun Van Der Horst, Palo Alto, CA (US); Aaron Ken Sato, Burlingame, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 12/993,656

(22) PCT Filed: May 21, 2009

(86) PCT No.: PCT/US2009/003136
§ 371 (c)(1),
(2), (4) Date: Feb. 22, 2011

(87) PCT Pub. No.: WO2009/142738
PCT Pub. Date: Nov. 26, 2009

(65) Prior Publication Data
US 2011/0142840 A1      Jun. 16, 2011

Related U.S. Application Data

(60) Provisional application No. 61/055,088, filed on May 21, 2008, provisional application No. 61/091,265, filed on Aug. 22, 2008, provisional application No. 61/161,275, filed on Mar. 18, 2009.

(51) Int. Cl.
*C07K 16/00* (2006.01)
*A61K 39/395* (2006.01)

(52) U.S. Cl.
USPC .................. 530/387.1; 530/388.1; 424/130.1; 424/138.1

(58) Field of Classification Search
None
See application file for complete search history.

(56) References Cited

U.S. PATENT DOCUMENTS

| | | | |
|---|---|---|---|
| 5,233,960 | A | 8/1993 | Kato |
| 5,686,292 | A | 11/1997 | Schwall et al. |
| 6,004,528 | A | 12/1999 | Bergstein |
| 6,134,104 | A | 10/2000 | Mohi et al. |
| 6,214,344 | B1 | 4/2001 | Schwall et al. |
| 6,468,529 | B1 | 10/2002 | Schwall et al. |
| 2003/0157107 | A1 | 8/2003 | Miyawaki et al. |
| 2005/0014934 | A1 | 1/2005 | Hinton et al. |
| 2005/0233960 | A1* | 10/2005 | Kong-Beltran et al. ........ 514/12 |
| 2006/0115486 | A1 | 6/2006 | Pier et al. |
| 2007/0092520 | A1 | 4/2007 | Dennis et al. |
| 2009/0041783 | A1 | 2/2009 | Takayama et al. |

FOREIGN PATENT DOCUMENTS

| WO | WO 2006/117910 A1 | 11/2006 |
|---|---|---|
| WO | WO 2006/122797 A2 | 11/2006 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Al-Hajj, M., et al., "Prospective identification of tumorigenic breast cancer cells," *Proc. Natl. Acad. Sci. U S A* 100(7):3983-8, National Academy of Sciences, United States (2003).
Aubele, M. and Werner, M., "Heterogeneity in breast cancer and the problem of relevance of findings," *Anal. Cell. Pathol.* 19(2):53-8, Elsevier Science, Netherlands (1999).
Beachy, P.A., et al., "Tissue repair and stem cell renewal in carcinogenesis," *Nature* 432(7015):324-31, Nature Publishing Group, England (2004).
Beerman, H., et al., "Flow cytometric analysis of DNA stemline heterogeneity in primary and metastatic breast cancer," *Cytometry* 12(2):147-54, Wiley-Liss, United States (1991).
Bladt, F., et al., "Essential role for the c-met receptor in the migration of myogenic precursor cells into the limb bud," *Nature* 376(6543):768-71, Nature Publishing Group, England (1995).
Boix, L., et al., "c-met mRNA overexpression in human hepatocellular carcinoma," *Hepatology* 19(1):88-91, Williams & Wilkins, United States (1994).
Bonnet, D. and Dick, J., "Human acute myeloid leukemia is organized as a hierarchy that originates from a primitive hematopoietic cell," *Nat. Med.* 3(7):730-7, Nature Publishing Company, United States (1997).
Bonsing, B.A., et al., "High levels of DNA index heterogeneity in advanced breast carcinomas. Evidence for DNA ploidy differences between lymphatic and hematogenous metastases," *Cancer* 71(2):382-91, Wiley, United States (1993).
Bonsing, B.A., et al., "Allelotype analysis of flow-sorted breast cancer cells demonstrates genetically related diploid and aneuploid subpopulations in primary tumors and lymph node metastases," *Genes Chromosomes Cancer* 28(2):173-83, Wiley-Liss, United States (2000).
Buchholz, M., et al., "SERPINE2 (protease nexin I) promotes extracellular matrix production and local invasion of pancreatic tumors in vivo," *Cancer Res.* 63(16):4945-51, American Association for Cancer Research, United States (2003).
Bussolino, F., et al., "Hepatocyte growth factor is a potent angiogenic factor which stimulates endothelial cell motility and growth," *J. Cell. Biol.* 119(3):629-41, Rockefeller University Press, United States (1992).
Cooper, C.S., et al., "Characterization of human transforming genes from chemically transformed, teratocarcinoma, and pancreatic carcinoma cell lines," *Cancer Res.* 44(1):1-10, American Association for Cancer Research, United States (1984).
Corso, S., et al., "Silencing the MET oncogene leads to regression of experimental tumors and metastases," *Oncogene* 27(5):684-93, Nature Publishing Group, England (2008).

(Continued)

*Primary Examiner* — Hong Sang
(74) *Attorney, Agent, or Firm* — Sterne, Kessler, Goldstein & Fox P.L.L.C.

(57) ABSTRACT

Isolated antibodies that specifically bind the human MET Receptor and inhibit MET signaling are described. Also described are methods of treating cancer, the methods comprising administering a therapeutically effective amount of the provided MET antibodies and combinations thereof.

20 Claims, 30 Drawing Sheets

OTHER PUBLICATIONS

Figure 1A:
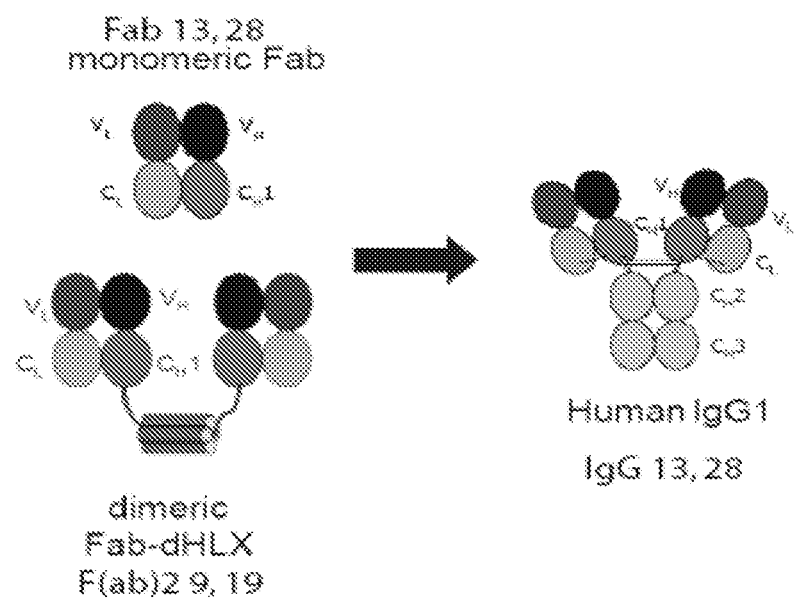

Danilkovitch-Miagkova, A. and Zbar, B., "Dysregulation of Met receptor tyrosine kinase activity in invasive tumors," *J. Clin. Invest.* 109(7):863-7, American Society for Clinical Investigation, United States (2002).

Di Renzo, M.F., et al., "Overexpression and amplification of the met/HGF receptor gene during the progression of colorectal cancer," *Clin. Cancer Res.* 1(2):147-54, The Association, United States (1995).

Furge, K.A., et al., "Met receptor tyrosine kinase: enhanced signaling through adapter proteins," *Oncogene* 19(49):5582-9, MacMillan Press, England (2000).

Gherardi, E., et al., "Functional map and domain structure of MET, the product of the c-met protooncogene and receptor for hepatocyte growth factor/scatter factor," *Proc. Natl. Acad. Sci. U S A.* 100(21):12039-44, National Academy of Sciences, United States (2003).

Giordano, S., et al., "Different point mutations in the met oncogene elicit distinct biological properties," *FASEB J.* 14(2):399-406, The Federation, United States (2000).

Giordano, S. et al., "The semaphorin 4D receptor controls invasive growth by coupling with Met," *Nat. Cell Biol.* 4(9):720-4, MacMillan Magazines Ltd., England (2002).

Hamanoue, M., et al., "Neurotrophic effect of hepatocyte growth factor on central nervous system neurons in vitro," *J. Neurosci. Res.* 43(5):554-64, Wiley Interscience, United States (1996).

Hartmann, G., et al., "The motility signal of scatter factor/hepatocyte growth factor mediated through the receptor tyrosine kinase met requires intracellular action of Ras," *J. Biol. Chem.* 269(35):21936-9, American Society for Biochemistry and Molecular Biology, United States (1994).

Hope, K.J., et al., "Acute myeloid leukemia originates from a hierarchy of leukemic stem cell classes that differ in self-renewal capacity," *Nat. Immunol.* 5(7):738-43, Nature America Inc., United States (2004).

Izumi, Y., et al., "Tumour biology: herceptin acts as an anti-angiogenic cocktail," *Nature* 416(6878):279-80, MacMillan Journals, England (2002).

Jeffers, M., et al., "Hepatocyte growth factor/scatter factor-Met signaling induces proliferation, migration, and morphogenesis of pancreatic oval cells," *Cell Growth Differ.* 7(12):1805-13, The Association, United States (1996).

Jeffers, M., et al., "Activating mutations for the met tyrosine kinase receptor in human cancer," *Proc. Natl. Acad. Sci. U S A* 94(21):11445-50, National Academy of Sciences, United States (1997).

Jemal, A., et al., "Cancer Statistics, 2003," *CA Cancer J Clin.* 53(1):5-26, American Cancer Society, United States (2003).

Jin, L., et al., "Expression of scatter factor and c-met receptor in benign and malignant breast tissue," *Cancer* 79(4):749-760, J. Wiley, United States (1997).

Kuniyasu, H., et al., "Aberrant expression of c-met mRNA in human gastric carcinomas," *Int. J. Cancer* 55(1):72-5, Genève, United States (1993).

Kuukasjärvi, T., et al., "Genetic heterogeneity and clonal evolution underlying development of asynchronous metastasis in human breast cancer," *Cancer Res.* 57(8):1597-604, American Association for Cancer Research, United States (1997).

Lapidot, T., et al., "A cell initiating human acute myeloid leukemia after transplantation into SCID mice," *Nature* 367(6464):645-8, Nature Publishing Group, England (1994).

Liu, C., et al., "Overexpression of c-met proto-oncogene but not epidermal growth factor receptor or c-erbB-2 in primary human colorectal carcinomas," *Oncogene* 7(1):181-5, MacMillan Press, England (1992).

Lorenzato, A., et al., "Novel somatic mutations of the MET oncogene in human carcinoma metastases activating cell motility and invasion," *Cancer Res.* 62(23):7025-30, American Association for Cancer Research, United States (2002).

Maina, F., et al., "Uncoupling of Grb2 from the Met receptor in vivo reveals complex roles in muscle development," *Cell* 87(3):531-42, MIT Press, United States (1996).

Matsumoto, K. and Nakamura, T., "Roles of HGF as a pleiotropic factor in organ regeneration," *EXS* 65:225-49, Birkhauser Verlag, Switzerland (1993).

Maulik, G., et al., "Role of the hepatocyte growth factor receptor, c-Met, oncogenesis and potential for therapeutic inhibition," *Cytokine Growth Factor Rev.* 13(1):41-59, Elsevier Science, England (2002).

Meiners, S., et al., "Role of morphogenetic factors in metastasis of mammary carcinoma cells," *Oncogene* 16(1):9-20, MacMillan Press, England (1998).

Michieli, P., et al., "Targeting the tumor and its microenvironment by a dual-function decoy Met receptor," *Cancer Cell* 6(1):61-73, Cell Press, United States (2004).

Miyaki, M., et al., "Difference in the role of loss of heterozygosity at 10p15 (KLF6 locus) in colorectal carcinogenesis between sporadic and familial adenomatous polyposis and hereditary nonpolyposis colorectal cancer patients," *Oncology* 71(1-2):131-5, Karger, Switzerland (2006).

Morello, S., et al., "MET receptor is overexpressed but not mutated in oral squamous cell carcinomas," *J. Cell Physiol.* 189(3):285-90, Wistar Institute of Anatomy and Biology United States (2001).

Morrison, S.J., et al., "The biology of hematopoietic stem cells," *Annu. Rev. Cell Dev. Biol.* 11:35-71, Annual Reviews, United States (1995).

Morrison, S.J., et al., "Regulatory mechanisms in stem cell biology," *Cell* 88(3):287-98, MIT Press, United States (1997).

Morrison, S.J., et al., "Hematopoietic stem cells: challenges to expectations," *Curr. Opin. Immunol.* 9(2):216-21, Current Science, England (1997).

Mukai, S., et al., "Involvement of Krüppel-like factor 6 (KLF6) mutation in the development of nonpolypoid colorectal carcinoma," *World J. Gastroenterol.* 13(29):3932-8, WJG Press, China (2007).

Muthuramalingam, S.R., et al., "Management of patients with hormone refractory prostate cancer," *Clin. Oncol.* 16(8):505-16, Springer International, England (2004).

Natali, P.G., et al., "Overexpression of the met/HGF receptor in renal cell carcinomas," *Int. J. Cancer* 69(3):212-7, Genève, United States (1996).

Nusrat, A., et al., "Hepatocyte growth factor/scatter factor effects on epithelia. Regulation of intercellular junctions in transformed and nontransformed cell lines, basolateral polarization of c-met receptor in transformed and natural intestinal epithelia, and induction of rapid wound repair in a transformed model epithelium," *J. Clin. Invest.* 93(5):2056-65, American Society for Clinical Investigation, United States (1994).

Olivero, M., et al., "Overexpression and activation of hepatocyte growth factor/scatter factor in human non-small-cell lung carcinomas," *Br. J. Cancer.* 74(12):1862-8, Lewis, England (1996).

Olivero, M., et al., "Novel mutation in the ATP-binding site of the MET oncogene tyrosine kinase in a HPRCC family," *Int. J. Cancer* 82(5):640-3, Genève, United States (1999).

Orian-Rousseau, V., et al., "CD44 is required for two consecutive steps in HGF/c-Met signaling," *Genes Dev.* 16(23):3074-86, Cold Spring Harbor Laboratory Press, United States (2002).

Pandis, N., et al., "Cytogenetic comparison of primary tumors and lymph node metastases in breast cancer patients," *Genes Chromosomes Cancer* 22(2):122-9, Wiley-Liss, United States (1998).

Park, C.H., et al., "Mouse myeloma tumor stem cells: a primary cell culture assay," *J. Natl. Cancer Inst.* 46(2):411-22, Oxford University Press, United States (1971).

Park, M., et al., "Mechanism of met oncogene activation," *Cell* 45(6):895-904, MIT Press, United States (1986).

Ponzetto, C., et al., "Specific uncoupling of GRB2 from the Met receptor. Differential effects on transformation and motility," *J. Biol. Chem.* 271(24):14119-23, American Society for Biochemistry and Molecular Biology, United States (1996).

Royal, I. and Park, M., "Hepatocyte growth factor-induced scatter of Madin-Darby canine kidney cells requires phosphatidylinositol 3-kinase," *J. Biol. Chem.* 270(46):27780-7, American Society for Biochemistry and Molecular Biology, United States (1995).

Schmidt, D. and Beckwith, J.B., "Histopathology of childhood renal tumors," *Hematol. Oncol. Clin. North Am.* 9(6):1179-200, W.B. Saunders, United States (1995).

Schmidt, L., et al., "Germline and somatic mutations in the tyrosine kinase domain of the MET proto-oncogene in papillary renal carcinomas," *Nat. Genet.* 16(1):68-73, Nature Pub. Co., Unites States (1997).

Schmidt, L., et al., "Novel mutations of the MET proto-oncogene in papillary renal carcinomas," *Oncogene* 18(14):2343-50, Nature Publishing Group, England (1999).

Schwall, R.H., et al., "Inhibition of cMet activation by a one-armed antibody," *Proc. Amer. Assoc. Cancer Res. vol. 45*, Clinical Research 5: Emerging Concepts and Targets in Immunotherapy, AACR Meeting Abstracts Online (2004).

Shen, C.Y., et al., "Genome-wide search for loss of heterozygosity using laser capture microdissected tissue of breast carcinoma: an implication for mutator phenotype and breast cancer pathogenesis," *Cancer Res.* 60(14):3884-92, American Association for Cancer Research, United States (2000).

Shively, J.E., "CEACAM1 and hyperplastic polyps: new links in the chain of events leading to colon cancer," *Oncogene* 23(58):9303-5, MacMillan Press, England (2004).

Spiro, S.G. and Porter, J.C., "Lung cancer—where are we today? Current advances in staging and nonsurgical treatment," *Am. J. Respir. Crit. Care. Med.* 166(9):1166-96, American Lung Association, United States (2002).

Suzuki, K., et al., "Expression of the c-met protooncogene in human hepatocellular carcinoma," *Hepatology* 20(5):1231-6, Williams & Wilkins, United States (1994).

Trojan, L., et al., "Prostate cancer therapy: standard management, new options and experimental approaches," *Anticancer Res.* 25(1B):551-561, International Institute of Anticancer Research, Greece (2005).

Trusolino, L., et al., "A signaling adapter function for alpha6beta4 integrin in the control of HGF-dependent invasive growth," *Cell* 107(5):643-54, MIT Press, United States (2001).

Trusolino, L. and Comoglio, P.M., "Scatter-factor and semaphorin receptors: cell signalling for invasive growth," *Nat. Rev. Cancer* 2(4):289-300, Nature Pub. Group, England (2002).

Weitz, J., et al., "Colorectal Cancer," *Lancet* 365(9454):153-65, Lancet Publishing Group, England (2005).

Wu, C., et al., "Simultaneous targeting of multiple disease mediators by a dual-variable-domain immunoglobulin," *Nat. Biotechnol.* 25(11):1290-7, Nature Pub. Co., United States (2007).

Yasuda, A., et al., "Stem cell factor/c-kit receptor signaling enhances the proliferation and invasion of colorectal cancer cells through the PI3K/Akt pathway," *Dig. Dis. Sci.* 52(9):2292-300, Plenum Pub. Corp., United States (2007).

Zhang, G.J., et al., "Optical imaging of tumor cells in hollow fibers: evaluation of the antitumor activities of anticancer drugs and target validation," *Neoplasia* 9(8):652-61, Stockton Press, Canada (2007).

Zhu, Z., et al., "PI3K is negatively regulated by PIK3IP1, a novel p110 interacting protein," *Biochem. Biophys. Res. Commun.* 358(1):66-72, Academic Press, United States (2007).

International Search Report for International Application No. PCT/US2009/003136, United States Patent and Trademark Office, United States, mailed Jan. 21, 2010.

Written Opinion of the International Searching Authority for International Application No. PCT/US2009/003136, United States Patent and Trademark Office, United States, mailed Jan. 21, 2010.

* cited by examiner

Anti-MET Antibodies: Schematic of 13-MET or 28-MET

Anti-MET Monomeric Antibody 13-MET Blocks Binding Between HGF and the MET Receptor Extracellular Domain Anti-MET Monomeric Antibody 28-MET Blocks Binding Between HGF and the MET Receptor Extracellular Domain Anti-MET Antibody 9-MET Blocks Binding
Between HGF and the MET Receptor
Extracellular Domain Anti-MET Antibody 19-MET Blocks Binding Between HGF and the MET Receptor Extracellular Domain A Combination of Anti-MET Antibodies 9-MET and 19-MET Demonstrates Increased Efficacy at Blocking Binding Between HGF and the MET Receptor Extracellular Domain A Combination of Anti-MET Antibodies 9-MET and 19-MET Acts Synergistically to Block Binding Between HGF and the MET Receptor Extracellular Domain A Combination of Anti-MET Antibodies 13-MET and 28-MET IgG Induce Antibody Mediated Cellular Cytotoxicity (ADCC) on GTL-16 Cells A Combination of Anti-MET Antibodies 13-MET and 28-MET Acts Synergistically in Inducing Antibody Mediated Cellular Cytotoxicity (ADCC) on GTL-16 Cells The 13-MET/28-MET Antibody Combination
Eliminates Detectable Phosphorylation of the
Downstream Signaling Protein, SHC

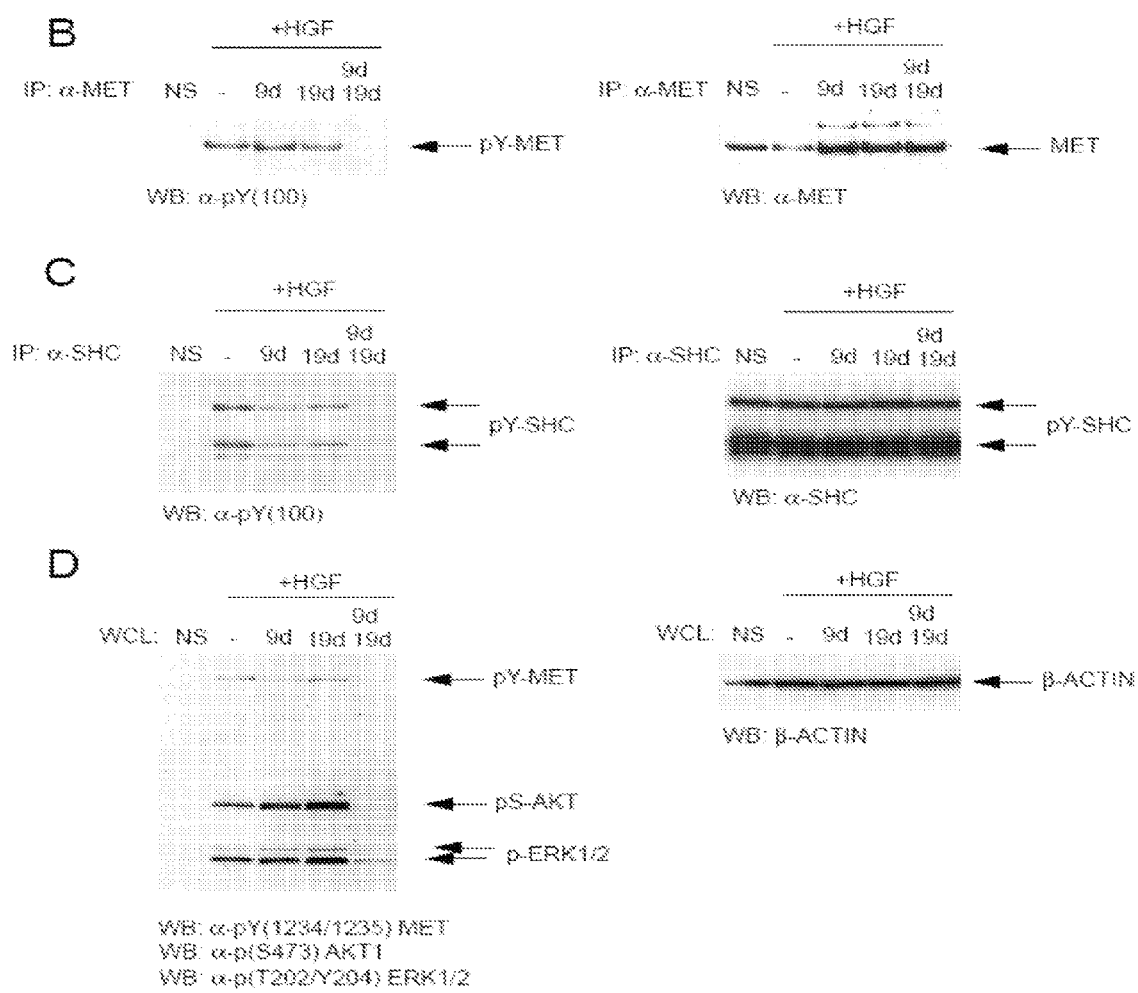
Fig. 4B-D

Figure 5E:
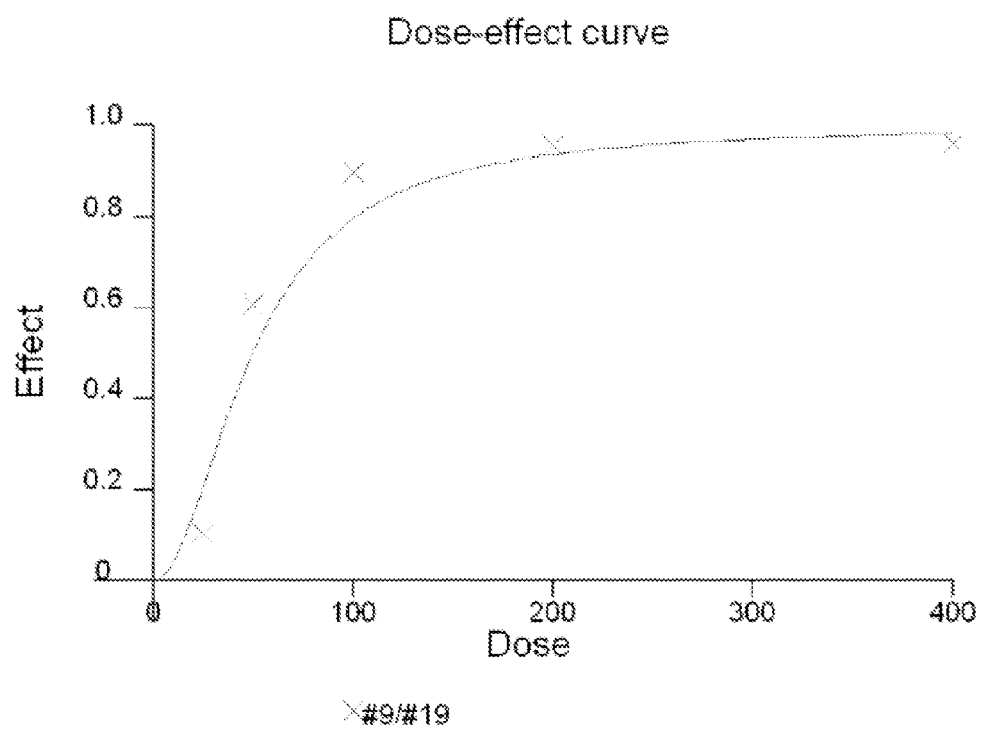
Figure 5F:
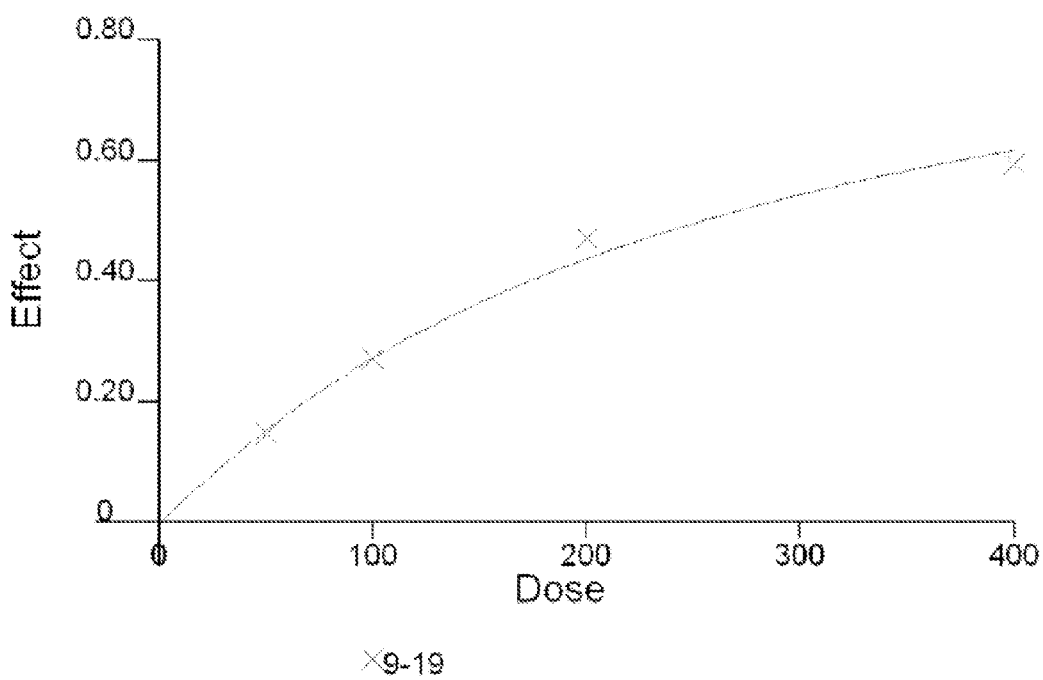
Figure 5G:
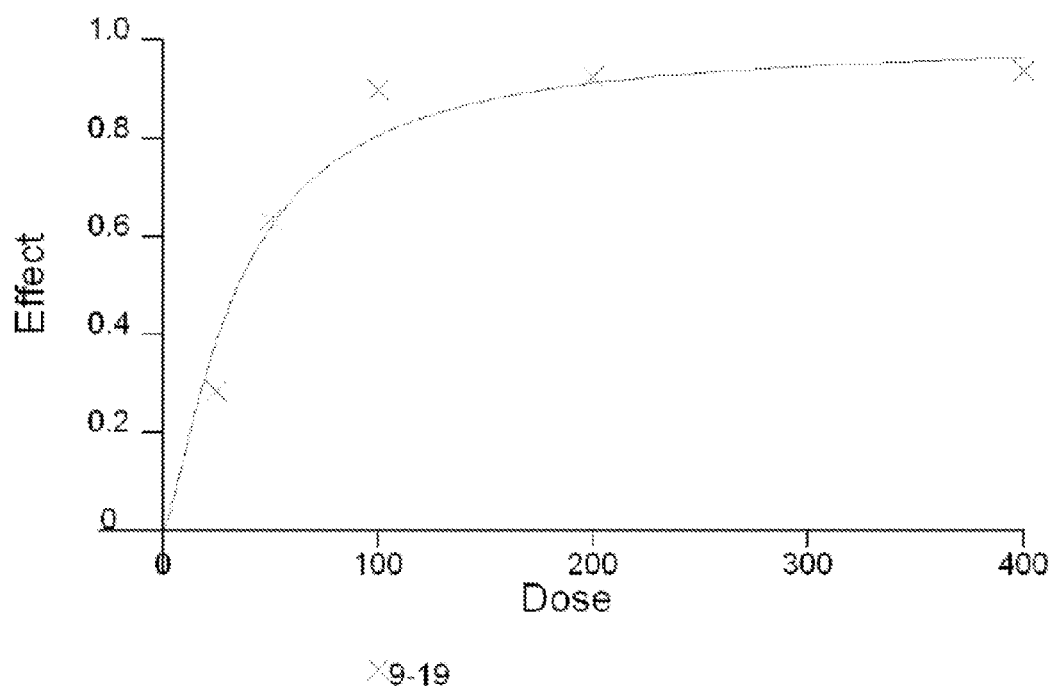
Figure 5H:
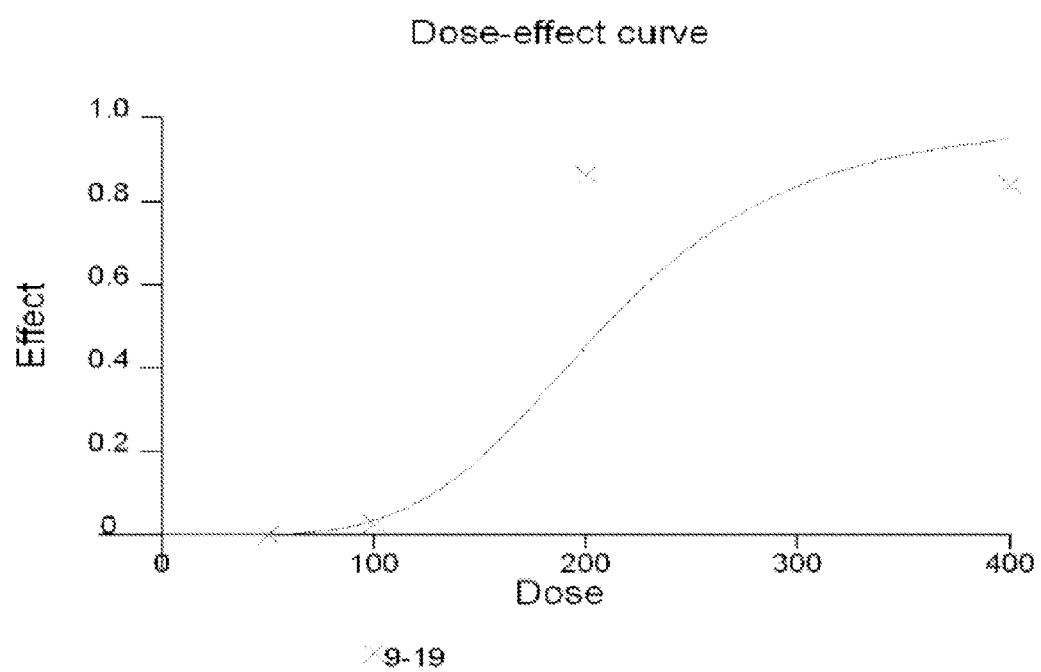

Fig. 5A-B
The 9-MET/19-MET Antibody Combination Disrupts MET Signaling As Effectively as SU in Lung Tumor Cells
A
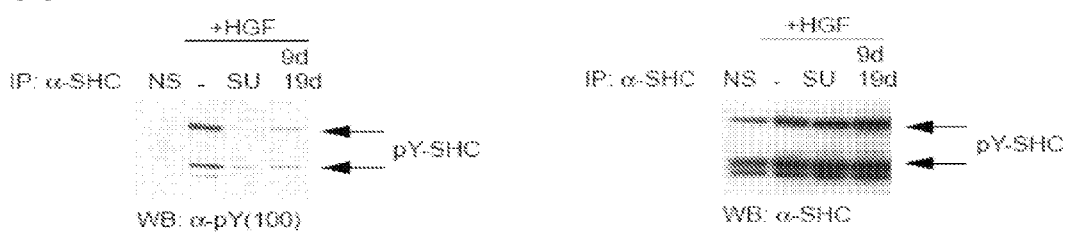
B
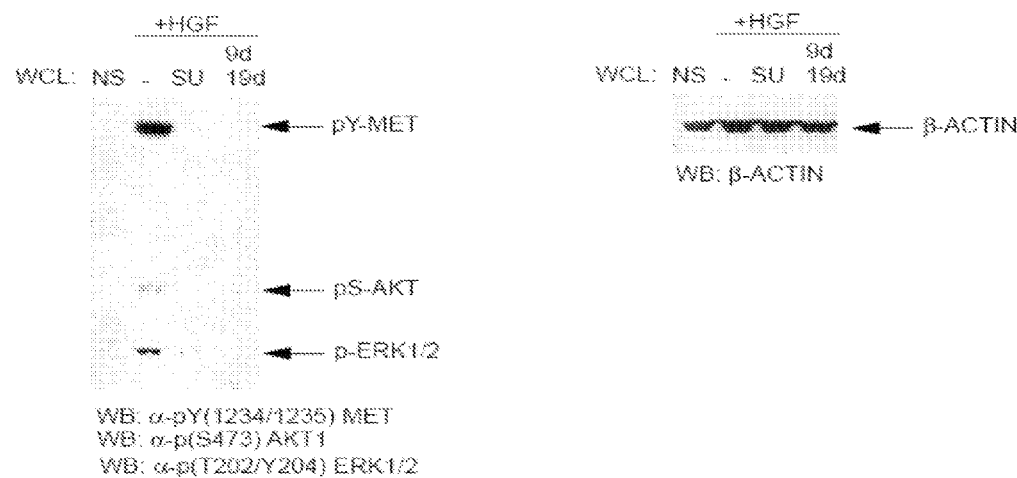

Fig. 5C-D
The 13-MET/28-MET Antibody Combination Disrupts MET Signaling As Effectively as SU in Lung Tumor Cells
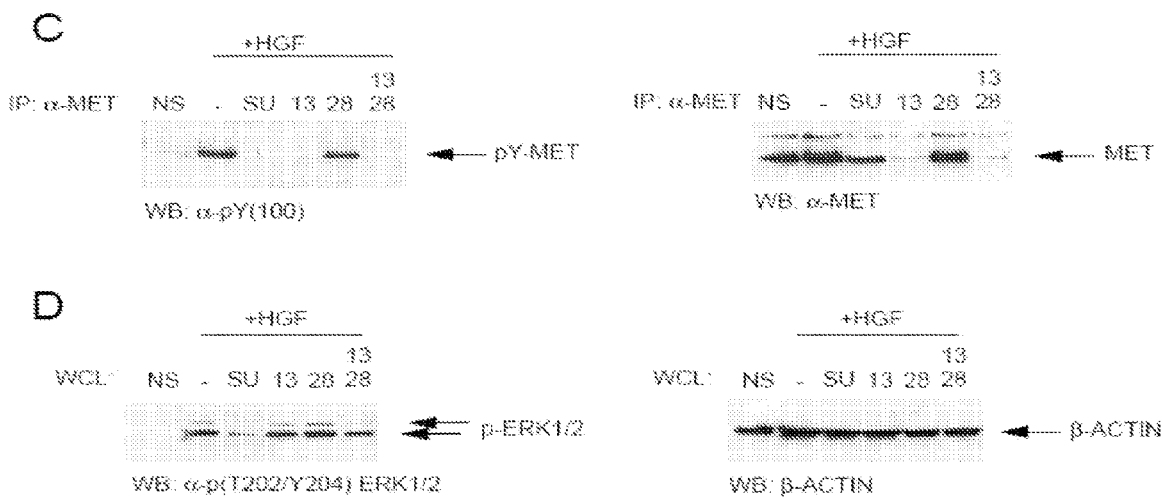

Dose-Effect Curves of the 9-MET/19-MET Antibody Combination on MET Signaling

Fig. 5I

|  |  | Dm | m | r |
|---|---|---|---|---|
|  | E | 49.54589 | 1.93498 | 0.94126 |
| 9-19-MET (1:5) | F | 254.49934 | 1.05279 | 0.99454 |
|  | G | 34.82494 | 1.34288 | 0.93937 |
|  | H | 208.48062 | 4.49411 | 0.94287 |

Fig. 6A-C
The 9-MET/19-MET Antibody Combination
Disrupts MET Signaling As Effectively as SU in
HUVEC Cells
A
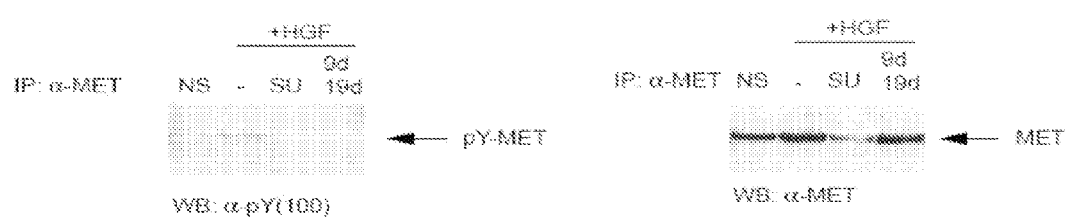
B
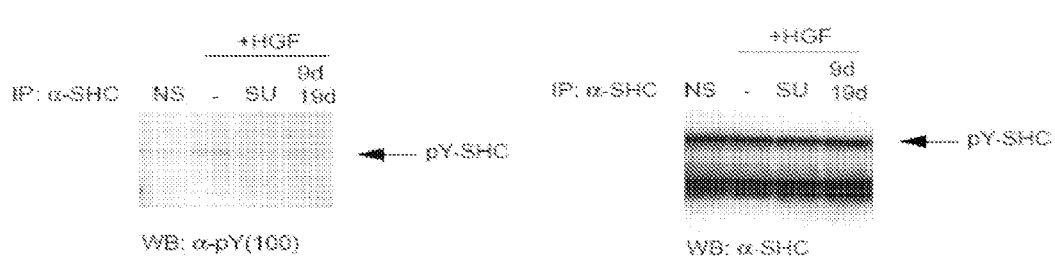
C
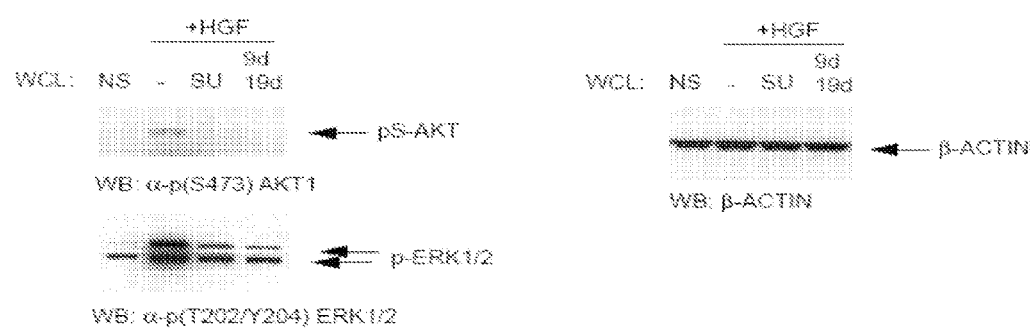

The 9-MET/19-MET Antibody Combination Disrupts HGF-Mediated HUVEC Cell Proliferation The 13-MET/28-MET Antibody
Combination Disrupts HGF-Mediated
Cell Migration The 9-MET/19-MET Antibody Combination
Disrupts HGF-Mediated Cell Migration Anti-MET Antibodies Reduce *In Vivo* Growth of Colon Tumors and Met-Expressing Gastric Carcinoma Cell Line GTL-16

** $p < 0.01$, 73R13/28 (1:8) relative to 1B7.11
*** $p < 0.001$, 73R13/28 (1:8) relative to 1B7.11

* p < 0.05, 73R13/28 (1:8) relative to 1B7.11
*** p < 0.001, 73R13/28 (1:8) relative to 1B7.11

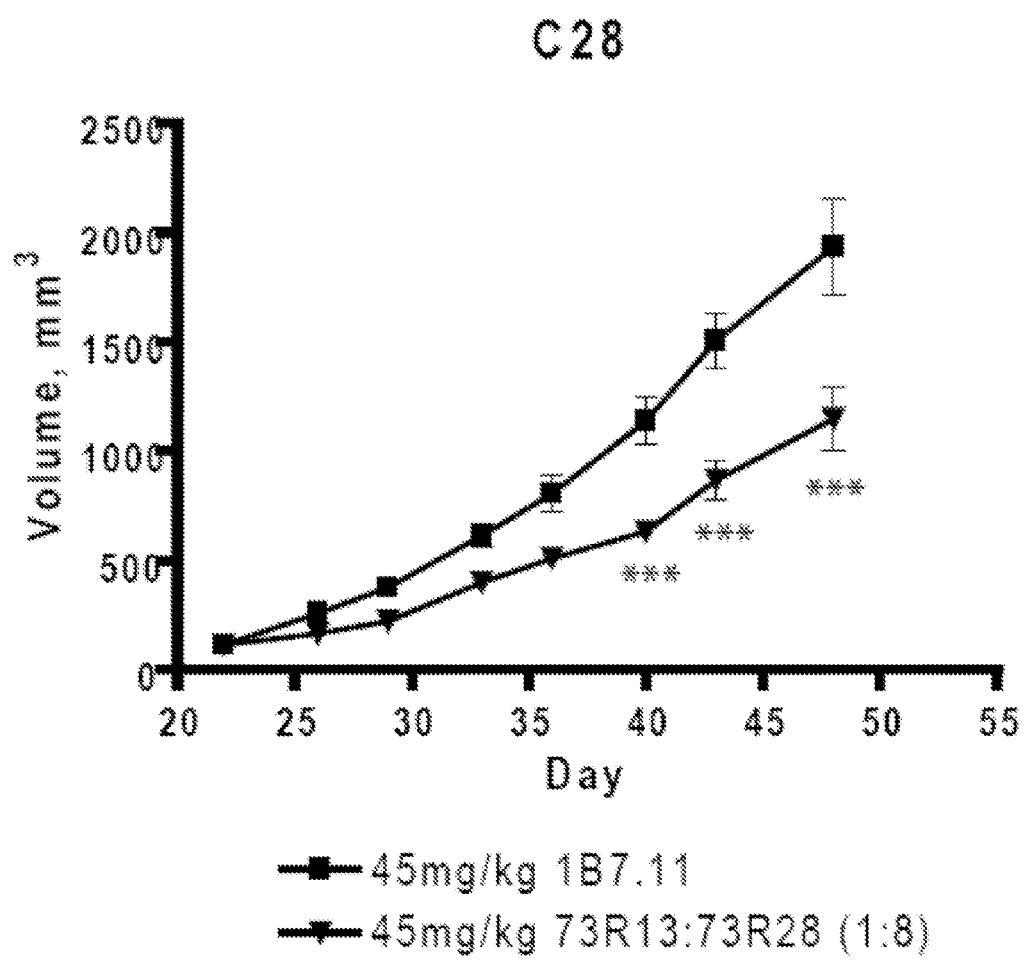

COMPOSITIONS AND METHODS FOR DIAGNOSING AND TREATING CANCER

CROSS-REFERENCE TO RELATED APPLICATIONS

The present application is a U.S. National Phase of International Application No. PCT/US2009/003136, filed May 21, 2009, which claims the benefit of U.S. Provisional Application No. 61/161,275, filed Mar. 18, 2009, U.S. Provisional Application. No. 61/091,265, filed Aug. 22, 2008, and U.S. Provisional Application No. 61/055,088, filed May 21, 2008, each of which are incorporated herein by reference in their entirety.

REFERENCE TO SEQUENCE LISTING SUBMITTED ELECTRONICALLY

The content of the electronically submitted sequence listing (Name: sequence listing.ascii.txt; Size: 49,601 bytes; and Date of Creation: Feb. 18, 2011) filed herewith is incorporated herein by reference in its entirety.

BACKGROUND OF THE INVENTION

1. Field of the Invention

The present invention relates to the field of oncology and provides novel compositions and methods for diagnosing and treating cancer.

2. Background Art

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, *Cancer J. Clin.* 53:5-26).

Breast cancer is the most common cancer in women, with an estimated 12% of women at risk of developing the disease during their lifetime. Although mortality rates have decreased due to earlier detection and improved treatments, breast cancer remains a leading cause of death in middle-aged women, and metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases (American Joint Committee on Cancer: AJCC Cancer Staging Manual. Philadelphia, Pa.: Lippincott-Raven Publishers, 5th ed., 1997, pp 171-180; Harris, J R: "Staging of breast carcinoma" in Harris, J. R., Hellman, S., Henderson, I. C., Kinne D. W. (eds.): Breast Diseases. Philadelphia, Lippincott, 1991). These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, *CA Cancer J. Clin.* 53:5-26). Since the introduction of the prostate specific antigen (PSA) blood test, early detection of prostate cancer has dramatically improved survival rates; the five year survival rate for patients with local and regional stage prostate cancers at the time of diagnosis is nearing 100%. Yet more than 50% of patients will eventually develop locally advanced or metastatic disease (Muthuramalingam et al., 2004, *Clin. Oncol.* 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, *Clin. Oncol.* 16:505-16; Trojan et al., 2005, *Anticancer Res.* 25:551-61).

Colorectal cancer is the third most common cancer and the fourth most frequent cause of cancer deaths worldwide (Weitz et al., 2005, *Lancet* 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinomas invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through the muscularis propria and may penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50% and is now the standard of care for these patients.

Lung cancer is the most common cancer worldwide, the third most commonly diagnosed cancer in the United States, and by far the most frequent cause of cancer deaths (Spiro et al., 2002, *Am. J. Respir. Crit. Care Med.* 166:1166-96; Jemal et al., 2003, *CA Cancer J. Clin.* 53:5-26). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, *Am. J. Respir. Crit. Care Med.* 166:1166-96).

These four cancers, as well as many others, present as solid tumors that are composed of heterogeneous cell populations. For example, breast cancers are a mixture of cancer cells and normal cells, including mesenchymal (stromal) cells, inflammatory cells, and endothelial cells. Several models of cancer provide different explanations for the presence of this heterogeneity. One model, the classic model of cancer, holds that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells have some degree of tumorigenic potential. (Pandis et al., 1998, *Genes, Chromosomes & Cancer* 12:122-129; Kuukasjrvi et al., 1997, *Cancer Res.* 57:1597-1604; Bonsing et al., 1993, *Cancer* 71:382-391; Bonsing et al., 2000, *Genes Chromosomes & Cancer* 82: 173-183; Beerman H et al., 1991, *Cytometry* 12:147-54; Aubele M & Werner M, 1999, *Analyt. Cell. Path.* 19:53; Shen L et al., 2000, *Cancer Res.* 60:3884).

An alternative model for the observed solid tumor cell heterogeneity derives from the impact of stem cells on tumor development. According to this model, cancer arises from dysregulation of the mechanisms that control normal tissue development and maintenance. (Beachy et al., 2004, *Nature* 432:324). During normal animal development, cells of most or all tissues are derived from normal precursors, called stem cells (Morrison et al., 1997, *Cell* 88:287-98; Morrison et al., 1997, *Curr. Opin. Immunol.* 9:216-21; Morrison et al., 1995, *Annu. Rev. Cell. Dev. Biol.* 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-studied example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain. Tumors derived from a "solid tumor stem cell" (or "cancer stem cell" from a solid tumor) subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, *Nature* 17:645-8). More recently it has been demonstrated that malignant human breast tumors similarly harbor a small, distinct population of cancer stem cells enriched for the ability to form tumors in immunodeficient mice. An ESA+, CD44+, CD24−/low, Lin-cell population was found to be 50-fold enriched for tumorigenic cells compared to unfractionated tumor cells (Al-Hajj et al., 2003, *Proc. Nat'l Acad. Sci.* 100:3983-8). The ability to prospectively isolate the tumorigenic cancer cells has permitted investigation of critical biological pathways that underlie tumorigenicity in these cells, and thus promises the development of better diagnostic assays and therapeutics for cancer patients. It is toward this purpose that this invention is directed.

BRIEF SUMMARY OF THE INVENTION

Provided are antibodies that specifically bind to receptors such as the human MET Receptor. In certain embodiments, the antibodies are humanized antibodies or human antibodies. In certain embodiments, these antibodies inhibit MET Receptor interactions with HGF ligand binding and downstream MET Receptor signaling. Also provided are pharmaceutical compositions comprising the antibodies of the present disclosure and a pharmaceutically acceptable vehicle. Further provided are methods of treating cancer comprising administering the antibodies of the present disclosure in a therapeutically effective amount.

In another aspect, the invention provides a method of inhibiting the functioning or signaling by a receptor (e.g., a human Met receptor or other human receptor tyrosine kinase) on a cell comprising contacting the cell with an effective amount of either (a) an antibody that specifically binds both a first epitope and a second epitope on the extracellular domain of the receptor, or (b) a combination of antibodies comprising (i) a first antibody that binds a first epitope on the extracellular domain of the receptor and (ii) a second antibody that binds a second epitope on the extracellular domain of the same receptor. In certain embodiments, the first epitope does not overlap with the second epitope. In certain embodiments, the binding of the antibody to the first epitope inhibits binding of a ligand to the receptor by direct competition and/or binds to the ligand binding site on the receptor. In some embodiments, the second epitope is a conformational epitope and/or binding to the second epitope does not compete directly with ligand binding, but nonetheless inhibits binding of the ligand to the receptor. In some embodiments, binding of the antibody or antibodies to the combination of both the first and second epitopes synergistically inhibits ligand binding.

In still another aspect, the invention provides a method of inhibiting tumor growth and/or treating cancer in a patient comprising administering to the patient a therapeutically effective amount of a multispecific antibody that specifically binds both a first epitope and a second epitope on the extracellular domain of a human Met receptor. In certain embodiments, the first epitope does not overlap with the second epitope. In certain embodiments, binding of the antibody to the first epitope inhibits HGF binding to the Met receptor and/or binding of the antibody to the second epitope inhibits HGF binding to the Met receptor. In certain embodiments, binding both the first and second epitope synergistically inhibits HGF binding. In certain embodiments, binding of the antibody to the first epitope directly competes with binding of HGF to the Met receptor and/or the first epitope is in the SEMA domain of the Met receptor. In certain embodiments, binding of the antibody to the second epitope does not directly compete with binding of HGF to the Met receptor and/or the second epitope is a conformational epitope. In certain embodiments, binding of the antibody to the first epitope increases the avidity of the antibody to the second epitope.

In yet another aspect, the invention provides a method of inhibiting tumor growth and/or treating cancer in a patient comprising administering to the patient a therapeutically effective amount of a combination of antibodies comprising (i) a first antibody that binds a first epitope on the extracellular domain of a human Met receptor and (ii) a second antibody that binds a second epitope on the extracellular domain of the same receptor. In certain embodiments, the first epitope does not overlap with the second epitope. In certain embodiments, binding of each of the antibodies alone inhibits HGF binding to the Met receptor. In some embodiments, the binding of the two antibodies together synergistically inhibits HGF binding. In certain embodiments, binding of the first antibody directly competes with binding of HGF to the Met receptor and/or the first antibody binds to the SEMA domain. In certain embodiments, the second antibody, although it inhibits HGF binding to the Met receptor does not directly compete with HGF for binding and/or the second epitope is a conformational epitope. In certain embodiments, binding of the first antibody to the first epitope increases the avidity of the second antibody for the second epitope.

In another aspect, the invention provides the antibodies 13-MET, 21-MET, and 28-MET, each of which specifically binds to the human Met receptor and inhibits HGF binding to the receptor.

In another aspect, the invention provides an antibody that specifically binds to the extracellular domain of the human MET receptor and comprises at least one (i.e., one, two, three, four, five, or six) CDRs of 13-MET, 21-MET, or 28-MET.

In another aspect, the invention provides an antibody that specifically binds to the extracellular domain of the human MET receptor and comprises a heavy chain variable region having at least about 90% identity to the heavy chain variable region of 13-MET and/or at least about 90% identity to the light chain variable region of 13-MET.

In another aspect, the invention provides an antibody that specifically binds to the extracellular domain of the human MET receptor and comprises a heavy chain variable region having at least about 90% identity to the heavy chain variable region of 28-MET and/or at least about 90% identity to the light chain variable region of 28-MET or 21-MET.

In another aspect, the invention provides an antibody that competes for specific binding to a human Met receptor with the 13-MET, 21-MET, and/or 28-MET antibody.

In some embodiments of each of the aforementioned aspects, as well as other aspects described herein, the antibodies inhibit HGF binding to the human Met receptor.

In some embodiments of each of the aforementioned aspects, as well as other aspects described herein, the antibodies are monoclonal antibodies. In some embodiments, the antibodies are human or humanized antibodies. In some embodiments, the antibodies are multispecific (e.g., bispecific) antibodies. In some embodiments, the multispecific or bispecific antibodies specifically bind to more than one epitope on the extracellular domain of the Met receptor. In certain embodiments, the different epitopes on the Met receptor to which the multispecific or bispecific antibody binds are non-overlapping. In some embodiments, the antibodies are isolated. Methods of inhibiting the functioning of or signaling by a Met receptor on a cell comprising contacting the cell with an effective amount of one or more of the antibodies described herein is also provided. Methods of inhibiting tumor growth and methods of treating cancer in a patient comprising administering to the patient a therapeutically effective amount of the antibody of one or more of the antibodies described herein are also provided.

Polypeptide comprising fragments of the antibodies, as well as polynucleotides encoding the polypeptides or antibodies are also provided.

Compositions, such as pharmaceutical compositions comprising the antibodies are also provided.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention, as claimed. The accompanying drawings, which are incorporated in and constitute a part of this specification, illustrate several embodiments of the invention and, together with the description, serve to explain the principles of the invention. In the specification and the appended claims, the singular forms "a," "an," and "the" include plural reference unless the context clearly dictates otherwise.

BRIEF DESCRIPTION OF THE DRAWINGS/FIGURES

Figure 1B:
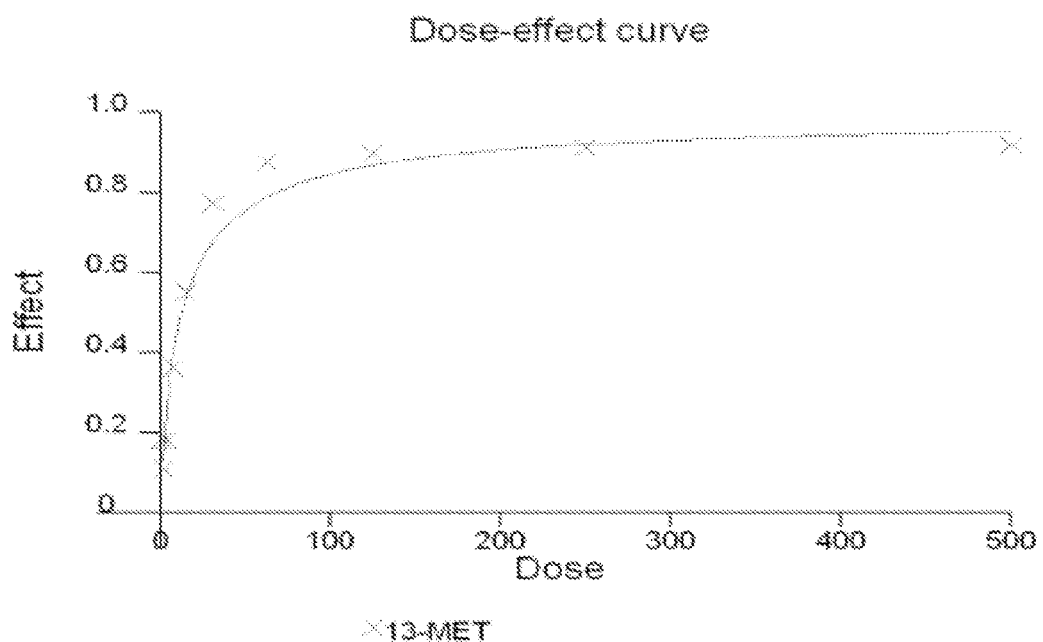
Figure 1C:
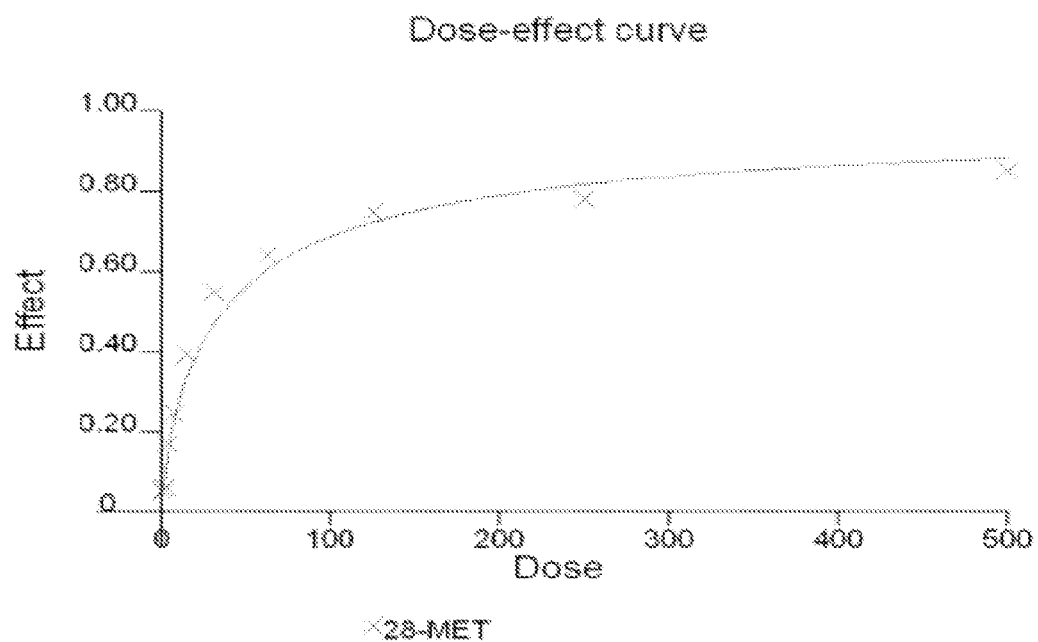

FIG. 1: Anti-MET Antibodies Block Binding Between HGF and the MET Receptor Extracellular Domain. (A) A schematic of the different Met Receptor antibodies generated. Each monovalent Fab (Fab 13 or 28 monomeric Fab) was linked to itself via a helix loop helix motif to produce divalent dimer Fabs (dimeric Fab-dHLX) in which two 13-MET Fabs were linked to produce the dimer 9-MET or two 28-MET Fabs were linked to produce the dimer 19-MET. Similarly, each monovalent Fab was used to generate a human IgG1 antibody (IgG 13 or IgG 28). (B, C) The effect (y-axis) of monomeric anti-MET antibodies 13-MET (B) and 28-MET (C) on blocking MET binding to HGF is shown for increasing doses of each antibody (x-axis; nM). The effect at each dose is marked with an "X", and a dose-effect curve graphed for each antibody. Dm=IC50; m=slope of the curve, r=curvefit value.

Figure 2A:
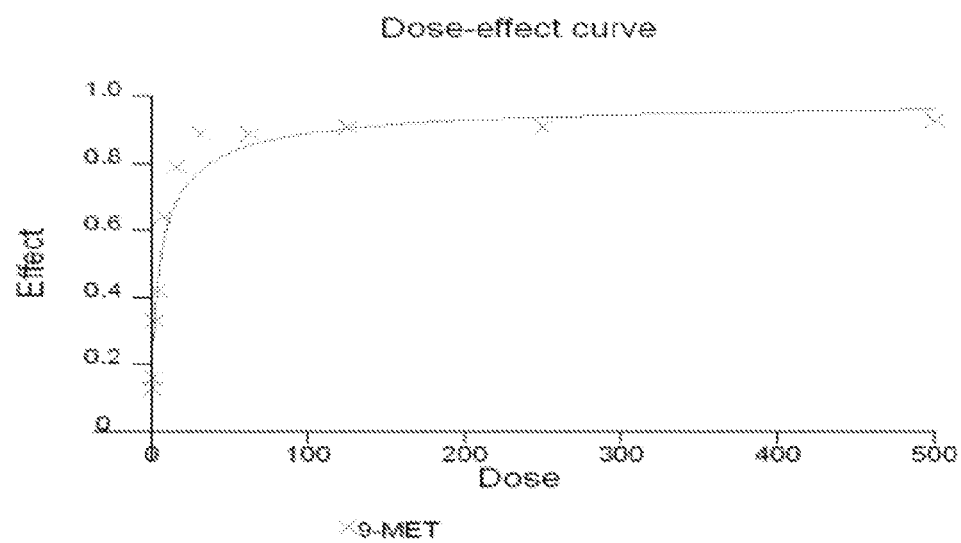
Figure 2B:
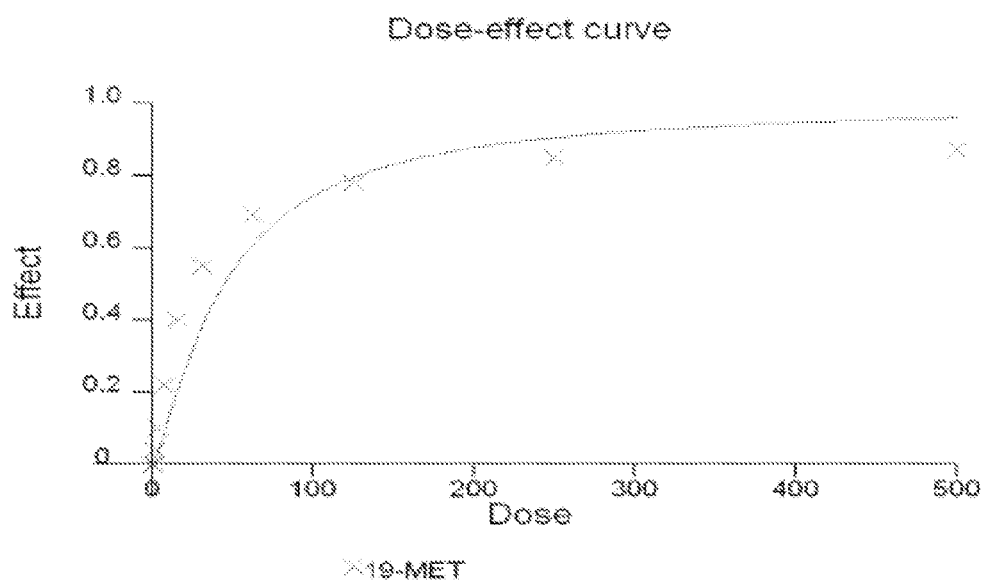

FIG. 2: Anti-MET Antibodies Block Binding Between HGF and the MET Receptor Extracellular Domain. The effect (y-axis) of dimeric anti-MET antibodies 9-MET (A) and 19-MET (B) of blocking MET binding to HGF is shown for increasing doses of each antibody (x-axis; nM). The effect at each dose is marked with an "X", and a dose-effect curve graphed for each antibody. Dm=IC50; m=slope of the curve, r=curvefit value.

FIG. 3: A Combination of Anti-MET Antibodies 9-MET and 19-MET Act Synergistically to Block Binding Between HGF and the MET Receptor Extracellular Domain. (A) The effect (y-axis) of anti-MET antibodies 19-MET (circles), 9-MET (crosses), and a combination of 9-MET/19-MET (1:5) (x's) of blocking MET binding to HGF is shown for increasing doses of each antibody or antibody combination (x-axis; nM). The effect at each dose is marked with its corresponding symbol, and a dose-effect curve graphed for each antibody. (B) A conservative isobologram demonstrates that the 9-MET/19-MET antibody combination acts synergistically to block HGF binding to MET. The effective dose (ED) 50 (X), ED75 (crosses) and ED90 (circles) are graphed. Dm=IC50; m=slope of the curve, r=curvefit value. (C) A Combination of Anti-MET Antibodies 9-MET and 19-MET Act Synergistically to induce antibody-dependent cellular cytotoxicity in GTL-16 cancer cells (ADCC). The effect (y-axis) of anti-MET antibodies 13-MET (crosses), 28-MET (circles), and a combination of 13-MET/28-MET (1:5) (x's) inducing ADCC on GTL-16 cells is shown for increasing doses of each antibody or antibody combination (x-axis; nM). The effect at each dose is marked with its corresponding symbol, and a dose-effect curve graphed for each antibody. (D) A conservative isobologram demonstrates that the 13-28-MET antibody combination acts synergistically to induce ADCC on GTL-16 cells. The effective dose (ED) 50 (X), ED75 (crosses) and ED90 (circles) are graphed. Dm=IC50; m=slope of the curve, r=curvefit value.

FIG. 4: A Combination of Anti-MET Antibodies Eliminates Detectable Phosphorylation of MET and Downstream Signaling Proteins in Lung Tumor Cells. Cells incubated without (NS) or with HGF (+HGF) in the presence or absence (−) of 13-MET (13m), 28-MET (28m), and a combination of 13-MET/28-MET (13m 28m) antibodies (A) or 9-MET (9d), 19-MET (19d), and a combination of 9-MET/19-MET (9d 19d) antibodies (B-D) were analyzed by immunoblotting either as whole cell lysates (WCL) or by immunoprecipitation (IP) with antibodies that recognize the phosphorylated form (left blots) or total protein (right blots) of the MET receptor (B, D); the downstream signaling molecules SHC (A, C), AKT (D), and ERK1/2 (D); or Actin as a loading control (D). While each antibody alone decreases phosphorylation of MET and/or phosphorylation of downstream signaling molecules, the antibody combinations eliminate or nearly eliminate detectable phorphorylation.

FIG. 5: A Combination of Anti-MET Antibodies Disrupts MET Signaling as Effectively as SU11274 in Lung Tumor Cells. Cells incubated without (NS) or with HGF (+HGF) in the presence or absence (−) of 13-MET (13), 28-MET (28), a combination of 13-MET/28-MET (13 28) antibodies (C, D), a combination of 9-MET/19-MET (9d 19d) antibodies (A, B), or SU11274 (SU) were analyzed by immunoblotting either as whole cell lysates (WCL) or by immunoprecipitation (IP) with antibodies that recognize the phosphorylated form (left blots) or total protein (right blots) of the MET receptor (B, C); the downstream signaling molecules SHC (A), AKT (B), and ERK1/2 (B, D); or Actin as a loading control (B, D). The antibody combinations eliminate detectable phosphorylation of MET and downstream signaling molecules as effectively as SU11274. (E-I) The dose-effect of the 9-MET/19-MET combination (1:5) on phosphorylation of MET at Y1230/Y1234/Y1235 (E) or at Y1349 (F); AKT1 at 5473 (G), and ERK1/2 at T185/Y187 (H) are graphed and the Dm=IC50; m=slope of the curve, r=curvefit value are calculated for each (I).

Figure 6D:
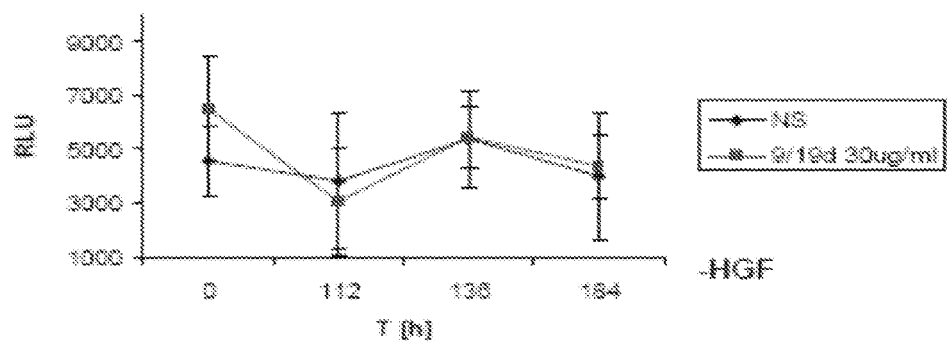
Figure 6D:
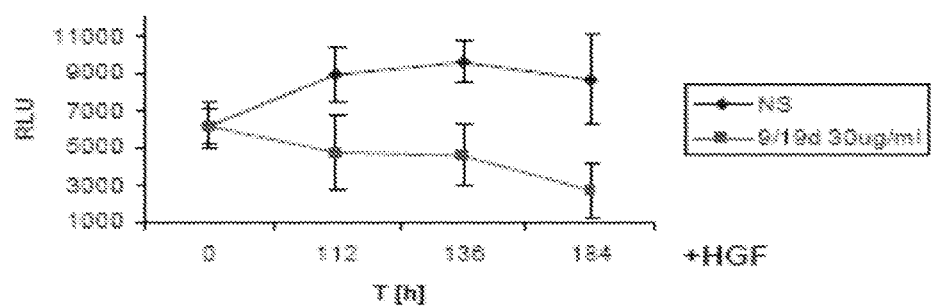

FIG. 6: A Combination of Anti-MET Antibodies Disrupts MET Signaling and HGF-Mediated Proliferation of HUVEC Cells. Cells incubated without (NS) or with HGF (+HGF) in the presence or absence (−) of a combination of 9-MET/19-MET (9d 19d) antibodies or SU11274 were analyzed by immunoblotting either as whole cell lysates (WCL) or by immunoprecipitation (IP) with antibodies that recognize the phosphorylated form (left blots) or total protein (right blots) of the MET receptor (A); the downstream signaling molecules SHC (B), AKT (C), and ERK1/2 (C); or Actin as a loading control (C). The 9-MET/19-MET antibody combination eliminated detectable phosphorylation of MET and downstream signaling molecules as effectively as SU11274 in HUVEC cells. (D) Cell proliferation was measured in the absence (upper graph) or the presence (lower graph) of HGF. Cells were incubated with 9-19-MET antibodies (squares) or control medium (diamonds) over 7 days. Treatment of HUVEC cells with 9-19-MET antibodies disrupted HGF-mediated cell proliferation.

Figure 7A:
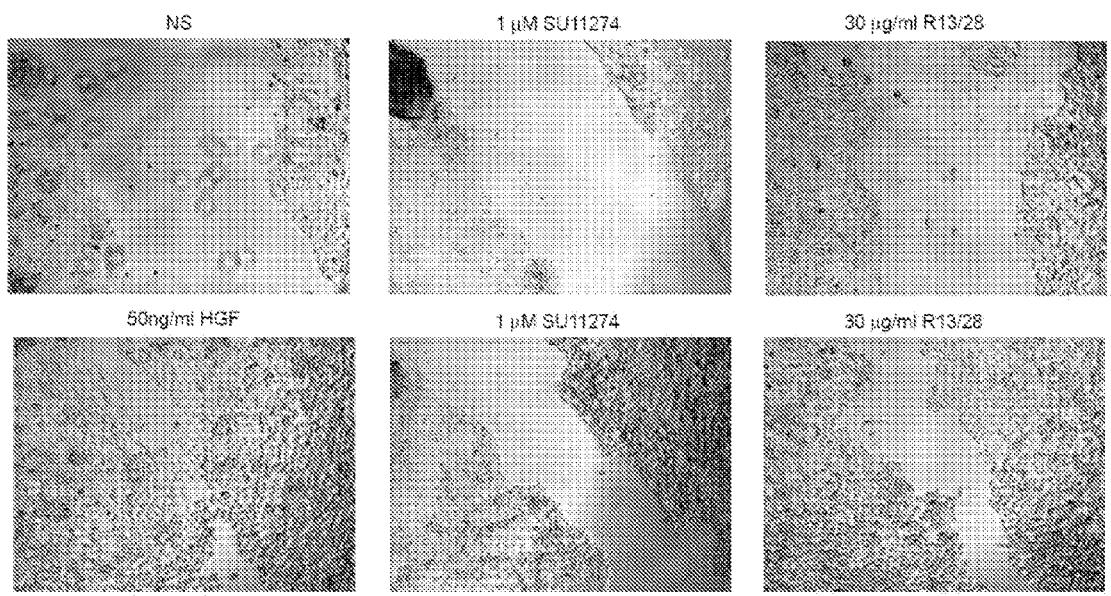
Figure 7B:
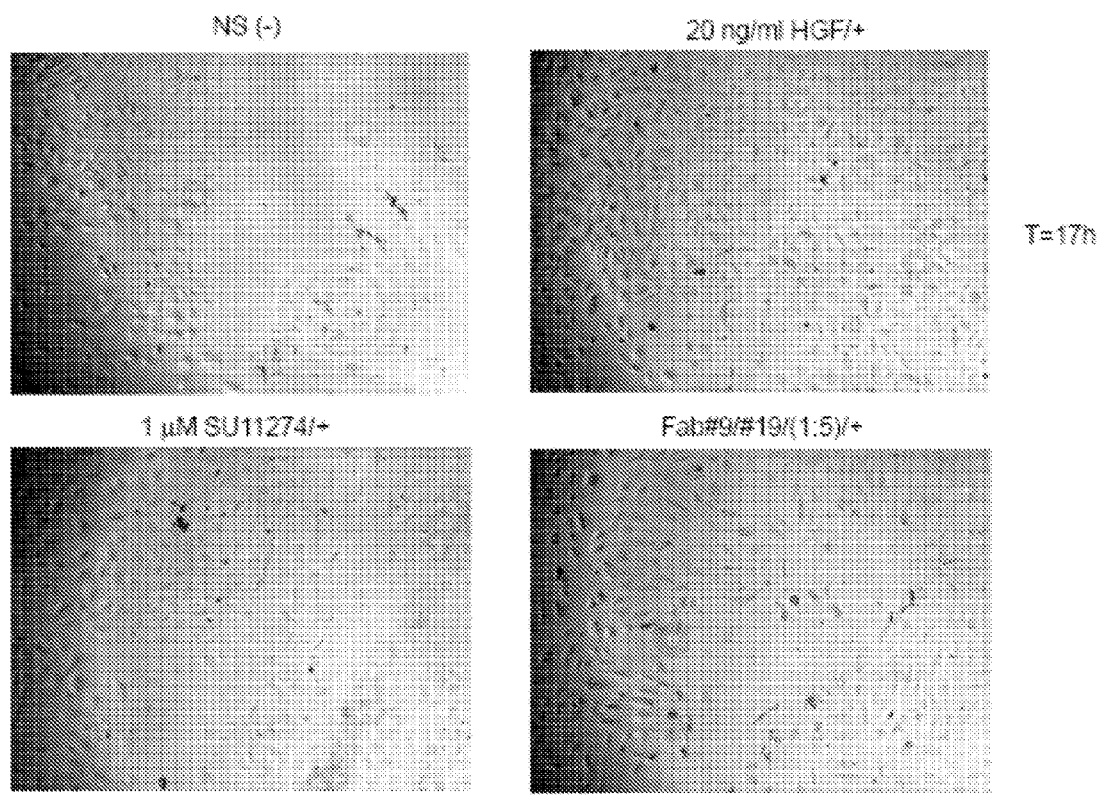

FIG. 7: A Combination of Anti-MET Antibodies Disrupts HGF-Mediated Cell Migration. (A) H441 cells in which a scrape has been made through the monolayer were treated with control media (top row) or HGF (bottom row) either alone (left), in the presence of SU11274 (middle), or in the presence of a combination of 13-MET/28-MET antibodies at 30 ug/ml (right). Photographs show results 16 hours after exposure to HGF. (B) HUVEC cells in which a scrape has been made through the monolayer were treated with control media (top, left) or HGF either alone (top, right) or in the presence of SU11274 (bottom, left) or 9-MET/19-MET Fab combination of antibodies (bottom, right). Photographs show results 17 hours after exposure to HGF.

Figure 8:
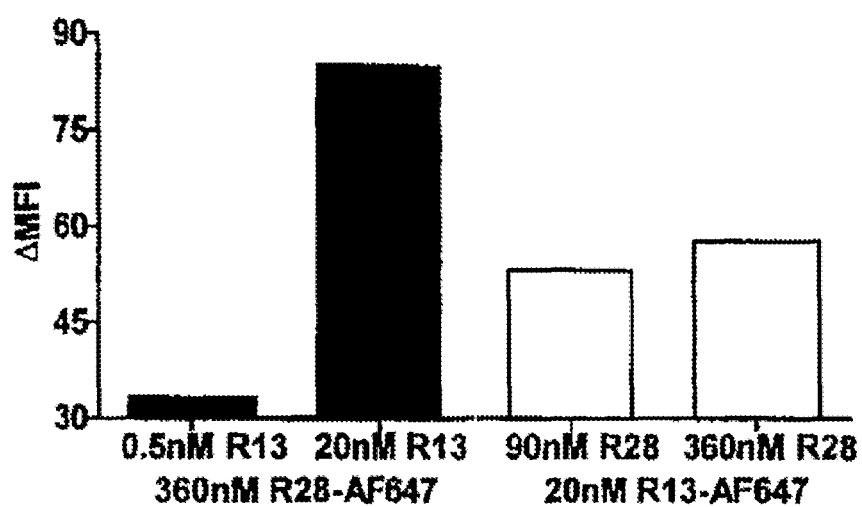

FIG. 8: Anti-MET Antibody Combinations Synergistically Block MET Receptor function. AF647-conjugated R28 (black bars) or R13 (white bars) were used as FACS-reagents to detect MET-receptor on GTL-16 cells. AF647-labeled antibodies (AF647-R28 or AF647-R13) were used at fixed concentrations (360 nM, AF647-R28; 20 nM, AF647-R13) and unlabeled R13 (0.5 nM, 20 nM) or R28 (90 nM, 360 nM) was titered in. Note that 20 nM of R13 increased MFI-values (ΔMFI) for AF647-R28 by 2.6 fold, whereas adding R28 to AF647-R13 did not show any effect. ΔMFI values were determined by subtracting background MFI. NS indicates not stimulated. Arrows indicate the detected proteins. bars, SD. Kd values for the antibodies remained unchanged (data not shown).

FIG. 9: Anti-MET Antibodies Reduce In Vivo Growth of Colon Tumors and Met-Expressing Gastric Carcinoma Cell Line GTL-16. (A) Immunodeficient mice were injected with GLT-16 cells and established tumors treated with either control antibody 1B7.11 (squares) or anti-MET antibodies 13-MET and 28-MET at a ratio of 1:8 (inverted triangles). Tumor volume (x-axis) is plotted over time (y-axis). Administration of a 1:8 ratio of 13-MET to 28-MET antibodies resulted in a statistically significant decrease in tumor volume compared to control antibody treated animals at day 15 ($p<0.01$) and at day 19 to 22 ($p<0.001$) post-injection. (B) Immunodeficient mice were injected with OMP-C12 colon tumor cells and established tumors treated with anti-MET antibodies 13-MET and 28-MET at a ratio of 1:8 (inverted triangles). Tumor volume (x-axis) is plotted over time (y-axis). Administration of a 1:8 ratio of 13-MET to 28-MET antibodies resulted in a statistically significant decrease in tumor volume compared to control antibody treated animals at day 77 ($p<0.01$) and at day 81 to day 105 ($p<0.001$) post-injection. (C) Immunodeficient mice were injected with OMP-C17 colon tumor cells and established tumors treated with anti-MET antibodies 13-MET and 28-MET at a ratio of 1:8 (inverted triangles). Tumor volume (x-axis) is plotted over time (y-axis). Administration of a 1:8 ratio of 13-MET to 28-MET antibodies resulted in a statistically significant decrease in tumor volume compared to control antibody treated animals at day 58 ($p<0.01$) and day 62 ($p<0.001$) post-injection. (D) Immunodeficient mice were injected with OMP-C27 colon tumor cells and established tumors treated with anti-MET antibodies 13-MET and 28-MET at a ratio of 1:8 (inverted triangles). Tumor volume (x-axis) is plotted over time (y-axis). Administration of a 1:8 ratio of 13-MET to 28-MET antibodies resulted in a statistically significant decrease in tumor volume compared to control antibody treated animals at day 41 ($p<0.05$) and day 44 to 48 ($p<0.001$) post-injection. (E) Immunodeficient mice were injected with OMP-C28 colon tumor cells and treated with anti-MET antibodies 13-MET and 28-MET at a ratio of 1:8 (inverted triangles). Tumor volume (x-axis) is plotted over time (y-axis). Administration of a 1:8 ratio of 13-MET to 28-MET antibodies resulted in a statistically significant decrease in tumor volume compared to control antibody treated animals at day 40 to 48 ($p<0.001$) post-injection. (F) Immunodeficient mice were injected with GLT-16 cells and established tumors treated with either control antibody 1B7.11 (squares) or an anti-MET bispecific antibody 73R21.13 (triangles). Tumor volume (x-axis) is plotted over time (y-axis). Administration of the anti-MET bispecific antibody 73R21.13 resulted in a statistically significant decrease in tumor volume compared to control antibody treated animals.

Figure 10:
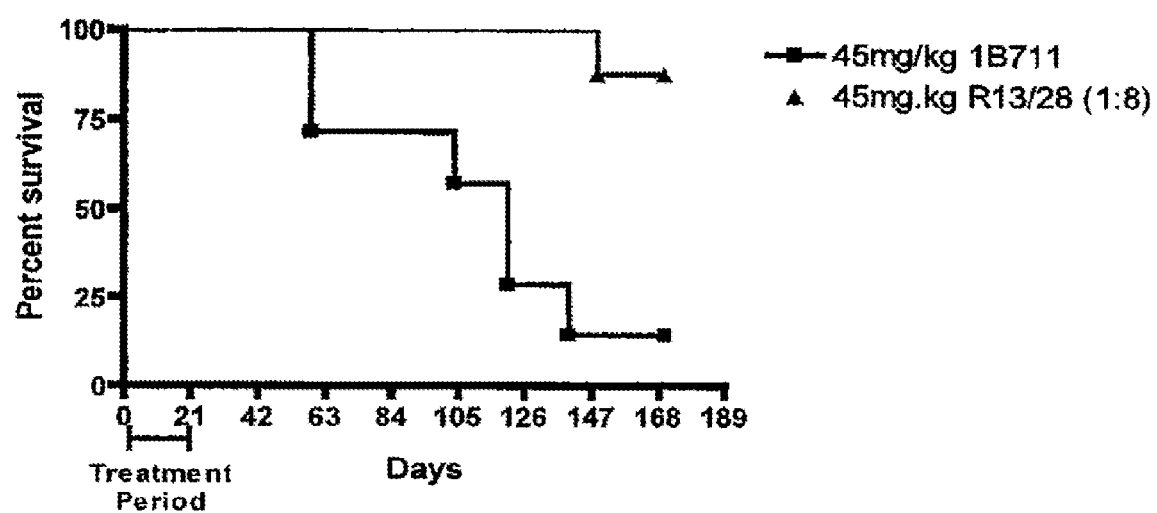

FIG. 10: Anti-MET Antibodies Increase Survival by Decreasing Lung Metastases. Mice were injected with GTL-16 cells stably expressing the luciferase (luc)-gene and treated weekly with 13-MET/28-MET antibodies at a ratio of 1:8 or control antibody 1B711. Treatment was stopped after three weeks and the disease recurrence was measured by non-invasive imaging every week. At day 170, only one mouse in the 13-MET/28-MET-treatment group had died, whereas in the control group six out of seven mice had died.

DETAILED DESCRIPTION OF THE INVENTION

The term "antibody" is used to mean an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In certain embodiments, antibodies of the present invention include antagonist antibodies that specifically bind to a cancer stem cell marker protein and interfere with, for example, ligand binding, receptor dimerization, expression of a cancer stem cell marker protein, and/or downstream signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, antibody internalization and/or recognized by the immune system. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g. rodent) antibodies that are specific immunoglobulin chains, chimeric immunoglobulins, or fragments thereof that contain minimal non-human sequences. Typically, humanized antibodies are human immunoglobulins in which residues from the complementary determining regions (CDRs) within the antigen determination region (or hypervariable region) of the variable region of an antibody chain or chains are replaced by residues from the CDR of a non-human species (e.g. mouse, rat, rabbit, hamster) that have the desired specificity, affinity, and capability. In some instances, residues from the variable chain framework region (FR) of a human immunoglobulin are replaced with the corresponding residues in an antibody from a non-human species that has the desired specificity, affinity, and capability. The humanized antibody can be further modified by the substitution of additional residue either in the variable framework region and/or within the replaced non-human residues to refine and optimize antibody specificity, affinity, and/or capability. In general, the humanized antibody will comprise substantially all of at least one, and typically two or three or four, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

An "affinity matured" antibody is one with one or more alterations in one or more CDRs thereof which result in an improvement in the affinity of the antibody for antigen compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc. Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226389-896 (1992).

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a $K_D$ of at least about 0.1 mM, but more usually at least about 1 µM. "Selectively binds" or "specifically binds" means at times that an antibody binds to a protein at times with a $K_D$ of at least about 0.1 µM or better, and at other times at least about 0.01 µM or better. Because of the sequence identity between homologous proteins in different species, specific binding can include an antibody that recognizes a cancer stem cell marker protein in more than one species.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an antibody) or nucleic acid of the present disclosure that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immunoglobulin proteins with different antigen binding specificity. It can also mean that the nucleic acid or protein is in some embodiments at least 80% pure, in some embodiments at least 85% pure, in some embodiments at least 90% pure, in some embodiments at least 95% pure, and in some embodiments at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell", "tumor stem cell", or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. Solid tumor stem cells differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004, 528 proposes that such a model can be used to enhance the diagnosis of cancer. The solid tumor stem cell model is fundamentally different from the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while solid tumor stem cells are cancer cells that may themselves contain the mutations that are responsible for tumorigenesis starting at the pre-cancerous stage through later stage cancer. That is, solid tumor stem cells ("cancer stem cells") would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment) where they still form new tumors distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms "cancer cell", "tumor cell" and grammatical equivalents refer to the total population of cells derived from a tumor or a pre-cancerous lesion including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable vehicle" refers to a diluent, adjuvant, excipient, or carrier with which at least one antibody of the present disclosure is administered.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

As used herein, "providing a diagnosis" or "diagnostic information" refers to any information, including for example the presence of cancer stem cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information, including for example the presence of cancer stem cells in a subject's tumor, regarding the impact of the presence of cancer (e.g., as determined by the diagnostic methods of the present invention) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; or some combination of effects.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA. including, but not limited to, 4 acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl 2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2 thiouracil, 2-thiouracil, 4-thiouracil, 5-methyluracil, N-uracil 5-oxyacetic acid methylester, uracil 5-oxyacetic acid, pseudouracil, queosine, 2-thiocytosine, and 2,6-diaminopurine.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

"Ligation" refers to the process of forming phosphodiester bonds between two double stranded nucleic acid fragments. Unless otherwise provided, ligation can be accomplished using known buffers and conditions with 10 units to T4 DNA ligase ("ligase") per 0.5 ug of approximately equimolar amounts of the DNA fragments to be ligated. Ligation of nucleic acid can serve to link two proteins together in-frame to produce a single protein, or fusion protein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

In some embodiments, two nucleic acids or polypeptides of the invention are substantially identical, meaning they have at least 70%, at least 75%, preferably at least 80%, more preferably at least 85%, more preferably at least 90%, and in some embodiments at least 95%, 96%, 97%, 98%, 99% nucleotide or amino acid residue identity, when compared and aligned for maximum correspondence, as measured using a sequence comparison algorithm or by visual inspection. Preferably, identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

The term "epitope tagged" as used herein refers to a chimeric polypeptide comprising a cancer stem cell marker protein, or a domain sequence or portion thereof, fused to an "epitope tag". The epitope tag polypeptide comprises enough amino acid residues to provide an epitope for recognition by an antibody, yet is short enough such that it does not interfere with the activity of the cancer stem cell marker protein. Suitable epitope tags generally have at least six amino acid residues, usually between about 8 to about 50 amino acid residues, and at times between about 10 to about 20 residues. Commonly used epitope tags include Fc, HA, His, and FLAG tags.

The present invention provides compositions and methods for studying, diagnosing, characterizing, and treating cancer. In particular, the present invention provides antibodies against solid tumor stem cell markers and methods of using these antibodies to inhibit tumor growth and treat cancer in human patients. In certain embodiments, antibodies of the present invention include antagonist antibodies that specifically bind to a cancer stem cell marker protein and interfere with, for example, ligand binding, receptor dimerization, expression of a cancer stem cell marker protein, and/or signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, internalization and/or recognized by the immune system. In certain embodiments, the antibodies specifically recognize more than one solid tumor tem cells marker protein.

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of hematopoietic stem cells (HSC) and was established experimentally in acute myelogenous leukemia (AML) (Park et al., 1971, *J. Natl. Cancer Inst.* 46:411-22; Lapidot et al., 1994, *Nature* 367:645-8; Bonnet & Dick, 1997, *Nat. Med.* 3:730-7; Hope et al., 2004, *Nat. Immunol.* 5:738-43). Stem cells from solid tumors have more recently been isolated based on their expression of a unique pattern of cell-surface receptors and on the assessment of their properties of self-renewal and proliferation in culture and in xenograft animal models. An ESA+ CD44+ CD24−/low Lineage-population greater than 50-fold enriched for the ability to form tumors relative to unfractionated tumor cells was discovered (Al-Hajj et al., 2003, *Proc. Nat'l. Acad. Sci.* 100:3983-8). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal breast epithelium, using microarray analysis. The present invention employs the knowledge of these identified cancer stem cell markers to diagnosis and treat cancer.

The cancer stem cell marker of the present invention relates to the human MET Receptor (SEQ ID NOs: 26 and 27). MET is a receptor tyrosine kinase which has mitogenic and morphogenic activities that are activated by the mesenchyme-derived pleiotrophic factor, hepatocyte growth factor (HGF) (SEQ ID NOs: 28 and 29). Aberrant HGF and MET expression are frequently observed in a variety of tumors, see, e.g., Maulik et al., Cytokine & Growth Factor Reviews (2002), 13:41-59; Danilkovitch-Miagkova & Zbar, J. Clin. Invest. (2002), 109(7):863-867, and regulation of the HGF/c-Met signaling pathway is implicated in tumor progression and metastasis. See Trusolino & Comoglio, Nature Rev. (2002), 2:289-300.

HGF/MET signaling regulates a diverse array of biological processes, including cell scattering, proliferation, and survival. Signaling is essential for normal embryonic development especially in migration of muscle progenitor cells and development of the liver and nervous system (Bladt et al., 1995; Hamanoue et al., 1996; Maina et al., 1996; Schmidt et al., 1995; Uehara et al., 1995). Developmental phenotypes of Met and HGF knockout mice are very similar suggesting that HGF is the cognate ligand for the MET receptor (Schmidt et al., 1995; Uehara et al., 1995). HGF-Met also plays a role in liver regeneration, angiogenesis, and wound healing (Bussolino et al., 1992; Matsumoto & Nakamura, 1993; Nusrat et al., 1994). Upon HGF binding, activation of MET leads to tyrosine phosphorylation and downstream signaling through Gab 1 and Grb2/Sos mediated P13-kinase and Ras/MAPK activation respectively, which drives cell motility and proliferation (Furge et al., 2000; Hartmann et al., 1994; Ponzetto et al., 1996; Royal and Park, 1995).

Met was shown to be transforming in a carcinogen-treated osteosarcoma cell line (Cooper et al., 1984; Park et al., 1986). MET overexpression or gene-amplification has been observed in a variety of human cancers. For example, MET protein is overexpressed at least 5-fold in colorectal cancers and reported to be gene-amplified in liver metastasis (Di Renzo et al., 1995; Liu et al., 1992). MET protein is also reported to be overexpressed in oral squamous cell carcinoma, hepatocellular carcinoma, renal cell carcinoma, breast carcinoma, and lung carcinoma (Jin et al., 1997; Morello et al., 2001; Natali et al., 1996; Olivero et al., 1996; Suzuki et al., 1994). In addition, overexpression of Met mRNA has been observed in hepatocellular carcinoma, gastric carcinoma, and colorectal carcinoma (Boix et al., 1994; Kuniyasu et al., 1993; Liu et al., 1992).

A number of mutations in the kinase domain of MET have been found in renal papillary, carcinoma which leads to constitutive receptor activation (Olivero et al., 1999; Schmidt et al., 1997; Schmidt et al., 1999). These activating mutations confer constitutive MET tyrosine phosphorylation and result in MAPK activation, focus formation, and tumorigenesis (Jeffers et al., 1997). In addition, these mutations enhance cell motility and invasion (Giordano et al., 2000; Lorenzato et al., 2002). HGF-dependent MET activation in transformed cells mediates increased motility, scattering, and migration which eventually leads to invasive tumor growth and metastasis (Jeffers et al., 1996; Meiners et al., 1998).

MET has been shown to interact with other proteins that drive receptor activation, transformation, and invasion. In neoplastic cells, MET is reported to interact with alpha6beta4 integrin, a receptor for extracellular matrix (ECM) components such as laminins, to promote HGF-dependent invasive growth (Trusolino et al., 2001). In addition, the extracellular domain of MET has been shown to interact with a member of the semaphorin family, plexin B1, and to enhance invasive growth (Giordano et al., 2002). Furthermore, CD44v6, which has been implicated in tumorigenesis and metastasis, is also reported to form a complex with MET and HGF and result in MET receptor activation (Orian-Rousseau et al., 2002).

The extracellular domain structure of MET suggests it shares homology with the semaphorins and plexins: the N-terminus of MET contains a Sema domain of approximately 500 amino acids that is conserved in all semaphorins and plexins. The MET Sema domain is sufficient for HGF and heparin binding, (Gherardi et al., 2003), and is necessary for receptor dimerization and activation. (Cancer Cell (2004), 6:61-73).

Numerous molecules targeted at the HGF/MET pathway have been reported. These molecules include antibodies such as those described in U.S. Pat. Nos. 5,686,292; 6,214,344; 6,468,529; 5,233,960; and 6,134,104. A divalent antibody 5D5, which inhibits HGF binding to MET, is reported to be a potent MET activator, while a monovalent 5D5 antibody is a MET antagonist. (Schwall et al., AACR Meeting Abstract, 2004). The identification of MET antagonists suitable for development as therapeutic agents remains a continual challenge.

As described herein, the identification of MET expression in cancer stem cells suggested targeting MET to eliminate not only the majority of non-tumorigenic cancer cells, but also the tumorigenic cells responsible for the formation and reoccurrence of solid tumors. Thus, the present invention provides a cancer stem cell marker, the expression of which can be analyzed to diagnosis or monitor a disease associated with cancer and to provide therapeutics for the treatment of cancer.

In certain embodiments, antibodies against the cancer stem cell marker MET are provided. In the context of the present invention, a suitable antibody is an agent that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; activate a cancer stem cell signal transduction pathway by, for example, acting as a ligand or promoting the binding of an endogenous ligand; or bind to a cancer stem cell marker and inhibit tumor cell proliferation.

In certain embodiments, a combination of at least two different antibodies are administered to interfere with MET receptor signaling. Combinations of antibodies that bind to different epitopes synergistically block MET receptor functioning. The synergistic activity results from one antibody facilitating the binding of the second antibody to the MET receptor. In certain embodiments, the first antibody causes a change in the conformation of the antigen thereby giving the second antibody greater access to bind its correlate epitope.

In certain embodiments, antibodies against a cancer stem cell marker act extracellularly to modulate the function of a cancer stem cell marker protein. In some embodiments, extracellular binding of an antibody against a cancer stem cell marker can inhibit the signaling of a cancer stem cell marker protein by, for example, inhibiting intrinsic activation (e.g. kinase activity) of a cancer stem cell marker and/or by sterically inhibiting the interaction, for example, of a cancer stem cell marker with its ligand, with its receptor, with a co-receptor, or with the extracellular matrix. In some embodiments, extracellular binding of an antibody against a cancer stem cell marker can down-regulate cell-surface expression of a cancer stem cell marker such as, for example, by internalization of a cancer stem cell marker protein or decreasing cell surface trafficking of a cancer stem cell marker. In some embodiments, extracellular binding of an antibody against a cancer stem cell marker can promote the signaling of a cancer stem cell marker protein by, for example, acting as a decoy ligand or increasing ligand binding.

In certain embodiments, antibodies against a cancer stem cell marker bind to a cancer stem cell marker protein and have one or more of the following effects: inhibit proliferation of tumor cells, trigger cell death of tumor cells, or prevent metastasis of tumor cells. In certain embodiments, antibodies against a cancer stem cell marker trigger cell death via a conjugated toxin, chemotherapeutic agent, radioisotope, or other such agent. For example, an antibody against a cancer stem cell marker is conjugated to a toxin that is activated in tumor cells expressing the cancer stem cell marker by protein internalization.

In certain embodiments, antibodies against a cancer stem cell marker mediate cell death of a cell expressing the cancer stem cell marker protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophiles, for example, have Fc receptors and can mediate cytolysis (Dillman, 1994, *J. Clin. Oncol.* 12:1497).

In certain embodiments, antibodies against a cancer stem cell marker trigger cell death of a cell expressing a cancer stem cell marker protein by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a cancer stem cell to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, antibodies against a cancer stem cell marker can trigger cell death inhibiting angiogenesis. Angiogenesis is the process by which new blood vessels form from pre-existing vessels and is a fundamental process required for normal growth, for example, during embryonic development, wound healing, and in response to ovulation. Solid tumor growth larger than 1-2 $mm^2$ also requires angiogenesis to supply nutrients and oxygen without which tumor cells die. In certain embodiments, an antibody against a cancer stem cell marker targets vascular cells that express the cancer stem cell marker including, for example, endothelial cells, smooth muscle cells, or components of the extracellular matrix required for vascular assembly. In certain embodiments, an antibody against a cancer stem cell marker inhibits growth factor signaling required by vascular cell recruitment, assembly, maintenance, or survival.

The antibodies against a cancer stem cell marker find use in the diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. In addition, individual cells from a sample can be isolated, and protein expression detected on fixed or live cells by FACS analysis. In certain embodiments, antibodies can be used on protein arrays to detect expression of a cancer stem cell marker, for example, on tumor cells, in cell lysates, or in other protein samples. In certain embodiments, the antibodies of the present invention are used to inhibit the growth of tumor cells by contacting the antibodies with tumor cells in in vitro cell based assays, in vivo animal models, etc. In certain embodiments, the antibodies are used to treat cancer in a patient by administering a therapeutically effective amount of an antibody against a cancer stem cell marker.

The antibodies of the invention can be prepared by any conventional means known in the art. For example, polyclonal antibodies can be prepared by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) *Nature* 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, *Nature,* 348:552-554; Clackson et al., 1991, *Nature,* 352:624-628; and Marks et al., 1991, *J. Mol. Biol.,* 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the present invention, the monoclonal antibody against the cancer stem cell marker is a humanized antibody. Humanized antibodies are antibodies that contain minimal sequences from non-human (e.g rodent) antibodies within the antigen determination or hypervariable region that comprise the three complementary determination regions (CDRs) within each antibody chain. Such antibodies are used therapeutically to reduce antigenicity and HAMA (human anti-mouse antibody) responses when administered to a human subject. In practice, humanized antibodies are typically human antibodies with minimum to virtually no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDRs of a human antibody with those of a non-human antibody (e.g. mouse, rat, rabbit, hamster, etc.) having the desired specificity, affinity, and capability following the methods of Jones et al., 1986, Nature, 321:522-525; Riechmann et al., 1988, Nature, 332:323-327; Verhoeyen et al., 1988, Science, 239:1534-1536. The humanized antibody can be further modified by the substitution of additional residue either in the variable human framework region and/or within the replaced non-human residues to refine and optimize antibody specificity, affinity, and/or capability.

The choice of human heavy and/or light chain variable domains to be used in making humanized antibodies can be important for reducing antigenicity. According to the "best-fit" method, the sequence of the variable domain of a rodent antibody is screened against the entire library of known human variable-domain amino acid sequences. Thus in certain embodiments, the human amino acid sequence which is most homologous to that of the rodent antibody from which the CDRs are taken is used as the human framework region (FR) for the humanized antibody (Sims et al., 1993, J. Immunol., 151: 2296; Chothia et al., 1987, J. Mol. Biol., 196: 901). Another method uses a particular FR derived from the consensus sequence of all human antibodies of a particular subgroup of light or heavy chains and can be used for several difference humanized antibodies (Carter et al., 1992, PNAS, 89; 4285; Presta et al., 1993, J. Immunol., 151: 2623). In certain embodiments, a combination of methods is used to pick the human variable FR to use in generation of humanized antibodies.

It is further understood that antibodies (e.g. rodent) to be humanized must retain high affinity for the antigen as well as other favorable biological properties. To achieve this goal, humanized antibodies can be prepared by a process of analysis of the parental sequence from the rodent antibody to be humanized and the various candidate humanizing sequences. Three-dimensional immunoglobulin models are available and familiar to those skilled in the art. Computer programs can be used to illustrate and display probable three-dimensional conformational structures of selected candidate antibody sequences. Use of such models permits analysis of the likely role of the residues in the function of the antibody to be humanized, i.e., the analysis of residues that influence the ability of the candidate antibody to bind its antigen. In this way, FR residues can be selected and combined from the parental antibody to the recipient humanized antibody so that the desired antibody characteristics are achieved. In general, the residues in the CDRs of the antigen determination region (or hypervariable region) are retained from the parental antibody (e.g. the rodent antibody with the desired antigen binding properties) in the humanized antibody for antigen binding. In certain embodiments, at least one additional residue within the variable FR is retained from the parental antibody in the humanized antibody. In certain embodiments, up to six additional residues within the variable FR are retained from the parental antibody in the humanized antibody.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest, U.S. Department of Health and Human Services, 1987, 1991. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. In some embodiments, after alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

In addition to humanized antibodies, fully human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nat. Biotech., 14:309-314; Sheets et al., 1998, Proc. Nat'l. Acad. Sci., 95:6157-6162; Hoogenboom and Winter, 1991, J. Mol. Biol., 227:381; Marks et al., 1991, J. Mol. Biol., 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a cancer stem cell marker. Bispecific antibodies are antibodies that are capable of specifically recognizing and binding at least two different epitopes (See, e.g., Wu et al., *Simultaneous Targeting of Multiple Disease Mediators by a Dual-Variable-Domain Immunoglobulin*, Nature Biotech., 25(11):1290-97). The different epitopes can either be within the same molecule (e.g. the same cancer stem cell marker polypeptide) or on different molecules such that both, for example, can specifically recognize and bind a cancer stem cell marker as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148:1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., *J. Immunol.* 147:60 (1991))

In certain embodiments are provided an antibody fragment to, for example, increase tumor penetration. Various techniques are known for the production of antibody fragments: Traditionally, these fragments are derived via proteolytic digestion of intact antibodies (for example Morimoto et al., 1993, Journal of Biochemical and Biophysical Methods 24:107-117; Brennan et al., 1985, *Science*, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to a polypeptide of the invention (see U.S. Pat. No. 4,946,778). In addition, methods can be adapted for the construction of Fab expression libraries (Huse, et al., *Science* 246:1275-1281 (1989)) to allow rapid and effective identification of monoclonal Fab fragments with the desired specificity for the MET receptor, or derivatives, fragments, or homologs thereof. Antibody fragments that contain the idiotypes to a polypeptide of the invention may be produced by techniques in the art including, but not limited to: (a) an F(ab')2 fragment produced by pepsin digestion of an antibody molecule; (b) an Fab fragment generated by reducing the disulfide bridges of an F(ab')2 fragment, (c) an Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of human MET. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

The variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed (ΔCH2 constructs). In some embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques well within the purview of the skilled artisan.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, any spacer added to the construct be relatively non-immunogenic or, even omitted altogether if the desired biochemical qualities of the modified antibodies may be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. In some embodiments, the antibodies can be conjugated to radioisotopes, such as $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$ using anyone of a number of well known chelators or direct labeling. In other embodiments, the disclosed compositions can comprise antibodies coupled to drugs, prodrugs or lymphokines such as interferon. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used. In some embodiments, the modified antibodies can be complexed with other immunologically active ligands (e.g. antibodies or fragments thereof) wherein the resulting molecule binds to both the neoplastic cell and an effector cell such as a T cell.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

The antibodies of the present invention can be assayed for immunospecific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, the immunospecificity of an antibody against a cancer stem cell marker is determined using ELISA. An ELISA assay comprises preparing antigen, coating wells of a 96 well microtiter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. In some embodiments, the antibody against a cancer stem cell marker is not conjugated to a detectable compound, but instead a second conjugated antibody that recognizes the antibody against a cancer stem cell marker is added to the well. In some embodiments, instead of coating the well with the antigen, the antibody against a cancer stem cell marker can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an antibody to a cancer stem cell marker antigen and the off-rate of an antibody-antigen interaction can be determined by competitive binding assays. One example of a competitive binding assay is a radioimmunoassay comprising the incubation of labeled antigen (e.g. $^3H$ or $^{125}I$), or fragment or variant thereof, with the antibody of interest in the presence of increasing amounts of unlabeled antigen followed by the detection of the antibody bound to the labeled antigen. The affinity of the antibody against a cancer stem cell marker and the binding off-rates can be determined from the data by scatchard plot analysis. In some embodiments, BIAcore kinetic analysis is used to determine the binding on and off rates of antibodies against a cancer stem cell marker. BIAcore kinetic analysis comprises analyzing the binding and dissociation of antibodies from chips with immobilized cancer stem cell marker antigens on their surface.

In certain embodiments, the present invention provides antibodies that are substantially identical to the antibody sequences of the invention, meaning they have at least 70%, at least 75%, preferably at least 80%, more preferably at least 85%, more preferably at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, the invention provides an antibody that specifically binds a human MET receptor, comprising (a) a heavy chain variable region comprising an amino acid sequence at least about 90% identical to SEQ ID NO:2 and a light chain variable region comprising an amino acid sequence that is at least about 90% identical to SEQ ID NO:7; and/or (b) a heavy chain variable region comprising an amino acid sequence at least about 90% identical to SEQ ID NO:12 and a light chain variable region comprising an amino acid sequence that is at least about 90% identical to SEQ ID NO:17 or to SEQ ID NO:22.

Example 1 below describes the production of exemplary human anti-MET antibodies which specifically bind to the cancer stem cell marker MET and inhibit HGF binding and downstream MET signaling. In certain embodiments, the invention provides an isolated antibody that specifically binds to a human MET Receptor, wherein the antibody comprises a heavy chain variable region comprising CDR sequences SEQ ID NO: 3, SEQ ID NO: 4, and SEQ ID NO: 5. In certain embodiments, the isolated MET Receptor antibody further comprising a light chain variable region comprising CDR sequences SEQ ID NO: 8, SEQ ID NO: 9, and SEQ ID NO: 10. In certain embodiments, the isolated MET Receptor antibody comprises a heavy chain variable region that comprises an amino acid sequence at least 95% identical to SEQ ID NO: 2. In certain embodiments, the isolated MET Receptor antibody comprises a heavy chain variable region that comprises an amino acid sequence at least 99% identical to SEQ ID NO: 2. In certain embodiments, the isolated MET Receptor antibody comprises a light chain variable region that comprises an amino acid sequence at least 95% identical to SEQ ID NO: 7. In certain embodiments, the isolated MET Receptor antibody comprises a light chain variable region that comprises an amino acid sequence at least 99% identical to SEQ ID NO: 7. In certain embodiments, the isolated MET Receptor antibody comprises heavy chain SEQ ID NO: 2 and light chain SEQ ID NO: 7. In certain embodiments, the isolated MET Receptor antibody is a human antibody. In certain embodiments, the human MET Receptor antibody is a human IgG antibody. In certain embodiments, the human IgG antibody is 13-MET IgG, the IgG encoded by the plasmid DNA deposited with the American Type Culture Collection (ATCC), 10801 University Boulevard, Manassas, Va., USA, on Apr. 10, 2008, under the provisions of the Budapest Treaty, and having ATCC deposit no. PTA-9148.

In certain embodiments, the invention provides an isolated antibody that competes with antibody 13-MET for specific binding to a human MET Receptor, wherein the 13-MET antibody comprises: (i) a heavy chain variable region comprising SEQ ID NO: 2; and (ii) a light chain variable region comprising SEQ ID NO: 7. In certain embodiments, the invention provides an isolated antibody that competes with antibody 13-MET for specific binding to a human MET Receptor, wherein the 13-MET antibody comprise the antibody encoded by the plasmid DNA deposited with ATCC on Apr. 10, 2008 and having ATCC deposit no. PTA-9148.

In certain embodiments, the present invention provides an isolated antibody that specifically binds to a human MET Receptor wherein the antibody comprises a heavy chain variable region comprising CDR sequences SEQ ID NO: 13, SEQ ID NO: 14, and SEQ ID NO: 15. In certain embodiments, the isolated MET Receptor antibody further comprises a light chain variable region comprising CDR sequences SEQ ID NO: 18, SEQ ID NO: 19, and SEQ ID NO: 20. In certain embodiments, the isolated MET Receptor antibody further comprises a light chain variable region comprising CDR sequences SEQ ID NO:23, SEQ ID NO:24, and SEQ ID NO:25. In certain embodiments, the isolated MET Receptor antibody comprises a heavy chain variable region comprising an amino acid sequence at least 95% identical to SEQ ID NO: 12. In certain embodiments, the isolated MET Receptor antibody comprises a heavy chain variable region comprising an amino acid sequence at least 99% identical to SEQ ID NO: 12. In certain embodiments, the isolated MET Receptor antibody comprises a light chain variable region comprising an amino acid sequence at least 95% identical to SEQ ID NO: 17. In certain embodiments, the isolated MET Receptor antibody comprises a light chain variable region comprising an amino acid sequence at least 99% identical to SEQ ID NO: 17. In certain embodiments, the isolated MET Receptor antibody comprises a light chain variable region comprising an amino acid sequence at least 95% identical to SEQ ID NO: 22. In certain embodiments, the isolated MET Receptor antibody comprises a light chain variable region comprising an amino acid sequence at least 99% identical to SEQ ID NO: 22. In certain embodiments, the isolated MET Receptor antibody comprises heavy chain SEQ ID NO: 12 and light chain SEQ ID NO: 17. In certain embodiments, the isolated MET Receptor antibody is a human antibody. In certain embodiments, the human MET Receptor antibody is a human IgG antibody. In certain embodiments, human IgG antibody is 28-MET IgG, the antibody encoded by the plasmid DNA deposited with ATCC on Apr. 10, 2008 under the provisions of the Budapest Treaty, and having ATCC deposit no. PTA-9149.

In certain embodiments, the present invention provides an isolated antibody that competes with antibody 28-MET for specific binding to a human MET Receptor, wherein the 28-MET antibody comprises: (i) a heavy chain variable region comprising SEQ ID NO: 12; and (ii) a light chain variable region comprising SEQ ID NO: 17. In certain embodiments, the present invention provides an isolated antibody that competes with antibody 21-MET for specific binding to a human MET Receptor, wherein the 21-MET antibody comprises: (i) a heavy chain variable region comprising SEQ ID NO: 12; and (ii) a light chain variable region comprising SEQ ID NO: 22. In certain embodiments, the present invention provides an isolated antibody that competes with antibody 28-MET for specific binding to a human MET Receptor, wherein the 28-MET antibody comprises the antibody encoded by the plasmid DNA deposited with ATCC on Apr. 10, 2008 and having ATCC deposit no. PTA-9149.

In certain embodiments, the present invention provides a method of treating cancer in a patient comprising administering to the patient a therapeutically effective amount of an antibody which specifically binds to a human MET Receptor, wherein the antibody comprises a heavy chain variable region comprising CDR sequences SEQ ID NO: 3, SEQ ID NO: 4, and SEQ ID NO: 5. In certain embodiments, the antibody further comprises a light chain variable region comprising CDR sequences SEQ ID NO: 8, SEQ ID NO: 9, and SEQ ID NO: 10. In certain embodiments, the antibody comprises SEQ ID NO: 2 and SEQ ID NO: 7. In certain embodiments, the isolated MET Receptor antibody is a human antibody. In certain embodiments, the human MET Receptor antibody is a human IgG antibody. In certain embodiments, human IgG antibody is 13-MET IgG deposited with ATCC on Apr. 10, 2008 and having ATCC deposit no. PTA-9148. In certain embodiments, the present invention provides a method of treating cancer in a patient comprising administering to the patient a therapeutically effective amount of an antibody that competes with antibody 13-MET for specific binding to a human MET Receptor, wherein the 13-MET antibody comprises: (i) a heavy chain variable region comprising SEQ ID NO: 2; and (ii) a light chain variable region comprising SEQ ID NO: 7. In certain embodiments, the present invention provides a method of treating cancer in a patient comprising administering to the patient a therapeutically effective amount of an antibody that competes with antibody 13-MET for specific binding to a human MET Receptor, wherein the 13-MET antibody comprises the antibody encoded by the plasmid DNA deposited with ATCC on Apr. 10, 2008 and having ATCC deposit no. PTA-9148.

In certain embodiments, the present invention provides a method of treating cancer in a patient comprising administering to the patient a therapeutically effective amount of an antibody which specifically binds to a human MET Receptor, wherein the antibody comprises a heavy chain variable region comprising CDR sequences SEQ ID NO: 13, SEQ ID NO: 14, and SEQ ID NO: 15. In certain embodiments, the antibody further comprises a light chain variable region comprising CDR sequences selected from the group consisting of: SEQ ID NO: 18, SEQ ID NO: 19, SEQ ID NO: 20, SEQ ID NO:23, SEQ ID NO: 24, and SEQ ID NO: 25. In certain embodiments, the antibody comprises SEQ ID NO: 12 and SEQ ID NO: 17. In certain embodiments, the antibody comprises SEQ ID NO: 12 and SEQ ID NO: 22. In certain embodiments, the isolated MET Receptor antibody is a human antibody. In certain embodiments, the human MET Receptor antibody is a human IgG antibody. In certain embodiments, human IgG antibody is 28-MET IgG, the antibody encoded by the plasmid DNA deposited with ATCC on Apr. 10, 2008 and having ATCC deposit no. PTA-9149.

In certain embodiments, the present invention provides a method of treating cancer in a patient comprising administering to the patient a therapeutically effective amount of an antibody that competes with antibody 13-MET for specific binding to a human MET Receptor, wherein the 13-MET antibody comprises: (i) a heavy chain variable region comprising SEQ ID NO: 2; and (ii) a light chain variable region comprising SEQ ID NO: 7. In certain embodiments, the present invention provides a method of treating cancer in a patient comprising administering to the patient a therapeutically effective amount of an antibody that competes with antibody 13-MET for specific binding to a human MET Receptor, wherein the 28-MET antibody comprises the antibody encoded by the plasmid DNA deposited with ATCC on Apr. 10, 2008 and having ATCC deposit no. PTA-9149.

In certain embodiments, the present invention provides a method of treating cancer in a patient comprising administering to the patient a therapeutically effective amount of an antibody that competes with antibody 21-MET for specific binding to a human MET Receptor, wherein the 21-MET antibody comprises: (i) a heavy chain variable region comprising SEQ ID NO: 12; and (ii) a light chain variable region comprising SEQ ID NO: 22.

In certain embodiments, the present invention provides a method of treating cancer in a patient comprising administering to the patient a therapeutically effective amount of an antibody that specifically binds a human MET receptor, comprising (a) a heavy chain variable region comprising an amino acid sequence at least about 90% identical to SEQ ID NO:2 and a light chain variable region comprising an amino acid sequence that is at least about 90% identical to SEQ ID NO:7; and/or (b) a heavy chain variable region comprising an amino acid sequence at least about 90% identical to SEQ ID NO:12 and a light chain variable region comprising an amino acid sequence that is at least about 90% identical to SEQ ID NO:17 or to SEQ ID NO:22.

In certain additional embodiments, the invention provides a bispecific antibody that specifically binds a first and second epitope on the extracellular domain of a human Met receptor and inhibits binding of HGF to the receptor, wherein the first epitope is in the SEMA domain and the second epitope is a conformational epitope that does not overlap with the first epitope. In certain embodiments, binding to the SEMA domain directly blocks HGF binding to the MET receptor. In certain embodiments, binding to the SEMA domain increases the avidity of the bispecific antibody for binding to the other epitope. Methods of using the antibody to inhibit signaling by a human MET receptor on a cell, comprising contacting the cell with the bispecific antibody are further provided. Methods of inhibiting growth of a tumor in a patient and methods of treating cancer, comprising administering to the patient a therapeutically effective amount of the antibody is also provided.

The invention further provides, in some embodiments, methods of treating cancer comprising administering (a) a first antibody that binds to a first epitope in the SEMA domain of a human Met receptor, and (b) a second antibody that binds to a second, conformational epitope on the extracellular domain of the human Met receptor. In certain embodiments, the combination of the first and second antibody synergistically inhibits HGF binding to the Met receptor. In certain embodiments, binding of the first antibody to the SEMA domain directly blocks HGF binding to the MET receptor. In certain embodiments, binding of the first antibody to the SEMA domain increases the avidity of the second antibody for the MET receptor.

In certain embodiments, the present invention provides a method of treating cancer in a patient comprising administering to the patient a therapeutically effective amount of a combination of antibodies that specifically bind different epitopes on the same antigen. In certain embodiments, the present invention provides a method of inhibiting receptor functioning comprising administering to the patient a therapeutically effective amount of a combination of antibodies that specifically bind different epitopes on the same antigen. In certain embodiments, the different epitopes are on the extracellular domain of the receptor. In some embodiments, the epitopes are non-overlapping. In certain embodiments, the receptor is a receptor tyrosine kinase. In certain embodiments the receptor is a human MET receptor. As demonstrated herein, combinations of antibodies act synergistically by increasing the availability of epitopes for antibody binding. The proper ratio of the antibody combination can readily be determined by one of ordinary skill in the art. In certain embodiments, the first antibody and the second antibody are administered at a ratio of 1:X, wherein X is any integer. In certain embodiments, X is at least about 1, at least about 2, at least about 3, at least about 4, at least about 5, at least about 6, at least about 7, at least about 8, at least about 9, at least about 10, at least about 15, at least about 20, at least about 25, or at least about 50.

In certain embodiments, the invention provides a bispecific antibody that specifically binds to two different epitopes on the extracellular domain of a receptor, such as a receptor tyrosine kinase. In certain embodiments, the receptor is a human MET receptor. In certain embodiments, the two different epitopes are non-overlapping. In certain embodiments, the bispecific antibody inhibits the signaling or other activity of the receptor.

In certain embodiments, the present invention provides a method of treating cancer in a patient comprising administering to the patient a therapeutically effective amount of a combination of antibodies which specifically binds to a human MET Receptor, wherein the combination of antibodies comprises: (i) a first antibody comprising: (a) a heavy chain variable region comprising CDR sequences SEQ ID NO: 3, SEQ ID NO: 4, and SEQ ID NO: 5; and (b) a light chain variable region comprising CDR sequences SEQ ID NO: 8, SEQ ID NO: 9, and SEQ ID NO: 10; and (ii) a second antibody comprising (a) a heavy chain variable region comprising CDR sequences SEQ ID NO: 13, SEQ ID NO: 14, and SEQ ID NO: 15; and (b) a light chain variable region comprising CDR sequences selected from the group consisting of: SEQ ID NO: 18, SEQ ID NO: 19, SEQ ID NO: 20, SEQ ID NO:23, SEQ ID NO:24, and SEQ ID NO:25. In certain embodiments, the first antibody comprises SEQ ID NO: 2 and SEQ ID NO: 7 and the second antibody comprises SEQ ID NO: 12 and SEQ ID NO: 17. In another embodiment, the first antibody comprises SEQ ID NO: 2 and SEQ ID NO: 7 and the second antibody comprises SEQ ID NO:12 and SEQ ID NO:22. In certain embodiments, the first antibody and the second antibody are human antibodies. In certain embodiment, the first human antibody and the second human antibody are human IgG antibodies. In certain embodiments, the first antibody and the second antibody are administered at a ratio of 1:1. In certain embodiments, the first antibody and the second antibody are administered at a ratio of 1:5. In certain embodiments, the first human antibody is the 13-MET. IgG antibody encoded by the plasmid deposited with ATCC on Apr. 10, 2008 and having ATCC deposit no. PTA-9148 and the second human antibody is the 28-MET IgG antibody encoded by the plasmid DNA deposited with ATCC on Apr. 10, 2008 and having ATCC deposit no. PTA-9149. In certain embodiments, the first antibody and the second antibody are administered at a ratio of 1:1. In certain embodiments, the 13-MET and 28-MET antibodies are administered at a ratio of 1:8. In certain embodiments, the 9-MET and 19-MET antibodies are administered at a ratio of 1:8. In certain embodiments, the first antibody and the second antibody are administered to the patient sequentially. In certain embodiments, the first antibody and the second antibody are administered to the patient in separate compositions.

In certain embodiments, the present invention provides a bispecific antibody that specifically binds to a human MET Receptor, the antibody comprising: (i) a first heavy chain variable region comprising CDR sequences SEQ ID NO: 3, SEQ ID NO: 4, and SEQ ID NO: 5; and/or (ii) a first light chain variable region comprising CDR sequences SEQ ID NO: 8, SEQ ID NO: 9, and SEQ ID NO: 10. In certain embodiments, the bispecific antibody further comprises: (iii) a second heavy chain variable region comprising CDR sequences SEQ ID NO: 13, SEQ ID NO: 14, and SEQ ID NO: 15; and/or (iv) a second light chain variable region comprising CDR sequences selected from the group consisting of SEQ ID NO: 18, SEQ ID NO: 19, SEQ ID NO: 20, SEQ ID NO:23, SEQ ID NO:24, and SEQ ID NO:25. In certain embodiments, the second light chain variable region comprises CDR sequences SEQ ID NO: 18, SEQ ID NO: 19, and SEQ ID NO: 20. In certain alternative embodiments, the second light chain variable region comprises CDR sequences SEQ ID NO:23, SEQ ID NO:24, and SEQ ID NO:25.

In certain embodiments, the present invention provides a bispecific antibody that specifically binds to a human MET Receptor, the antibody comprising: (i) a first heavy chain variable region comprising CDR sequences SEQ ID NO: 13, SEQ ID NO: 14, and SEQ ID NO: 15; and/or (ii) a first light chain variable region comprising CDR sequences selected from the group consisting of: SEQ ID NO: 18, SEQ ID NO: 19, SEQ ID NO: 20, SEQ ID NO:23, SEQ ID NO:24, and SEQ ID NO:25. In certain embodiments, the first light chain variable region comprises CDR sequences SEQ ID NO: 18, SEQ ID NO: 19, and SEQ ID NO: 20. In certain alternative embodiments, the first light chain variable region comprises CDR sequences SEQ ID NO:23, SEQ ID NO:24, and SEQ ID NO:25. In certain embodiments, the bispecific antibody further comprises: (iii) a second heavy chain variable region comprising CDR sequences SEQ ID NO: 3, SEQ ID NO: 4, and SEQ ID NO: 5; and (iv) a second light chain variable region comprising CDR sequences SEQ ID NO: 8, SEQ ID NO: 9, and SEQ ID NO: 10.

In certain embodiments, the invention encompasses isolated polynucleotides that encode a polypeptide comprising a human antibody, or fragment thereof, against human MET. Thus, the term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the hereinabove described polynucleotides encoding, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

In certain embodiments, the present invention provides isolated nucleic acid molecules having a nucleotide sequence at least 80% identical, at least 85% identical, at least 90% identical, at least 95% identical, and in some embodiments, at least 96%, 97%, 98% or 99% identical to a polynucleotide encoding a polypeptide comprising a humanized antibody, or fragment thereof, against human MET.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The polypeptides of the present invention can be recombinant polypeptides, natural polypeptides, or synthetic polypeptides comprising an antibody, or fragment thereof, against human MET. It will be recognized in the art that some amino acid sequences of the invention can be varied without significant effect of the structure or function of the protein. Thus, the invention further includes variations of the polypeptides which show substantial activity or which include regions of a humanized antibody, or fragment thereof, against human MET protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci.* USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovims and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a cancer stem cell marker protein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

The present invention provides methods for inhibiting the growth of tumorigenic cells expressing a cancer stem cell marker using the antibodies against a cancer stem cell marker described herein. In certain embodiments, the method of inhibiting the growth of tumorigenic cells expressing a cancer stem cell marker comprises contacting the cell with an antibody against a cancer stem cell marker in vitro. For example, an immortalized cell line or a cancer cell line that expresses a cancer stem cell marker is cultured in medium to which is added an antibody against the expressed cancer stem cell marker to inhibit cell growth. In some embodiments, tumor cells comprising tumor stem cells are isolated from a patient sample such as, for example, a tissue biopsy, pleural effusion, or blood sample and cultured in medium to which is added an antibody against a cancer stem cell marker to inhibit cell growth.

In some embodiments, the method of inhibiting the growth of tumorigenic cells expressing a cancer stem cell marker comprises contacting the cell with an antibody against a cancer stem cell marker in vivo. In certain embodiments, contacting a tumorigenic cell with an antibody against a cancer stem cell marker is undertaken in an animal model. For example, xenografts expressing a cancer stem cell marker are grown in immunocompromised mice (e.g. NOD/SCID mice) that are administered an antibody against a cancer stem cell marker to inhibit tumor growth. In some embodiments, cancer stem cells that express a cancer stem cell marker are isolated from a patient sample such as, for example, a tissue biopsy, pleural effusion, or blood sample and injected into immunocompromised mice that are then administered an antibody against the cancer stem cell marker to inhibit tumor cell growth. In some embodiments, the antibody against a cancer stem cell marker is administered at the same time or shortly after introduction of tumorigenic cells into the animal to prevent tumor growth. In some embodiments, the antibody against a cancer stem cell marker is administered as a therapeutic after the tumorigenic cells have grown to a specified size.

In certain embodiments, antibodies administered in combination act synergistically to inhibit any receptor functioning. In certain embodiments, inhibiting receptor functioning is performed in vitro. In certain embodiments, inhibiting receptor functioning is performed in vivo. In some embodiments, the antibodies are administered as a composition comprising at least two antibodies that bind to different epitopes within the same antigen. In certain embodiments, each of the antibodies binds to a separate epitope on the receptor. In certain embodiments, each of the two epitopes are on the extracellular domain of the antigen. In some other embodiments, one or more of the antibodies is a bispecific antibody that binds to two different epitopes on the same antigen. When administered in combination, the first antibody causes a change in the receptor such that the second antibody is able to have a greater effect on blocking receptor functioning. In certain embodiments, the first antibody causes a conformational change in the receptor so that the second antibody has greater access to the epitope on the receptor to which it binds. In certain embodiments, one of the antibodies stabilizes a particular conformation of the receptor upon binding to the receptor. In certain embodiments, a second antibody binds or preferentially binds to that stabilized conformation of the receptor. In certain embodiments, the avidity of the second antibody for the receptor is increased by the binding of the first antibody to the receptor.

In certain embodiments, receptor tyrosine kinase activity is blocked by administration of a combination of at least two antibodies that bind to different epitopes of the receptor tyrosine kinase (e.g., two epitopes on the extracellular domain of the receptor tyrosine kinase). In certain embodiments, the receptor tyrosine kinase is a receptor that is stimulated by dimerization. In another embodiment, human MET receptor activity is blocked by administration of a combination of at least two antibodies that bind different epitopes of the human MET receptor (e.g., different epitopes on the extracellular domain of the human MET receptor). In certain embodiments, the receptor activity that is inhibited is signaling by the receptor. In certain embodiments, one antibody competes for specific binding to a human MET receptor with (1) a first antibody comprising (a) a heavy chain variable region comprising SEQ ID NO: 2; and (b) a light chain variable region comprising SEQ ID NO: 7, and the other antibody competes for specific binding to a human MET receptor with (2) a second antibody comprising (a) a heavy chain variable region comprising SEQ ID NO: 12; and (b) a light chain variable region comprising SEQ ID NO: 17 or SEQ ID NO:22.

The present invention further provides pharmaceutical compositions comprising antibodies that target a cancer stem cell marker and a pharmaceutically acceptable excipient. In certain embodiments, the antibodies are bispecific antibodies. These bispecific antibodies may bind to two different epitopes on the extracellular domain of the same receptor. In certain embodiments the pharmaceutical composition comprises at least two antibodies and a pharmaceutically acceptable excipient. In some embodiments, each of the two antibodies specifically binds a different epitope on the extracellular domain of the same receptor tyrosine kinase. In certain embodiments, the receptor tyrosine kinase is human MET receptor. In some embodiments, the first antibody competes for specific binding to a human MET receptor with an antibody comprising (a) a heavy chain variable region comprising SEQ ID NO: 2; and (b) a light chain variable region comprising SEQ ID NO: 7, and (2) the second antibody competes for specific binding to a human MET receptor with an antibody comprising (a) a heavy chain variable region comprising SEQ ID NO: 12; and (b) a light chain variable region comprising SEQ ID NO: 17 or SEQ ID NO:22. These pharmaceutical compositions find use in inhibiting tumor cell growth and treating cancer in human patients.

Formulations are prepared for storage and use by combining a purified antibody of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(v nylalcohol), poly-lactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the treatment involves the combined administration of an antibody of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In other embodiments, the treatment involves the combined administration of an antibody of the present invention and radiation therapy. Treatment with the antibody can occur prior to, concurrently with, or subsequent to administration of radiation therapy. Any dosing schedules for such radiation therapy can be used as determined by the skilled practitioner.

In other embodiments, the treatment can involve the combined administration of antibodies of the present invention with other antibodies against additional tumor associated antigens including, but not limited to, antibodies that bind to the EGF receptor (EGFR) (Erbitux®), the erbB2 receptor (HER2) (Herceptin®), and vascular endothelial growth factor (VEGF) (Avastin®). Furthermore, treatment can include administration of one or more cytokines, can be accompanied by surgical removal of cancer cells or any other therapy deemed necessary by a treating physician.

For the treatment of the disease, the appropriate dosage of an antibody of the present invention depends on the type of disease to be treated, the severity and course of the disease, the responsiveness of the disease, whether the antibody is administered for therapeutic or preventative purposes, previous therapy, patient's clinical history, and so on all at the discretion of the treating physician. The antibody can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the antibodies described herein and that can be used to perform the methods described herein. In certain embodiments, a kit comprises at least one purified antibody against a cancer stem cell marker in one or more containers. In certain embodiments, a kit comprises at least two antibodies, wherein each of the two antibodies specifically binds a different epitope on the same receptor tyrosine kinase. In certain embodiments, each of the two antibodies specifically binds to the extracellular domain of the receptor tyrosine kinase. In certain embodiments, the receptor tyrosine kinase is human MET receptor. In certain embodiments, the first antibody competes for specific binding to a human MET receptor with an antibody comprising (a) a heavy chain variable region comprising SEQ ID NO: 2; and (b) a light chain variable region comprising SEQ ID NO: 7, and (2) the second antibody competes for specific binding to a human MET receptor with an antibody comprising (a) a heavy chain variable region comprising SEQ ID NO: 12; and (b) a light chain variable region comprising SEQ ID NO: 17 or SEQ ID NO:22. In some embodiments, the kits contain all of the components necessary and/or sufficient to perform a detection assay, including all controls, directions for performing assays, and any necessary software for analysis and presentation of results. One skilled in the art will readily recognize that the disclosed antibodies of the present invention can be readily incorporated into one of the established kit formats which are well known in the art.

Embodiments of the present disclosure can be further defined by reference to the following examples, which describe in detail preparation of antibodies of the present disclosure and methods for using antibodies of the present disclosure. It will be apparent to those skilled in the art that many modifications, both to materials and methods, may be practiced without departing from the scope of the present disclosure. Wherever possible, the same reference numbers will be used throughout the drawings to refer to the same or like parts. As used herein and in the appended claims, the singular forms "a," "or," and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about," unless otherwise indicated. Accordingly, the numerical parameters set forth in the specification and claims are approximations that may vary depending upon the desired properties of the present invention.

All of the various embodiments or options described herein can be combined in any and all variations.

EXAMPLES

Example 1

Production of Functional Anti-Met Antibodies

Using the Morphosys HuCAL GOLD Fab library, functional anti-Met antibodies were discovered using a series of novel selections against human cancer cell lines (GTL-16 & SNU-5) which over-express Met, and recombinant Met extracellular domain (ECD) (and isolated domains thereof). Specifically, $2 \times 10^{13}$ Fab displaying phage particles were incubated with GTL-16 ($>10^6$ cells) in round one, non-specific phage were washed off, and then specific phage were eluted with low pH. The eluted output was used to infect TG1 F+ bacteria, rescued with helper phage, and then Fab display induced with IPTG (0.25 mM).

This rescued round one output was used as the starting point for wide array of selections in rounds two, three, and four as indicated below:

| R1 | R2 | R3 | R4 |
|---|---|---|---|
| GTL-16 → | Met Fc → | GTL-16 | |
| GTL-16 → | Met Fc → | SEMA | |
| GTL-16 → | SNU-5 → | Met Fc → | Met Fc |
| GTL-16 → | Met His → | Met His | |
| GTL-16 → | SNU-5 → | Met His → | Met His |
| GTL-16 → | Met His → | GTL-16(E) → | Met His |

For selections on recombinant protein, protein was passively immobilized on polystyrene plates and blocked with milk. After washing with PBS-Tween (PBS/T), specific phage were eluted with dithiothreitol (DTT). Fab-13 was isolated from the selections 1 and 2; whereas Fab-28 was isolated from selections 3-6. In all cases, the functional Fabs were only discovered from selections initiated on cancer cell lines and were not found in selections conducted only on recombinant protein.

Two monovalent Fabs were isolated for further analysis: Fab-13 (13-MET) (R13) and Fab-28 (28-MET) (R28). The 13-MET heavy chain variable nucleotide and amino acid sequences are provided in SEQ ID NO: 1 and 2, respectively, along with the amino acid sequences of the heavy chain CDR1 (SEQ ID NO: 3); CDR2 (SEQ ID NO: 4); and CDR3 (SEQ ID NO 5). The 13-MET light chain variable nucleotide and amino acid sequences are provided in SEQ ID NO: 6 and 7, respectively, along with the amino acid sequences of the light chain CDR1 (SEQ ID NO: 8); CDR2 (SEQ ID NO: 9); and CDR3 (SEQ ID NO 10). The 28-MET heavy chain variable nucleotide and amino acid sequences are provided in SEQ ID NO: 11 and 12, respectively, along with the amino acid sequences of the heavy chain CDR1 (SEQ ID NO: 13); CDR2 (SEQ ID NO: 14); and CDR3 (SEQ ID NO 15). The 28-MET light chain variable nucleotide and amino acid sequences are provided in SEQ ID NO: 16 and 17, respectively, along with the amino acid sequences of the light chain CDR1 (SEQ ID NO: 18); CDR2 (SEQ ID NO: 19); and CDR3 (SEQ ID NO 20). Each monovalent Fab was combined with human constant regions to generated full human IgG$_1$ 13-MET and 28-MET antibodies.

Each monovalent Fab was also linked to itself via a helix-loop-helix motif to produce divalent dimer Fabs (FIG. 1A). Specifically, two 13-MET Fabs were linked to produce the dimer 9-MET, and two 28-MET Fabs were linked to produce the dimer 19-MET. Similarly, each monovalent Fab was combined to generate a human IgG1 molecule (FIG. 1A). 13-MET and 28-MET monovalent Fabs are similarly linked to produce bispecific antibodies.

The 28-MET antibody was further subjected to affinity maturation. The 21-MET antibody (R21) is an affinity matured 28-MET antibody comprising an altered light chain variable region. The 21-MET light chain variable nucleotide and amino acid sequences are provided in SEQ ID NO: 21 and 22, respectively, along with the amino acid sequences of the light chain CDR1 (SEQ ID NO: 23); CDR2 (SEQ ID NO: 24); and CDR3 (SEQ ID NO 25).

BIAcore was used to determine binding affinities, shown in Table 1 below for 13-MET and 28-MET. Fab and IgG affinities were determined using a BIAcore 2000 instrument. Briefly, MET ECD was immobilized on a CM5 chip using standard amine based chemistry (NHS/EDC). For each Fab and IgG, different concentrations (100-1 nM) were injected over the MET ECD surface and kinetic data were collected over time. The data was fit using the simultaneous global fit equation to yield affinity constants (KD) for each Fab and IgG.

TABLE 1

Affinity of 13-MET and 28-MET Antibodies

| | nM | | |
|---|---|---|---|
| Clone | Monomer $K_D$ | Dimer $K_D$ | IgG $K_D$ |
| 13 | | 0.56 | 0.90 |
| 28 | 49.00 | 8.70 | 47.9 |

In addition, a bispecific antibody, 73R21.13, was produced using the method described in Wu et al., which is incorporated herein by reference (Wu, C., et al. Simultaneous targeting of multiple disease mediators by a dual-variable-domain immunoglobulin. Nat Biotechnol, 25: 1290-1297, 2007). The bispecific antibody comprised the light and heavy chain variable regions of both the 13-MET antibody and a 21-MET antibody (an affinity matured 28-MET antibody). The sequences of the light chain and heavy chain variable regions of the 13-MET antibody that were included in the bispecific antibody are shown in SEQ ID NO:7 and SEQ ID NO:2, respectively. The sequences of the light chain and heavy chain variable regions of the 21-MET antibody are shown in SEQ ID NO:22 and SEQ ID NO:12, respectively.

Example 2

Anti-MET Antibodies Block HGF Ligand Binding to the MET Receptor Extracellular Domain and Bind to Different Epitopes MET antibodies block hHGF binding to the MET Receptor in vitro. In certain embodiments, a HGF/MET blocking assay was used to assess HGF ligand binding to the MET Receptor. Maxi-sorp 384-well microtiter plates (Nunc, Rochester, N.Y.) were coated with recombinant human HGF (1 mg/mL×25 μL; R&D Systems, Minneapolis, Minn.) at room temperature (30° C.) for 2 hours. After washing the wells once with 0.2% PBS/T, they were blocked with 5% PBS/milk for one hour. Monomeric anti-MET antibodies (Fab), 13-MET and 28-MET, or dimeric anti-MET antibodies, 9-MET and 19-MET, were preincubated with 25 ng/well recombinant human MET/Fc chimeric protein (R&D Systems, Minneapolis, Minn.) at room temperature for 1 hour. The Fab/MET-Fc mixtures with increasing concentrations of anti-MET antibodies were then added to the HGF-coated wells and allowed to incubate for one hour at room temperature on a rocker and washed three times with 0.2% PBS/T. The secondary antibody (goat anti-human Fc, HRP-conjugated) was added at 1:5,000 dilution and allowed to incubate for one hour at room temperature. Washing was repeated as described above. Fifty microliters of substrate were added per well until a yellow color developed. The reaction was then stopped with 50 μL of 1 M $H_2SO_4$ and the absorbance at 450 nm determined with a standard plate reader.

Both 13-MET and 28-MET Fab monomeric antibodies effectively blocked binding between the MET extracellular domain and HGF (FIG. 1B, C) with an IC50 of 12.44 and 36.08, the slope of the curve (m) of 0.81443 and 0.77698, and curvefit value (r) of 0.96229 and 0.98873, respectively. Similarly, 9-MET and 19-MET dimeric Fab antibodies effectively blocked binding between MET and its ligand HGF (FIG. 2A, B) with a Dm of 5.08 and 44.34, respectively.

Epitope mapping of the MET-13 and MET-28 IgG antibodies was performed using 384-well microtiter plates coated with the human recombinant proteins MET-ECD, SEMA, and PSI-IPT. Binding of MET-13 and MET-28 IgG antibodies to individual domains of MET was determined with a standard plate reader.

The epitope analysis revealed that the 13-MET IgG antibody binds to the SEMA domain of MET-ECD and not to PSI-IPT, whereas the 28-MET IgG antibody exclusively binds to the full-length MET-ECD molecule and not to either the SEMA or PSI-IST domains in isolation. Since the SEMA domain of MET-ECD is known to be critical for HGF binding, the binding of the 13-MET antibody to the SEMA domain suggests that R13 is a direct HGF-competitor. The 28-MET antibody, on the other hand, competes with HGF but does not bind to the critical SEMA domain of MET-ECD, indicating that the 28-MET antibody recognizes an epitope in its tertiary conformation.

Example 3

Combinations of Anti-MET Antibodies Act Synergistically to Block HGF Binding to the MET Receptor Extracellular Domain and Induce ADCC on GTL-16 Cells Combinations of MET antibodies act synergistically to block hHGF binding to the MET Receptor in vitro. In certain embodiments, the HGF/MET blocking assay described in detail above was used to assess HGF ligand binding to the MET Receptor. A combination of 9-MET and 19-MET antibodies (1:5) demonstrated increased efficacy in blocking binding between HGF and MET compared to either antibody alone (FIG. 3A), with an IC50 of 4.44 compared to 8.88 for 9-MET and 105.9 for 19-MET.

MET antibodies induce Antibody-dependent Cellular Cytotoxicity (ADCC) in vitro. In certain embodiments, an ADCC assay was used to assess ADCC activity of the MET antibodies. Blood was collected from normal volunteers and mixed with 33% (v/v) volume of PBS without $Ca^{2+}$ or $Mg^{2+}$. The mixture was layered onto a Ficoll gradient and centrifuged at 400 relative centrifugal force×g for 40 min. Peripheral blood mononuclear cells were collected at the interface and washed three times in PBS. The cells were pelleted and then resuspended in RPMI 1640 medium with 10% fetal calf serum. GTL-16 cells were europium-labeled according to the manufacturer's protocol (Perkin Elmer) and plated at a density of 10,000 cells/well in 50 µl in a 96-well U-bottomed plate, and incubated with the indicated anti-MET antibodies (50 µl) at 37° C. for 30 minutes. Peripheral blood mononuclear cells were added to triplicate wells in a volume of 100 µl at an effector/tumor cell ratios of 100/1 and incubated at 37° C. for 4 hours. After centrifugation at 1500 rpm for 10 minutes, 10 µl of supernatant was transferred to a 96-well flat-bottom plate, followed by the addition of 100 µl/well europium-releasing reagent, an incubation of 15 minutes under rocking conditions and a reading of the fluorescence at 615 nm. Target maximum fluorescence was determined by lysing the cells with 10 µl of Lysis buffer, whereas target spontaneous fluorescence was determined in the absence of antibody and effector cells. The percentage of specific cell lysis mediated by the antibodies was calculated as: the percentage of cell lysis in the antibody-treated group: (experimental EM615 nm–target spontaneous)/(target maximum–target spontaneous)×100. Similarly, a combination of 13-MET and 28-MET IgG (1:5) demonstrated increased efficacy in inducing antibody-dependent cellular cytotoxicity (ADCC) on GTL-16 cells to either antibody alone (FIG. 3C), with an EC50 of 58.9 compared to 479.1 for 13-MET IgG and 3,771 for 28-MET IgG.

Figure 3A:
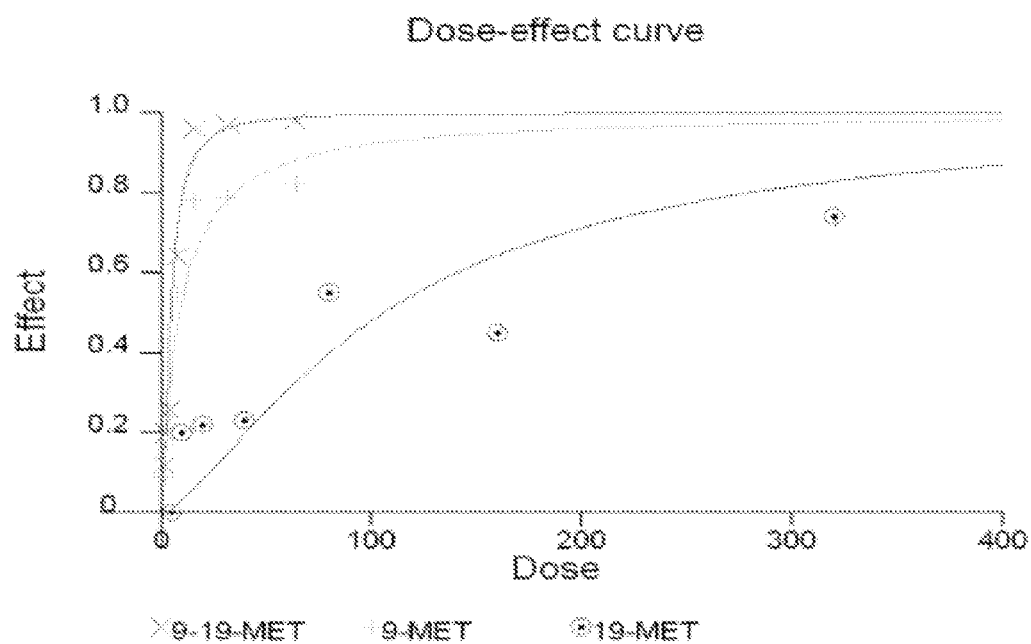
Figure 3B:
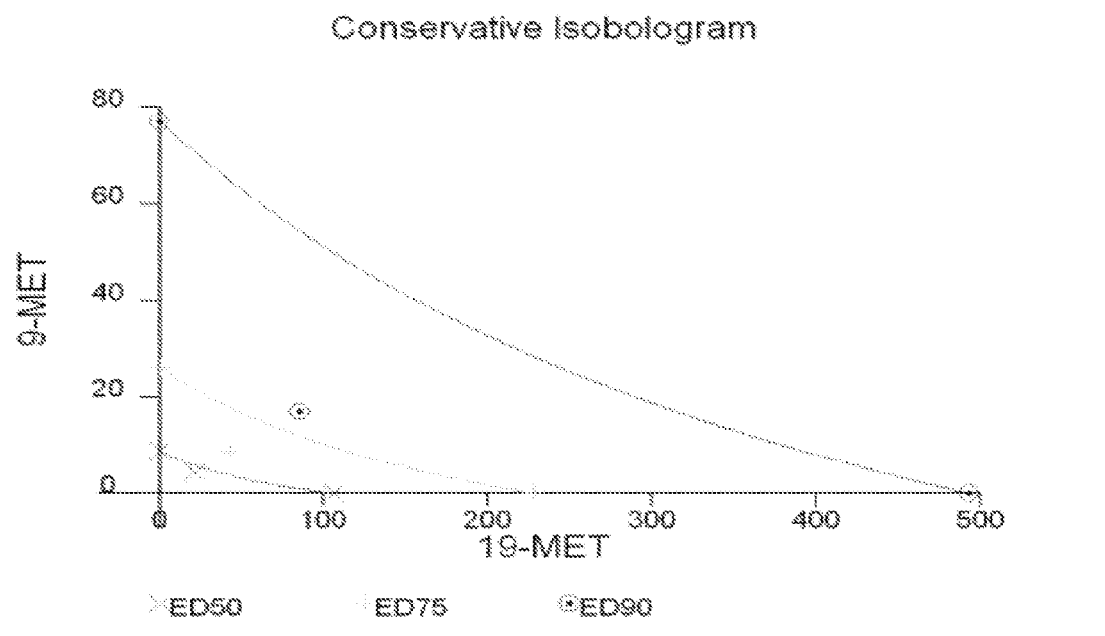
Figure 3C:
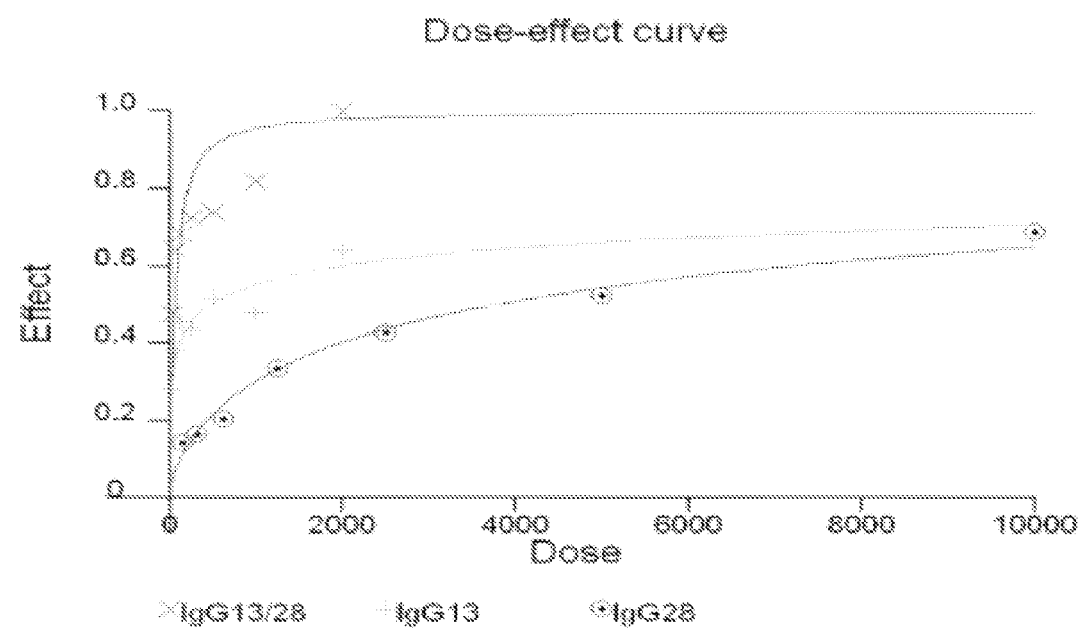
Figure 3D:
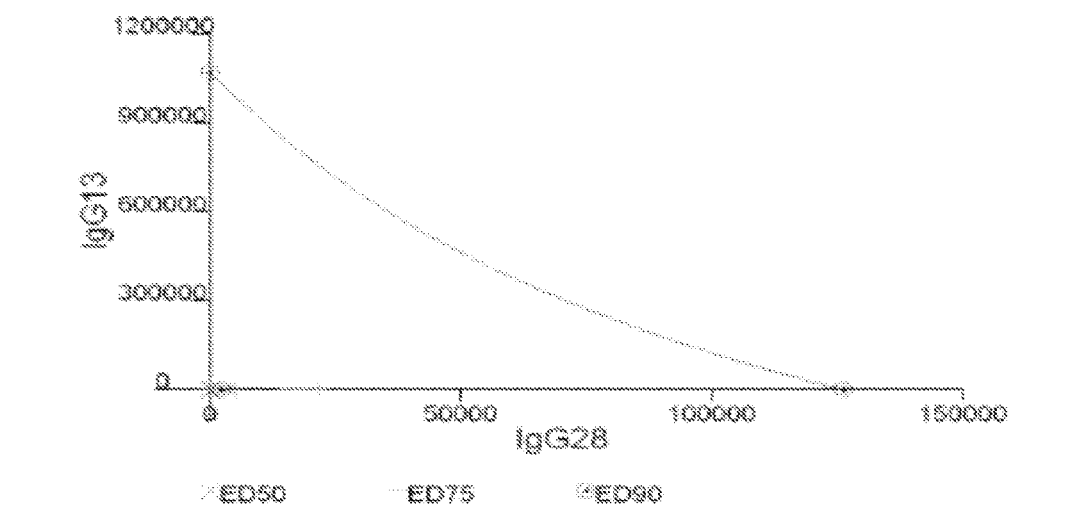

Antibody interactions were then analyzed using CalcuSyn (Chou and Hayball, 1996). This software calculates the IC50 of the antibody combinations using the median effect equation. Determination of synergy or antagonism was based on the multiple drug effect equation of Chou and Talalay (1977, 1983) and was quantified by the combination index (CI). CI=1 indicates an additive effect; <1, synergy, >1, antagonism. Results are shown for the mutually exclusive assumption of modes of activity of the drugs, however, applying the alternative assumption showed the same pattern of results (FIG. 3B, D). The CI of the 9-MET/19-MET (1:5) was 0.71 at ED50; 0.52 at ED75, and 0.40 at ED90 (FIG. 3B). The CI of 13-MET/28-MET (1:5) was 0.20 at ED50; 0.044 at ED75; and 0.018 at EC90 (FIG. 3D).

R13 was also shown to enhance R28 avidity to MET-receptor on GTL-16 cells (FIG. 3E). AF647-conjugated R28 (black bars) or R13 (white bars) were used as FACS-reagents to detect MET-receptor on GTL-16 cells. AF647-labeled antibodies (AF647-R28 or AF647-R13) were used at fixed concentrations (360 nM, AF647-R28; 20 nM, AF647-R13) and unlabeled R13 (0.5 nM, 20 nM) or R28 (90 nM, 360 nM) was titered in. Note that 20 nM of R13 increased MFI-values (ΔMFI) for AF647-R28 by 2.6 fold, whereas adding R28 to AF647-R13 did not show any effect. ΔMFI values were determined by substracting background MFI. NS indicates not stimulated. Arrows indicate the detected proteins. bars, SD.

Example 4

Combinations of Anti-MET Antibodies Eliminate Detectable HGF-Mediated MET Signaling Combinations of MET antibodies eliminated hHGF-mediated MET Receptor signaling in vivo. A549 lung tumor cells were plated onto culture plates and serum-starved (0.1% FBS in DMEM) for 24 hours. The cells were then either left untreated or were pretreated with the indicated Fab-monomers, -dimers or IgGs (30 µg/ml) for one to two hours following stimulation with 80 ng/ml recombinant human HGF for 10 min at 37° C. After HGF stimulation, the cells were lysed on ice in lysis buffer (50 mM HEPES pH 7.5, containing 150 mM NaCl, 1 mM EDTA, 10% (v/v) glycerol, 1% (v/v) Triton X-100, 1 mM sodium fluoride, 1 mM phenylmethylsulfonyl fluoride, 2 mM sodium orthovanadate, 5 mM β-glycerolphosphate, 10 mg/ml aprotinin). Crude lysates were centrifuged at 13,000 g for 20 minutes at 4° C. before protein concentrations were determined.

For immunoprecipitations, the appropriate antibody and protein A/G Sepharose (Pharmacia) were added to the cleared lysate and incubated for 3 hours at 4° C. Immunoprecipitates were washed with a washing buffer (20 mM HEPES pH 7.5, containing 150 mM NaCl, 1 mM EDTA, 1 mM sodium fluoride, 10% (v/v) glycerol, 0.1% (v/v) Triton X-100). Sample buffer containing SDS and DTT was added and the samples were denaturated by heating at 75° C. for 10 minutes. Proteins were fractionated by SDS-PAGE and electrophoretically transferred to nitrocellulose filters.

For immunoblot analysis, nitrocellulose filters were first incubated with mouse monoclonal or rabbit polyclonal primary antibodies for 3 hours at 4° C. Next, a HRP-coupled goat anti-mouse or goat anti-rabbit secondary antibody was added, followed by an enhanced chemiluminescence (ECL) substrate reaction (Amersham). The substrate reaction was detected on Kodak X-Omat film. Filters that were used more than once with different antibodies were stripped according to the manufacturer's protocol, blocked and reprobed. Antibodies raised against following proteins were used: MET (monoclonal mouse antibody (mmAb) DO-24, UBI and polyclonal rabbit antibody (prAb) C-12, Santa Cruz), phospho-MET (monoclonal rabbit antibody (mrAb) 3D7, Cell Signaling), SHC (prAb UBI), phospho-AKT (mrAb 193H12, Cell Signaling), phospho-MAPK (mrAb 197G2, Cell Signaling) and phosphotyrosine (mAb 4G10, UBI).

Figure 4A:
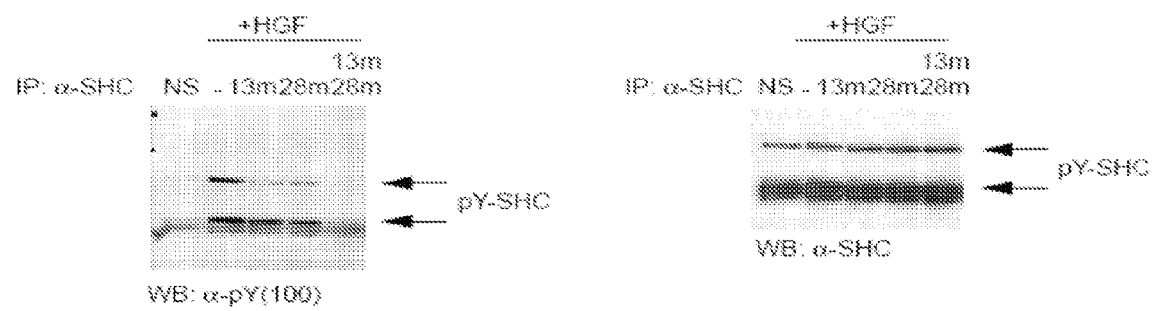

The combination of 13-28-MET monomeric antibodies eliminated detectable phosphorylation of the downstream MET signaling protein, SHC (FIG. 4A). Similarly, the combination of 9-19-MET dimeric antibodies eliminated or nearly eliminated detectable phosphorylation of the MET Receptor as well as phosphorylation of the downstream signaling molecules SHC, AKT, and ERK1/2 (FIG. 4B-D). The elimination of downstream signaling activation by anti-MET antibody combinations in lung tumor cells mimicked the block of HGF-mediated MET signaling by SU11248 (FIG. 5). Similar results were obtained using HUVEC cells (FIG. 6A-C).

Example 5

Combinations of Anti-MET Antibodies Prevent HGF-Mediated Cell Proliferation

Combinations of MET antibodies prevented hHGF-mediated cell proliferation in vitro. In certain embodiments, HUVEC cells were plated at $8\times10^4$ per ml onto Collagen I coated 96-well culture plates in complete media (serum and growth factors; EGM-2), incubated for 24 hours and subsequently serum-starved for 24 hours in EBM-2 supplemented with 5% fetal bovine serum (FBS). HUVEC cells were either left untreated or pretreated with the indicated Fab-monomers, -dimers or IgGs (30 µg/ml) for 1-2 hours and subsequently challenged with 50 ng/ml recombinant human HGF. Cells were incubated for seven days and cell number was quantified using Cell-Titer-Glo Reagent (Promega) according to the manufacturer's protocol every 48 hours.

The 9-19-MET antibody combination had no effect on cell proliferation in the absence of HGF (FIG. 6D; upper graph). In contrast, the antibody combination eliminated cell proliferation in the presence of HGF compared to control treated cells (FIG. 6D).

Example 6

Combinations of Anti-MET Antibodies Prevent HGF-Mediated Cell Migration

Combinations of MET antibodies prevented HGF-mediated cell migration in vitro. H441 cells were seeded at a density of $3\times10^5$ cells/well in a 24-well plate. HUVECs were seeded at a density of $2.5\times10^5$ cells/well in a 24-well precoated with Collagen I. The next day, cells were serum-starved for 24 hours with media containing 0.5% FCS. Then a single scrape was made in the confluent monolayer in each well as described previously (Lorenzato et al., 2002). For HGF-dependent studies, cells were pre-incubated with indicated amounts of Fab dimers for 1 hour prior to HGF addition. Photographs were taken when the gap in HGF-treated cells had closed completely 24 hours later. For HGF-independent studies, cells were treated as above without addition of HGF. The scrape was monitored and photographed.

H441 cells fail to proliferate into the scrape in the absence of HGF, but nearly completely fill in the scrape in the presence of HGF after 16 hours. Incubation with the 13-28-MET IgG combination disrupts this cell migration to a similar extent as SU11274 (FIG. 7A).

Example 7

Anti-MET Antibody Combinations Alter the Conformation of the MET Receptor

This example describes the conformational changes induced in the MET receptor by the anti-MET antibodies. Since the above-described inhibitory effects of 13-MET and 28-MET antibodies are synergistic and the antibodies do not compete for the same epitope, the ability of one antibody to decrease the flexibility of MET, thereby enabling the other antibody to block the HGF binding site was tested. The belief was that one antibody would increase the binding of the other antibody to cells expressing MET in its active form. Therefore, one unlabeled antibody (13-MET IgG ("R13") or 28-MET ("R28")) was titered to the other AF647-conjugated antibody (28-MET ('R28") or 13-MET ("R13")) and then the mean fluorescence intensity (MFI) on GTL-16 cells was measured.

More specifically, GTL-16 cells were non-enzymatically detached from cell culture plates, washed and blocked with PBS/2% FCS for 30 min prior to incubation with the antibodies. 100 µg of 13-MET IgG antibody and 28-MET IgG antibody were chemically conjugated with fluorochrome AF-647 following the supplier's protocol (Invitrogen (Carlsbad, Calif.)). Cells were then incubated with unlabeled and/or labeled 13-MET/28-MET at the concentrations indicated in FIG. 8 for 30 min at RT. After extensive washing cells were resuspended in PBS/2% FCS and analyzed by FACS.

The results are shown in FIG. 8. The ΔMFI values of AF647-conjugated 28-MET increased by increasing amounts of unlabeled 13-MET. Since the Kd values remained unchanged (data not shown), this suggests that 13-MET increases the antigen accessibility of 28-MET for MET on GTL-16 cells, which leads to an increase in ΔMFI values. Conversely, unlabeled 28-MET did not increase 13-MET-induced ΔMFI on GTL-16 cells. Taken together, this experiment indicates that 13-MET facilitates the binding of 28-MET on GTL-16 cells, thereby potentiating the binding of 28-MET to the MET extracellular domain and "locking" it into a non-functional receptor.

Example 8

In Vivo Treatment of Established Tumors Using Anti-MET Antibodies

This example describes the use of a combination of human anti-MET antibodies to treat cancer in a xenograft model. In certain embodiments, tumor cells from a patient sample (solid tumor biopsy or pleural effusion) that have been passaged as a xenograft in mice were prepared for repassaging into experimental animals. Tumor tissue was removed, cut up into small pieces, minced completely using sterile blades, and single cell suspensions obtained by enzymatic digestion and mechanical disruption. Dissociated tumor cells are then injected subcutaneously either into the mammary fat pads, for breast tumors, or were injects at 50,000 per animal into the right flank, for OMP-C12, C17, C27 and C28 colon tumors, of NOD/SCID mice to elicit tumor growth. Alternatively, ESA+, CD44+, CD24−/low, Lin-tumorigenic tumor cells are isolated as described in detail above and injected.

Figure 9A:
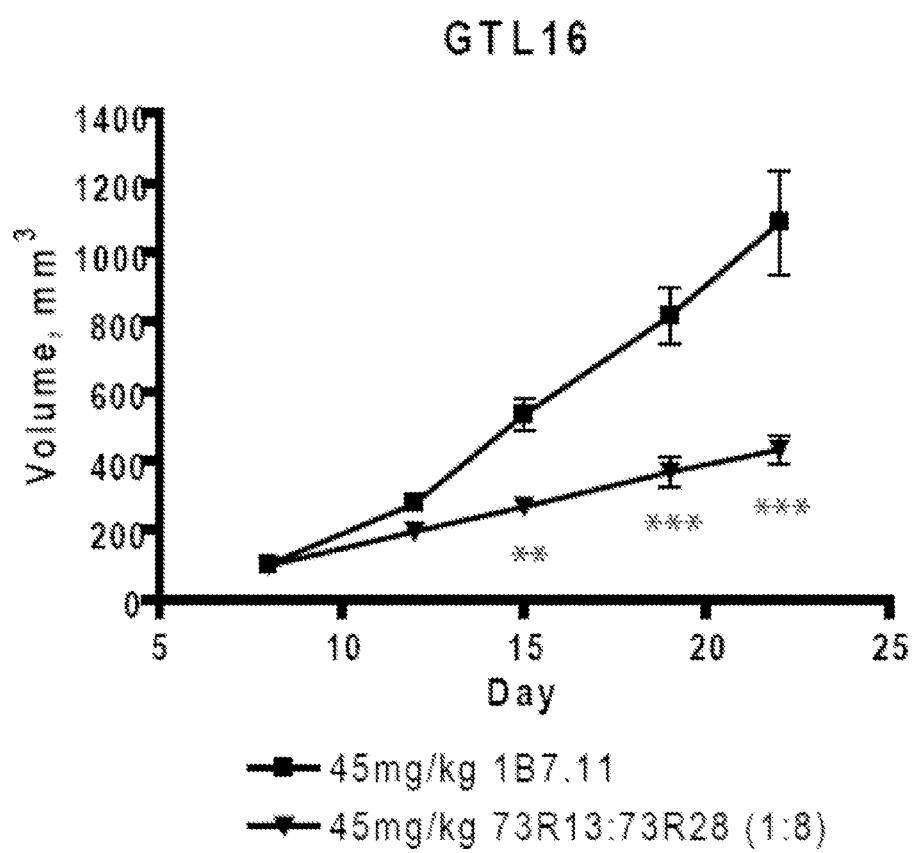
Figure 9B:
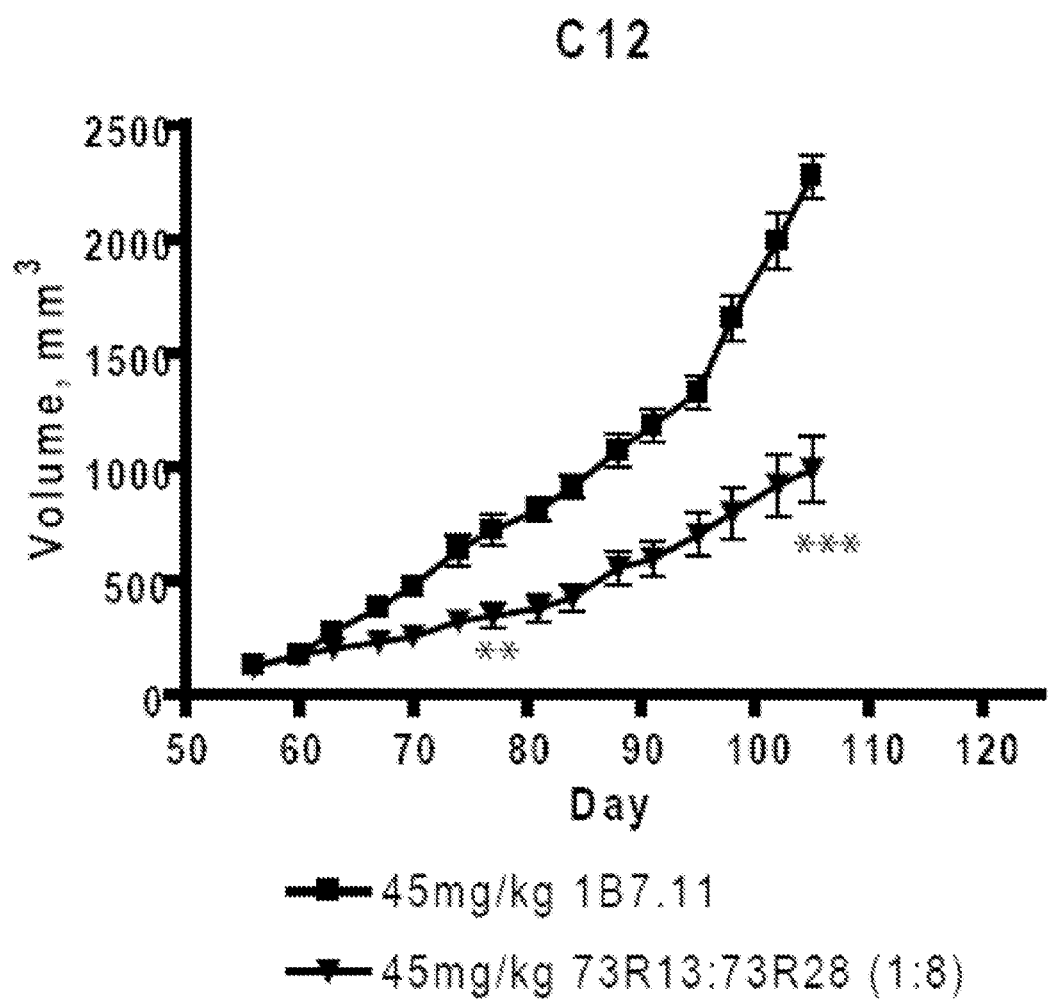
Figure 9C:
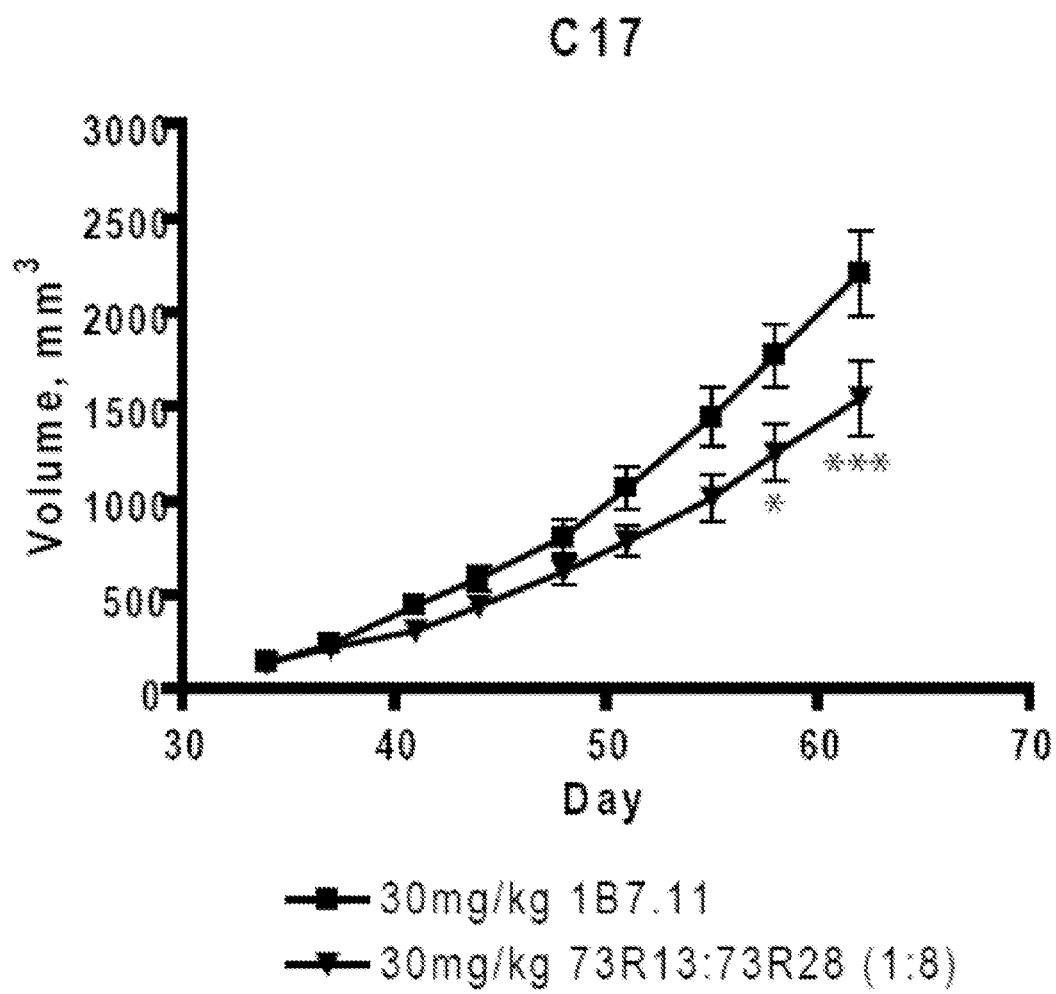
Figure 9D:
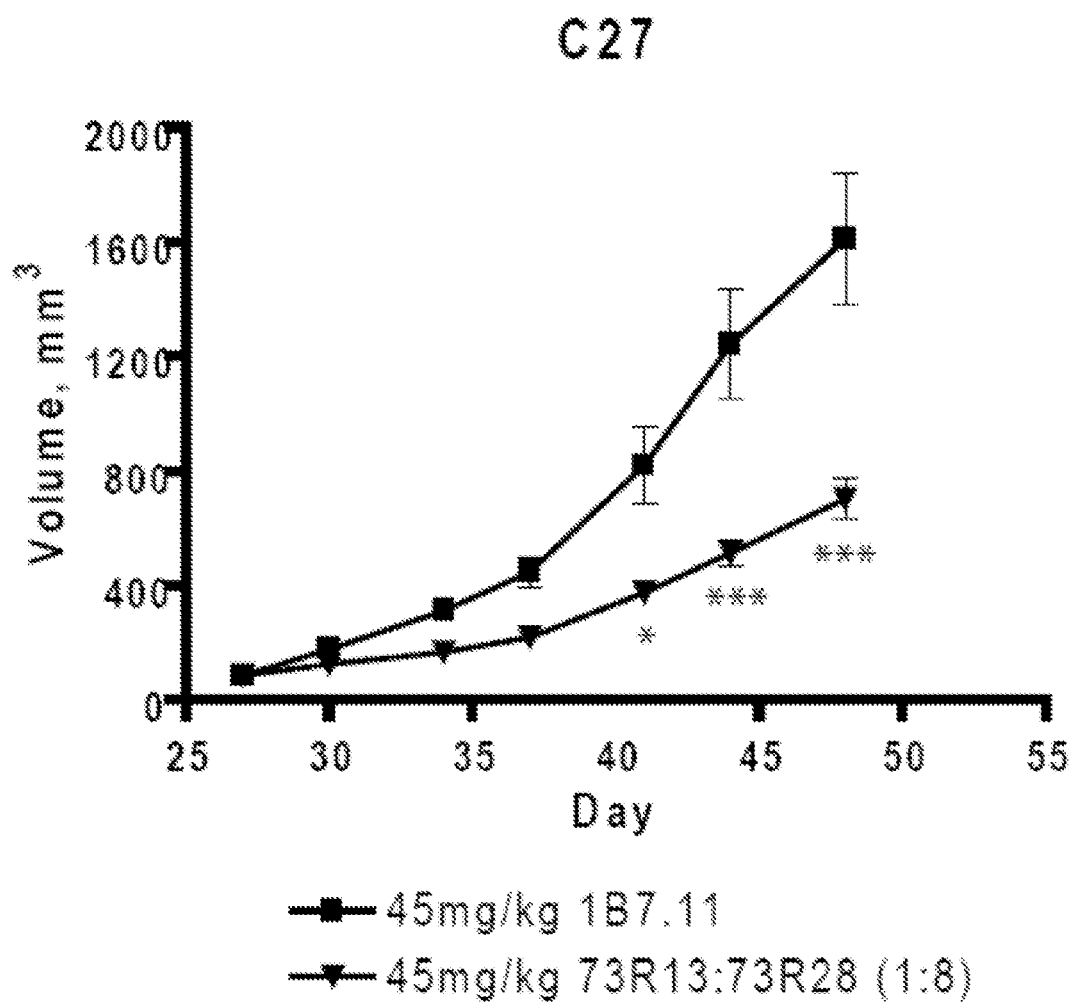

Following tumor cell injection, animals were monitored for tumor growth. Once the tumors have reached an average size of approximately 65 to 200 mm³ mice were randomized and antibody treatment began. Each animal received i.p. either 45 mg/kg (C12, C27 and C28) or 30 mg/kg (C17) of 13-MET and 28-MET antibodies at a ratio of 1:8 once a week. Tumor size was assessed twice a week. Humanized MET antibodies reduced tumor growth compared to control antibody 1B7.11 (murine IgG from ATCC) in C12, C17, C27 and C28 tumors (FIG. 9B-E). Administration of a 1:8 ratio of 13-MET to 28-MET antibodies resulted in a statistically significant decrease in C12 tumor volume compared to control antibody treated animals at day 77 post-injection (p<0.01) and day 81 to 105 (p<0.001) post-injection (FIG. 9B). Administration of a 1:8 ratio of 13-MET to 28-MET antibodies resulted in a statistically significant decrease in C17 tumor volume compared to control antibody treated animals at day 58 (p<0.01) and day 62 (p<0.001) post-injection (FIG. 9C). Administration of a 1:8 ratio of 13-MET to 28-MET antibodies resulted in a statistically significant decrease in C27 tumor volume compared to control antibody treated animals at day 41 (p<0.05) and day 44 to 48 (p<0.001) post-injection (FIG. 9D). Administration of a 1:8 ratio of 13-MET to 28-MET antibodies resulted in a statistically significant decrease in C28 tumor volume compared to control antibody treated animals at day 40 to 48 post-injection (p<0.01) (FIG. 9E).

Histologic assessment showed extensive hypoxic areas in 13-MET/28-MET(R13/28)-treatment groups when compared to control C-27-tumors. Staining for hypoxic regions was performed as reported previously (Raleigh, J. A., et al., Int J Radiat Oncol Biol Phys, 42:727-730 (1998)). Briefly, to measure hypoxia, pimonidazole-hydrochloride (HypoxyProbe, NPI, Burlington, Mass.), which forms long-lived protein adducts at partial pressure of oxygen less than approximately 10 mmHg, was injected intraperitoneally at 60 mg/kg 1 hr prior to sacrifice. Tumors were then processed for histological analysis, and tumor sections (5 μm thick) were stained using anti-pimonidazole antibody. Photographs were taken using a BX51 microscope (Olympus, Center Valley, Pa.).

Even more pronounced effects were observed the experiment was repeated with GTL-16 cells: combination of 13-MET/28-MET strongly inhibited GTL-16 tumor-growth and increased hypoxic regions almost over the entire tumor surface area, especially in the center of the tumor. Healthy cells were only detectable at the rim of the GTL-16 tumors. The data indicate that inhibition of MET signaling abrogated pro-angiogenic signals, which results in diminished tumor growth. This mechanism resembles the treatment of tumors with anti-HER2 antibody trastuzumab, which also indirectly lead to a decrease in pro-angiogenic factors, but to a dramatic increase in thrombospondin, a negative-regulator of angiogenesis (Izumi, Y., et al., Nature, 416: 279-280 (2002)).

The gene-expression profile of 13-MET/28-MET-treated C27tumors was analyzed by microarray. Global gene expression profiling analysis was performed on Affymetrix HG-U133 plus 2.0 microarray (Affymetrix, Santa Clara, Calif.). Three independent RNA samples of xenograft whole tumors from the control and treatment groups were isolated and hybridized to the microarrays according to the manufacturer's instructions. Scanned array background adjustment and signal intensity normalization were performed with GCRMA algorithm in the open-source bioconductor software (Bioconductor Project, Fred Hutchinson Cancer Research Center). Genes differentially expressed (P<0.05 and fold change>2.0) between the two groups were identified with Bayesian t-test (Baldi, P. and Long, A. D. Bioinformatics, 17: 509-519 (2001)).

TABLE 2

Gene-expression profile of 13-MET/28-MET-treated tumors

| Gene | Fold | PVal |
|---|---|---|
| LOC441453 | -2.25 | $3.10 \times 10^{-4}$ |
| KITLG | -2.43 | $1.46 \times 10^{-4}$ |
| DOK7 | -2.56 | $6.91 \times 10^{-5}$ |
| DCLK1 | -7.05 | $6.79 \times 10^{-8}$ |
| BCL11A | -3.53 | $3.07 \times 10^{-5}$ |
| ACTA1 | -2.08 | $2.32 \times 10^{-4}$ |
| PRKACB | -2.74 | $1.20 \times 10^{-4}$ |
| DHRS3 | -3.58 | $1.42 \times 10^{-5}$ |
| CRYAB | -3.17 | $2.58 \times 10^{-4}$ |
| METTL7B | -2.05 | $8.53 \times 10^{-4}$ |
| MYLPF | -3.82 | $1.61 \times 10^{-4}$ |
| C11orf31 | -2.80 | $7.30 \times 10^{-4}$ |
| CST6 | -6.56 | $1.86 \times 10^{-4}$ |
| SERPINE2 | -4.20 | $5.03 \times 10^{-4}$ |
| PCDH10 | -6.45 | $8.97 \times 10^{-4}$ |
| RAB3B | 3.53 | $8.37 \times 10^{-4}$ |
| LMO7 | 2.01 | $2.86 \times 10^{-4}$ |
| EDN1 | 2.36 | $9.81 \times 10^{-4}$ |
| KLHL24 | 2.91 | $4.75 \times 10^{-4}$ |
| LCE3D | 2.86 | $1.01 \times 10^{-4}$ |
| KLF6 | 2.29 | $5.27 \times 10^{-4}$ |
| SLC12A6 | 2.49 | $6.14 \times 10^{-4}$ |
| NOS3 | 2.42 | $3.99 \times 10^{-4}$ |
| PIK3IP1 | 2.32 | $2.69 \times 10^{-4}$ |
| HAS3 | 2.92 | $2.20 \times 10^{-4}$ |
| HAPLN3 | 2.15 | $3.65 \times 10^{-4}$ |
| SPTAN1 | 2.43 | $5.43 \times 10^{-4}$ |
| ATG9B | 3.75 | $3.02 \times 10^{-5}$ |
| HLA-F | 2.97 | $7.33 \times 10^{-5}$ |
| KRT17 | 3.17 | $7.01 \times 10^{-6}$ |
| AHNAK2 | 2.03 | $1.47 \times 10^{-5}$ |
| MGC3260 | 2.36 | $5.15 \times 10^{-4}$ |
| ARHGAP29 | 2.21 | $1.61 \times 10^{-4}$ |
| MAP3K8 | 3.40 | $4.19 \times 10^{-5}$ |
| TncRNA | 3.74 | $1.32 \times 10^{-5}$ |
| IL6R | 3.03 | $8.30 \times 10^{-5}$ |
| MEF2A | 2.30 | $3.60 \times 10^{-4}$ |
| MAST4 | 2.77 | $1.96 \times 10^{-4}$ |
| CEACAM1 | 2.14 | $3.20 \times 10^{-4}$ |
| TGFA | 2.02 | $2.90 \times 10^{-4}$ |
| ECM1 | 2.49 | $1.06 \times 10^{-4}$ |
| BMP2 | 2.76 | $2.40 \times 10^{-4}$ |
| DUSP5 | 3.86 | $8.29 \times 10^{-7}$ |
| PRDM1 | 2.47 | $8.60 \times 10^{-7}$ |
| FRMD4A | 2.42 | $5.51 \times 10^{-5}$ |
| LOC162993 | 3.66 | $5.02 \times 10^{-6}$ |
| HSD11B1 | 48.85 | $8.88 \times 10^{-16}$ |

Interestingly, inhibition of HGF/MET pathway significantly up-regulated the known tumor-suppressors KLF6, CEACAM1 and BMP2 (2.3-fold, 2.1-fold and 2.8-fold, P<0.001) and the negative-regulator of Phosphatidyl-inositol-3-OH-kinase (PI3K) PIK3IP1 (2.3-fold, P<0.001). Concurrently, SCF and SERPINE2, both enhancers of proliferation and invasiveness, were significantly suppressed (SCF, 2.4-fold, SERPINE2, 4.2-fold, P<0.001). It has previously been shown, that the tumor suppressor functions of KLF6, CEACAM1 and BMP2 are inactivated in CRC (Miyaki, M., et al., Oncology 71:131-135 (2006); Mukai, S. et al., World J Gastroenterol 13:3932-3938 (2007); Shively, J. E. Oncogene 23:9303-9305 (2004)). Moreover, SCF/KIT-receptor signaling has been implicated in proliferation and invasiveness of CRC through the PI3K/AKT pathway (Yasuda, A. et al., Dig Dis Sci, 52:2292-2300 (2007)). A recent report by Zhu et al. suggests that PIK3IP1 is a novel p110 interacting protein, which directly down modulates PI3K-activity (Biochem Biophys Res Commun, 358:66-72 (2007)). On the other hand, SERPINE2 has been involved in enhancing invasive potential of pancreas cancer cells in nude mice (Buchholz, M. et al., Cancer Res, 63:4945-4951 (2003)). One mode of action of 13-MET/28-MET could be the restoration of the tumor suppressor function of KLF6, CEACAM1 and BMP2, which ultimately would inhibit tumor progression. Additionally, 13-MET/28-MET-induced PIK3IP1 could amplify the inhibition of AKT1 phosphorylation and also potentiate 13-MET/28-MET-induced down-regulation of SCF via abrogated PI3K-activity, resulting in diminished anti-apoptotic/migratory signaling.

In certain embodiments, combinations of anti-MET antibodies are administered. In certain embodiments, a combination of 13-MET and 28-MET human IgG antibodies are administered. In certain embodiments, a combination of 9-MET and 19-MET dimeric Fab antibodies are administered. In certain embodiments, the 13-MET and 28-MET antibodies are administered at a ratio of 1:5. In certain embodiments, the 9-MET and 19-MET antibodies are administered at a ratio of 1:5.

Figure 9F:
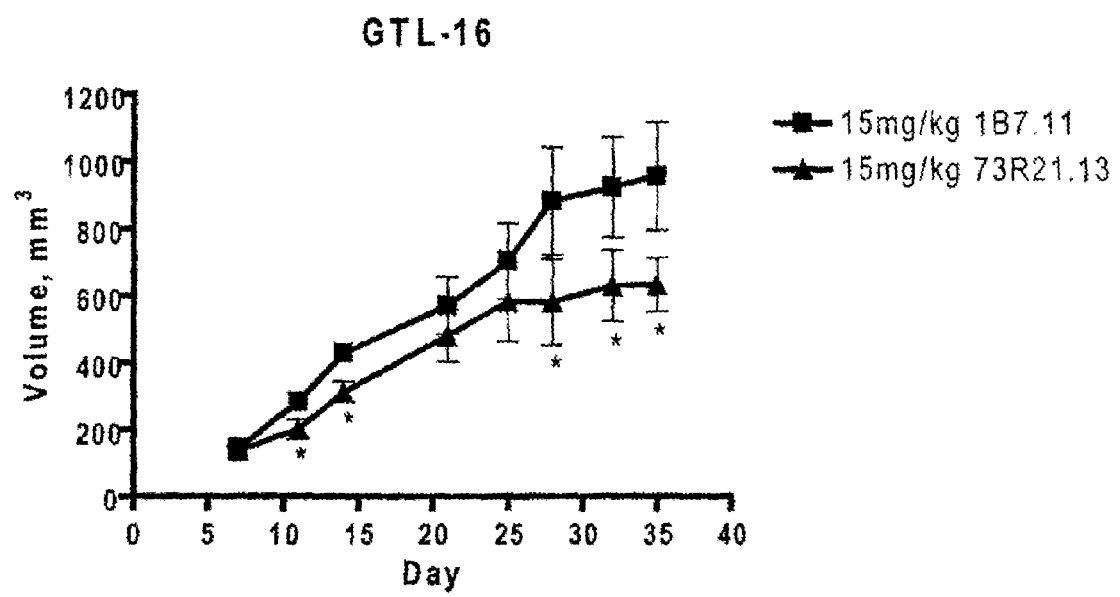

In certain embodiments, $1 \times 10^7$ GTL-16 tumor cells were injected subcutaneously into the right posterior flanks of 6-8 week-old immunodeficient nu –/– female mice on a Swiss CD-1 background (Harlan). The injected total volume per mouse was 200 µl with 50% being Matrigel (BD Biosciences). Once the tumors have reached an average size of approximately 65 to 200 mm$^3$ mice were randomized and antibody treatment began with either 13-MET and 28-MET antibodies administered weekly at a ratio of 1:8 at 45 mg/kg (FIG. 9A), or at 15 mg/kg of the 13-21 MET bispecific antibody 73R21.13 (FIG. 9F). Tumor volume was measured twice weekly as described in Michieli et al., Cancer Cell 2004 July; 6(1):61-73. All the experiments were performed on groups of at least ten animals per experimental point. Administration of a 1:8 ratio of 13-MET to 28-MET antibodies resulted in a statistically significant decrease in tumor volume compared to control antibody treated animals at day 15 post-injection ($p<0.01$) and at day 19 ($p<0.001$) (FIG. 9A). Administration of the bispecific 13-21 MET antibody 73R21.13 also resulted in a statistically significant decrease in tumor volume compared to control antibody treated animals (FIG. 9F).

At the end point of antibody treatment, tumors are harvested for further analysis. In some embodiments, a portion of the tumor is analyzed by immunofluorescence to assess antibody penetration into the tumor and tumor response. A portion of each harvested tumor from anti-MET treated and control antibody treated mice is fresh-frozen in liquid nitrogen, embedded in O.C.T., and cut on a cryostat as 10 µm sections onto glass slides. In some embodiments, a portion of each tumor is formalin-fixed, paraffin-embedded, and cut on a microtome as 10 µm section onto glass slides. Sections are post-fixed and incubated with chromophore labeled antibodies that specifically recognize injected antibodies to detect anti-MET receptor or control antibodies present in the tumor biopsy. Furthermore antibodies that detect different tumor and tumor-recruited cell types such as, for example, anti-VE cadherin (CD144) or anti-PECAM-1 (CD31) antibodies to detect vascular endothelial cells, anti-smooth muscle alpha-actin antibodies to detect vascular smooth muscle cells, anti-Ki67 antibodies to detect proliferating cells, TUNEL assays to detect dying cells, anti-intracellular domain (ICD) Notch fragment antibodies to detect Notch signaling can be used to assess the effects of antibody treatment on, for example, angiogenesis, tumor growth and tumor morphology.

In certain embodiments, the effect of humanized anti-MET antibody treatment on tumor cell gene expression is also assessed. Total RNA is extracted from a portion of each harvested tumor from MET antibody treated and control antibody treated mice and used for quantitative RT-PCR. Expression levels of the MET receptor, MET ligands, components of the MET signaling pathway, as well as addition cancer stem cell markers previously identified (e.g. CD44) are analyzed relative to the house-keeping gene GAPDH as an internal control. Changes in tumor cell gene expression upon MET antibody treatment are thus determined.

In addition, the effect of humanized anti-MET receptor antibody treatment on the presence of cancer stem cells in a tumor is assessed. Tumor samples from MET versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24–/low, Lin-surface cell marker expression as described in detail above.

The tumorigenicity of cells isolated based on ESA+, CD44+, CD24–/low, Lin-expression following humanized anti-MET antibody treatment can then assessed. ESA+, CD44+, CD24–/low, Lin-cancer stem cells isolated from MET antibody treated versus control antibody treated mice are re-injected subcutaneously into the mammary fat pads of NOD/SCID mice. The tumorigenicity of cancer stem cells based on the number of injected cells required for consistent tumor formation is then determined.

Example 9

Decrease in Lung Metastases Using Anti-MET Antibodies

This example describes the use of a combination of human anti-MET antibodies to increase survival by decreasing lung metastases in vivo. It has previously been reported that inhibition of MET in GTL-16 strongly decreased lung metastases in vivo (Corso, S. et al. Oncogene, 27: 684-693, 2008). Therefore, the ability of 13-MET and 28-MET to increase survival by diminishing lung metastases in an experimental metastasis model with GTL-16 cells was tested. Experimental metastasis-assays were performed as described previously (Corso, S. et al.) with the exception that GTL-16-luc were used, and tumor burden in mice was visualized by non-invasive imaging with an IVIS200 instrument (Caliper, Mountain View, Calif.), as previously published (Zhang, G. J. et al., Neoplasia 9:652-661 (2007)). Antibodies were administered weekly or as indicated and tumors measured twice weekly. Tumor volume was calculated as described in Al-Hajj et al. (Proc Natl Acad Sci USA 100:3983-3988 (2003)). All the experiments were performed on groups of at least ten animals per experimental point.

Mice were injected with GTL-16 cells stably expressing the luciferase (luc)-gene and treated weekly with 13-MET/28-MET (R13/28) antibodies or control antibody 1B7.11. Treatment was stopped after three weeks and the disease recurrence was measured by non-invasive imaging every week. After 70 days five out of seven mice were alive, and 4 out of five showed strong luc-activity in the lungs, whereas 13-MET/28-MET-treated animals were all alive and did not show any luc-activity (data not shown). At day 170, only one mouse in the 13-MET/28-MET-treatment group had died, whereas in the control group six out of seven mice had died (FIG. 10). This suggests that the antibody-treatment with 13-MET/28-MET antibodies inhibited either the extravasation of the tumor cells and/or diminished the survival capabilities of GTL-16 in the lungs, by preventing the binding of stromal-derived HGF to MET. Another explanation is that 13-MET or 28-MET act as inverse agonists, thereby shifting the equilibrium from the activated state towards the inactive form of MET. This shift could then lead to decrease of proliferation and increase of the apoptotic rate of GTL-16 cells.

Example 10

Treatment of Human Cancer Using Anti-MET Antibodies

This example describes methods for treating cancer using human antibodies against MET to target tumors comprising cancer stem cells. The presence of cancer stem cell marker expression can first be determined from a tumor biopsy. Tumor cells from a biopsy from a patient diagnosed with cancer are removed under sterile conditions. In some embodiments the tissue biopsy is fresh-frozen in liquid nitrogen, embedded in O.C.T., and cut on a cryostat as 10 μm sections onto glass slides. In some embodiments, the tissue biopsy is formalin-fixed, paraffin-embedded, and cut on a microtome as 10 μm section onto glass slides. In some embodiments, sections are incubated with antibodies against MET to detect protein expression.

The presence of cancer stem cells can also be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, and -Lin antibodies to detect cancer stem cells, and the presence of ESA+, CD44+, CD24−/low, and Lin-tumor stem cells is determined by flow cytometry as described in detail above.

Cancer patients are treated with human anti-MET antibodies. In certain embodiments, anti-MET antibodies generated as described above are purified and formulated with a suitable pharmaceutical vehicle for injection. In certain embodiments, combinations of anti-MET antibodies are administered. In certain embodiments, a combination of 13-MET and 28-MET human IgG antibodies are administered. In certain embodiments, a combination of 9-MET and 19-MET dimeric Fab antibodies are administered. In certain embodiments, the 13-MET and 28-MET antibodies are administered at a ratio of 1:5. In certain embodiments, the 9-MET and 19-MET antibodies are administered at a ratio of 1:5. In certain embodiments bispecific antibodies comprising the antigen determination region of 13-MET and 28-MET are administered.

In certain embodiments, patients are treated with the antibodies at least once a month for at least ten weeks. In certain embodiments, patients are treated with the antibodies at least once a week for at least about fourteen weeks. Each administration of the antibody should be a pharmaceutically effective dose. In some embodiments, between about 2 to about 100 mg/ml of an antibody is administered. In some embodiments, between about 5 to about 40 mg/ml of a humanized antibody is administered. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response based on, for example, tumor regression, reduction in the incidences of new tumors, lower tumor antigen expression, decreased numbers of cancer stem cells, or other means of evaluating disease prognosis.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications and patents mentioned in the above specification are herein incorporated by reference in their entirety.

What is claimed is:

1. An isolated antibody that specifically binds human MET, the antibody selected from the group consisting of:
   (a) an antibody comprising (i) a heavy chain CDR1 comprising GFSLSTSGMVVS (SEQ ID NO:3), a heavy chain CDR2 comprising FISWDDDKYYSTSLKT (SEQ ID NO:4), and a heavy chain CDR3 comprising EPGRYGGYYFDY (SEQ ID NO:5); and (ii) a light chain CDR1 comprising RASQTISHYLA (SEQ ID NO:8), a light chain CDR2 comprising AASILQS (SEQ ID NO:9), and a light chain CDR3 comprising QQYSGFPV (SEQ ID NO:10);
   (b) an antibody comprising (i) a heavy chain CDR1 comprising GGSISGYYWS (SEQ ID NO:13), a heavy chain CDR2 comprising EIYYAGSTLYNPSLKG (SEQ ID NO:14), and a heavy chain CDR3 comprising HYGLDWFGDTGMDV (SEQ ID NO:15); and (ii) a light chain CDR1 comprising SGDNLGDKYVH (SEQ ID NO:18), a light chain CDR2 comprising DDNERPSG (SEQ ID NO:19), and a light chain CDR3 comprising SAYGSHSGT (SEQ ID NO:20); and
   (c) an antibody comprising (i) a heavy chain CDR1 comprising GGSISGYYWS (SEQ ID NO:13), a heavy chain CDR2 comprising EIYYAGSTLYNPSLKG (SEQ ID NO:14), and a heavy chain CDR3 comprising HYGLDWFGDTGMDV (SEQ ID NO:15); and (ii) a light chain CDR1 comprising SGDNLGEQYVH (SEQ ID NO:23), a light chain CDR2 comprising DDSERPSG (SEQ ID NO:24), and a light chain CDR3 comprising QSYTFYPNSR (SEQ ID NO:25).

2. The isolated antibody of claim 1, wherein the antibody comprises:
   (a) a heavy chain variable region having at least 95% identity to SEQ ID NO:2 and a light chain variable region having at least 95% identity to SEQ ID NO:7;
   (b) a heavy chain variable region having at least 95% identity to SEQ ID NO:12 and a light chain variable region having at least 95% identity to SEQ ID NO:17; or
   (c) a heavy chain variable region having at least 95% identity to SEQ NO:12 and a light chain variable region having at, least 95% identity to SEQ ID NO:22.

3. The isolated antibody of claim 1, which is a recombinant antibody, a monoclonal antibody, a chimeric antibody, a bispecific antibody, a humanized antibody, a human antibody, or an antibody fragment.

4. The isolated antibody of claim 1, which inhibits human growth factor (HGF) binding to human MET.

5. An isolated monoclonal antibody that binds to the same epitope on human MET as the antibody of claim 1.

6. A pharmaceutical composition comprising an antibody of claim 1 and a pharmaceutically acceptable excipient.

7. A method of treating cancer in a subject, comprising administering to the subject a therapeutically effective amount of an antibody of claim 1.

8. A method of treating cancer in a subject, comprising administering to the subject a therapeutically effective amount of ar antibody that specifically binds human MET, wherein the antibody binds to the same epitope on human MET as the antibody of claim 1.

9. A method of treating cancer in a subject, comprising administering to the subject a therapeutically effective amount of a combination of antibodies, wherein at least one of the antibodies is an antibody of claim 1 which specifically binds human MET.

10. A bispecific antibody comprising:
    (a) a first arm that specifically binds a first epitope on human MET comprising an antibody selected from the group consisting of:

(i) an antibody comprising (1) a heavy chain CDR1 comprising GFSLSTSGMVVS (SEQ ID NO:3), a heavy chain CDR2 comprising FISWDDDKYYSTSLKT (SEQ ID NO:4), and a heavy chain CDR3 comprising EPGRYGGYYFDY (SEQ ID NO:5); and (2) a light chain CDR1 comprising RASQTISHYLA (SEQ ID NO:8), a light chain CDR2 comprising AASILQS (SEQ ID NO:9), and a light chain CDR3 comprising QQYSGFPV (SEQ ID NO:10);

(ii) an antibody comprising (1) a heavy chain CDR1 comprising GGSISGYYWS (SEQ ID NO:13), a heavy chain CDR2 comprising EIYYAGSTLYNPSLKG (SEQ ID NO:14), and a heavy chain CDR3 comprising HYGLDWFGDTGMDV (SEQ ID NO:15); and (2) a light chain CDR1 comprising SGDNLGDKYVH (SEQ ID NO:18), a light chain CDR2 comprising DDNERPSG (SEQ ID NO:19), and a light chain CDR3 comprising SAYGSHSGT (SEQ ID NO:20); and (iii) an antibody comprising (1) a heavy chain CDR1 comprising GGSISGYYWS (SEQ ID NO:13), a heavy chain CDR2 comprising EIYYAGSTLYNPSLKG (SEQ ID NO:14), and a heavy chain CDR3 comprising HYGLDWFGDTGMDV (SEQ ID NO:15); and (2) a light chain CDR1 comprising SGDNLGEQYVH (SEQ ID NO:23), a light chain CDR2 comprising DDSERPSG (SEQ ID NO:24), and a light chain CDR3 comprising QSYTFYPNSR (SEQ ID NO:25); and (b) a second arm that specifically binds a second, different epitope.

11. The bispecific antibody of claim 10, wherein the first arm specifically binds an epitope in the SEMA domain of human MET.

12. The bispecific antibody of claim 10, wherein the second arm specifically binds a second epitope on a different receptor.

13. The bispecific antibody of claim 10, wherein the second aim specifically binds a second epitope on human MET.

14. The bispecific antibody of claim 10, which is a recombinant antibody, a monoclonal antibody, a chimeric antibody, a humanized antibody, a human antibody, or an antibody fragment.

15. The bispecific antibody of claim 10, which inhibits human growth factor (HGF) binding to human MET.

16. An isolated monoclonal antibody that binds to the same epitope on human MET as the first arm of the bispecific antibody of claim 10.

17. A pharmaceutical composition comprising a bispecific antibody of claim 10 and a pharmaceutically acceptable excipient.

18. A method of treating cancer in a subject, comprising administering to the subject a therapeutically effective amount of a bispecific antibody of claim 10.

19. A method of treating cancer in a subject, comprising administering to the subject a therapeutically effective amount of an antibody that specifically binds human MET, wherein the antibody binds to the same epitope or human MET as the first arm of the bispecific antibody of claim 10.

20. A method of treating cancer in a subject, comprising administering to the subject a therapeutically effective amount of at least one isolated antibody that specifically binds human MET, wherein the at least one isolated antibody is selected from the group consisting of:

(a) an antibody comprising (i) a heavy chain CDR1 comprising GFSLSTSGMVVS (SEQ ID NO:3), a heavy chain CDR2 comprising FISWDDDKYYSTSLKT (SEQ ID NO:4), and a heavy chain CDR3 comprising EPGRYGGYYFDY (SEQ ID NO:5); and (ii) a light chain CDR1 comprising RASQTISHYLA (SEQ ID NO:8), a light chain CDR2 comprising AASILQS (SEQ ID NO:9), and a light chain CDR3comprising QQYSGFPV (SEQ ID NO:10);

(b) an antibody comprising (i) a heavy chain CDR1 comprising GGSISGYYWS (SEQ ID NO:13), a heavy chain CDR2 comprising EIYYAGSTLYNPSLKG (SEQ ID NO:14), and a heavy chain CDR3 comprising HYGLDWFGDTGMDV (SEQ ID NO:15); and (ii) a light chain CDR1 comprising SGDNLGDKYVH (SEQ ID NO:18), a light chain CDR2 comprising DDNERPSG (SEQ ID NO:19), and a light chain CDR3 comprising SAYGSHSGT (SEQ ID NO:20); and (c) an antibody comprising (i) a heavy chain CDR1 comprising GGSISGYYWS (SEQ ID NO:13), a heavy chain CDR2 comprising EIYYAGSTUYJNIPSLKG (SEQ ID NO:14), and a heavy chain CDR3 comprising HYGLDWFGDTGMDV (SEQ ID NO:15); and (ii) a light chain CDR1 comprising SGDNLGEQYVH (SEQ ID NO:23), a light chair CDR2 comprising DDSERPSG (SEQ ID NO:24), and a light chain CDR3 comprising QSYTFYPNSR (SEQ ID NO:25).

\* \* \* \* \*

SEQUENCE LISTING

```
<160> NUMBER OF SEQ ID NOS: 29

<210> SEQ ID NO 1
<211> LENGTH: 366
<212> TYPE: DNA
<213> ORGANISM: Artificial Sequence
<220> FEATURE:
<223> OTHER INFORMATION: Synthetic Fab-13 VH nucleotide sequence

<400> SEQUENCE: 1
caggtgcaat tgaaagaaag cggcccggcc ctggtgaaac cgacccaaac cctgaccctg      60
acctgtacct tttccggatt tagcctgtct acttctggta tggttgtgtc ttggattcgc     120
cagccgcctg ggaaagccct cgagtggctg gcttttatct cttgggatga tgataagtat     180
tatagcacca gcctgaaaac gcgtctgacc attagcaaag atacttcgaa aaatcaggtg     240
gtgctgacta tgaccaacat ggacccggtg gatacggcca cctattattg cgcgcgtgag     300
cctggtcgtt atggtggtta ttattttgat tattggggcc aaggcaccct ggtgacggtt     360
agctca                                                                366

<210> SEQ ID NO 2
<211> LENGTH: 122
<212> TYPE: PRT
<213> ORGANISM: Artificial Sequence
<220> FEATURE:
```

<223> OTHER INFORMATION: Synthetic Fab-13 VH protein sequence

<400> SEQUENCE: 2

```
Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Val Val Ser Trp Ile Arg Gln Pro Pro Gly Lys Ala Leu Glu
        35                  40                  45

Trp Leu Ala Phe Ile Ser Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Glu Pro Gly Arg Tyr Gly Gly Tyr Tyr Phe Asp Tyr Trp
            100                 105                 110

Gly Gln Gly Thr Leu Val Thr Val Ser Ser
        115                 120
```

<210> SEQ ID NO 3
<211> LENGTH: 12
<212> TYPE: PRT
<213> ORGANISM: Artificial Sequence
<220> FEATURE:
<223> OTHER INFORMATION: Synthetic Fab-13 VH CDR1

<400> SEQUENCE: 3

```
Gly Phe Ser Leu Ser Thr Ser Gly Met Val Val Ser
1               5                   10
```

<210> SEQ ID NO 4
<211> LENGTH: 16
<212> TYPE: PRT
<213> ORGANISM: Artificial Sequence
<220> FEATURE:
<223> OTHER INFORMATION: Synthetic Fab-13 VH CDR2

<400> SEQUENCE: 4

```
Phe Ile Ser Trp Asp Asp Asp Lys Tyr Tyr Ser Thr Ser Leu Lys Thr
1               5                   10                  15
```

<210> SEQ ID NO 5
<211> LENGTH: 12
<212> TYPE: PRT
<213> ORGANISM: Artificial Sequence
<220> FEATURE:
<223> OTHER INFORMATION: Synthetic Fab-13 VH CDR3

<400> SEQUENCE: 5

```
Glu Pro Gly Arg Tyr Gly Gly Tyr Tyr Phe Asp Tyr
1               5                   10
```

<210> SEQ ID NO 6
<211> LENGTH: 327
<212> TYPE: DNA
<213> ORGANISM: Artificial Sequence
<220> FEATURE:
<223> OTHER INFORMATION: Synthetic Fab-13 VL nucleotide sequence

<400> SEQUENCE: 6

```
gatatccaga tgacccagag cccgtctagc ctgagcgcga gcgtgggtga tcgtgtgacc      60
attacctgca gagcgagcca gactattcct cattatctgg cttggtacca gcagaaacca     120
```

```
ggtaaagcac cgaaactatt aatttatgct gcttctattt tgcaaagcgg ggtcccgtcc      180
cgttttagcg gctctggatc cggcactgat tttaccctga ccattagcag cctgcaacct      240
gaagactttg cggttttatta ttgccagcag tattctggtt ttcctgttac ctttggccag      300
ggtacgaaag ttgaaattaa acgtacg                                          327
```

```
<210> SEQ ID NO 7
<211> LENGTH: 109
<212> TYPE: PRT
<213> ORGANISM: Artificial Sequence
<220> FEATURE:
<223> OTHER INFORMATION: Synthetic Fab-13 VL protein sequence

<400> SEQUENCE: 7
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser His Tyr
            20                  25                  30

Leu Ala Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Gly Phe Pro Val
                85                  90                  95

Thr Phe Gly Gln Gly Thr Lys Val Glu Ile Lys Arg Thr
            100                 105

```
<210> SEQ ID NO 8
<211> LENGTH: 11
<212> TYPE: PRT
<213> ORGANISM: Artificial Sequence
<220> FEATURE:
<223> OTHER INFORMATION: Synthetic Fab-13 VL CDR1

<400> SEQUENCE: 8
```

Arg Ala Ser Gln Thr Ile Ser His Tyr Leu Ala
1               5                   10

```
<210> SEQ ID NO 9
<211> LENGTH: 7
<212> TYPE: PRT
<213> ORGANISM: Artificial Sequence
<220> FEATURE:
<223> OTHER INFORMATION: Synthetic Fab-13 VL CDR2

<400> SEQUENCE: 9
```

Ala Ala Ser Ile Leu Gln Ser
1               5

```
<210> SEQ ID NO 10
<211> LENGTH: 8
<212> TYPE: PRT
<213> ORGANISM: Artificial Sequence
<220> FEATURE:
<223> OTHER INFORMATION: Synthetic Fab-13 VL CDR3

<400> SEQUENCE: 10
```

Gln Gln Tyr Ser Gly Phe Pro Val
1               5

```
<210> SEQ ID NO 11
<211> LENGTH: 366
<212> TYPE: DNA
<213> ORGANISM: Artificial Sequence
<220> FEATURE:
<223> OTHER INFORMATION: Synthetic Fab-28 VH nucleotide sequence

<400> SEQUENCE: 11
caggtgcaat tgcaagaaag tggtccgggc ctggtgaaac cgggcgaaac cctgagcctg      60
acctgcaccg tttccggagg cagcatttct ggttattatt ggtcttggat tcgccaggcc     120
cctgggaagg gtctcgagtg gattggcgag atctattatg ctggctctac ccttataat     180 ccgagcctga aaggccgggt gaccattagc gttgatactt cgaaaaacca gtttagcctg     240
aaactgagca gcgtgacggc ggaagatacg gccgtgtatt attgcgcgcg tcattatggt     300
cttgattggt ttggtgatac tggtatggat gtttggggcc aaggcaccct ggtgacggtt     360
agctca                                                                 366

<210> SEQ ID NO 12
<211> LENGTH: 122
<212> TYPE: PRT
<213> ORGANISM: Artificial Sequence
<220> FEATURE:
<223> OTHER INFORMATION: Synthetic Fab-28 VH protein sequence

<400> SEQUENCE: 12

Gln Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Ala Pro Gly Lys Gly Leu Glu Trp Ile
        35                  40                  45

Gly Glu Ile Tyr Tyr Ala Gly Ser Thr Leu Tyr Asn Pro Ser Leu Lys
    50                  55                  60

Gly Arg Val Thr Ile Ser Val Asp Thr Ser Lys Asn Gln Phe Ser Leu
65                  70                  75                  80

Lys Leu Ser Ser Val Thr Ala Glu Asp Thr Ala Val Tyr Tyr Cys Ala
                85                  90                  95

Arg His Tyr Gly Leu Asp Trp Phe Gly Asp Thr Gly Met Asp Val Trp
            100                 105                 110

Gly Gln Gly Thr Leu Val Thr Val Ser Ser
        115                 120

<210> SEQ ID NO 13
<211> LENGTH: 10
<212> TYPE: PRT
<213> ORGANISM: Artificial Sequence
<220> FEATURE:
<223> OTHER INFORMATION: Synthetic Fab-28 VH CDR1

<400> SEQUENCE: 13

Gly Gly Ser Ile Ser Gly Tyr Tyr Trp Ser
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic Fab-28 VH CDR2

<400> SEQUENCE: 14
```

```
Glu Ile Tyr Tyr Ala Gly Ser Thr Leu Tyr Asn Pro Ser Leu Lys Gly
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: Synthetic Fab-28 VH CDR3

<400> SEQUENCE: 15

His Tyr Gly Leu Asp Trp Phe Gly Asp Thr Gly Met Asp Val
1               5                   10

<210> SEQ ID NO 16
<211> LENGTH: 324
<212> TYPE: DNA
<213> ORGANISM: Artificial Sequence
<220> FEATURE:
<223> OTHER INFORMATION: Synthetic Fab-28 VL nucleotide sequence

<400> SEQUENCE: 16
gatatcgaac tgacccagcc gccttcagtg agcgttgcac caggtcagag cattaccatc        60
tcgtgtagcg gcgataatct tggtgataag tatgttcatt ggtaccagca gaaacccggg       120
caggcgccag ttcttgtgat ttatgatgat aatgagcgtc cctcaggcat cccggaacgc       180
tttagcggat ccaacagcgg caacaccgcg accctgacca ttagcggcac tcaggcggaa       240
gacgaagcgg attattattg ctctgcttat ggttctcatt ctggtactgt gtttggcggc       300
ggcacgaagt taaccgttct tggc                                              324

<210> SEQ ID NO 17
<211> LENGTH: 108
<212> TYPE: PRT
<213> ORGANISM: Artificial Sequence
<220> FEATURE:
<223> OTHER INFORMATION: Synthetic Fab-28 VL protein sequence

<400> SEQUENCE: 17

Asp Ile Glu Leu Thr Gln Pro Pro Ser Val Ser Val Ala Pro Gly Gln
1               5                   10                  15

Ser Ile Thr Ile Ser Cys Ser Gly Asp Asn Leu Gly Asp Lys Tyr Val
            20                  25                  30

His Trp Tyr Gln Gln Lys Pro Gly Gln Ala Pro Val Leu Val Ile Tyr
        35                  40                  45

Asp Asp Asn Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ala Tyr Gly Ser His Ser Gly Thr
                85                  90                  95

Val Phe Gly Gly Gly Thr Lys Leu Thr Val Leu Gly
            100                 105

<210> SEQ ID NO 18
<211> LENGTH: 11
<212> TYPE: PRT
<213> ORGANISM: Artificial Sequence
<220> FEATURE:
<223> OTHER INFORMATION: Synthetic Fab-28 VL CDR1

<400> SEQUENCE: 18

Ser Gly Asp Asn Leu Gly Asp Lys Tyr Val His
```

<210> SEQ ID NO 19
<211> LENGTH: 8
<212> TYPE: PRT
<213> ORGANISM: Artificial Sequence
<220> FEATURE:
<223> OTHER INFORMATION: Synthetic Fab-28 VL CDR2

<400> SEQUENCE: 19

Asp Asp Asn Glu Arg Pro Ser Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Fab-28 VL CDR3

<400> SEQUENCE: 20

Ser Ala Tyr Gly Ser His Ser Gly Thr
1               5

<210> SEQ ID NO 21
<211> LENGTH: 327
<212> TYPE: DNA
<213> ORGANISM: Artificial Sequence
<220> FEATURE:
<223> OTHER INFORMATION: Synthetic Fab-21 VL nucleotide sequence

<400> SEQUENCE: 21
gatatcgaac tgacccagcc gccttcagtg agcgttgcac caggtcagac cgcgcgtatc       60
tcgtgtagcg gcgataatct tggtgagcag tatgttcatt ggtaccagca gaaacccggg      120
caggcgccag ttcttgtgat ttatgatgat tctgagcgtc cctcaggcat cccggaacgc      180
tttagcggat ccaacagcgg caacaccgcg accctgacca ttagcggcac tcaggcggaa      240
gacgaagcgg attattattg ccagtcttat acttttttatc ctaattctcg tgtgtttggc      300
ggcggcacga agttaaccgt tcttggc                                           327

<210> SEQ ID NO 22
<211> LENGTH: 109
<212> TYPE: PRT
<213> ORGANISM: Artificial Sequence
<220> FEATURE:
<223> OTHER INFORMATION: Synthetic Fab-21 VL protein sequence

<400> SEQUENCE: 22

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Glu Gln Tyr Val
            20                  25                  30

His Trp Tyr Gln Gln Lys Pro Gly Gln Ala Pro Val Leu Val Ile Tyr
        35                  40                  45

Asp Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Thr Phe Tyr Pro Asn Ser
                85                  90                  95

Arg Val Phe Gly Gly Gly Thr Lys Leu Thr Val Leu Gly
            100                 105

<210> SEQ ID NO 23
<211> LENGTH: 11
<212> TYPE: PRT
<213> ORGANISM: Artificial Sequence
<220> FEATURE:
<223> OTHER INFORMATION: Synthetic Fab-21 VL CDR1

<400> SEQUENCE: 23

Ser Gly Asp Asn Leu Gly Glu Gln Tyr Val His
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Synthetic Fab-21 VL CDR2

<400> SEQUENCE: 24

Asp Asp Ser Glu Arg Pro Ser Gly
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Fab-21 VL CDR3

<400> SEQUENCE: 25

Gln Ser Tyr Thr Phe Tyr Pro Asn Ser Arg
1               5                   10

<210> SEQ ID NO 26
<211> LENGTH: 4173
<212> TYPE: DNA
<213> ORGANISM: Homo sapiens

<400> SEQUENCE: 26

```
atgaaggccc cgctgtgct tgcacctggc atcctcgtgc tcctgtttac cttggtgcag      60
aggagcaatg ggagtgtaa agaggcacta gcaaagtccg agatgaatgt gaatatgaag     120
tatcagcttc caacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg gaacacccag attgtttccc atgtcaggac     300
tgcagcagca agccaatttt atcaggaggt gtttggaaag ataacatcaa catggctcta     360
gttgtcgaca cctactatga tgatcaactc attagctgtg cagcgtcaa cagagggacc     420
tgccagcgac atgtctttcc ccacaatcat actgctgaca tacagtcgga ggttcactgc     480
atattctccc cacagataga agagcccagc cagtgtcctg actgtgtggt gagcgccctg     540
ggagccaaag tcctttcatc tgtaaaggac cggttcatca acttctttgt aggcaatacc     600
ataaattctt cttatttccc agatcatcca ttgcattcga tatcagtgag aaggctaaag     660
gaaacgaaag atggttttat gttttttgacg gaccagtcct acattgatgt tttacctgag     720
ttcagagatt cttaccccat taagtatgtc catgcctttg aaagcaacaa ttttatttac     780
ttcttgacgg tccaaaggga aactctagat gctcagactt tcacacaag aataatcagg     840
ttctgttcca taaactctgg attgcattcc tacatggaaa tgcctctgga gtgtattctc     900
acagaaaaga gaaaaaagag atccacaaag aaggaagtgt taatatact tcaggctgcg     960
```

```
tatgtcagca agcctggggc ccagcttgct agacaaatag gagccagcct gaatgatgac    1020
attcttttcg gggtgttcgc acaaagcaag ccagattctg ccgaaccaat ggatcgatct    1080
gccatgtgtg cattccctat caaatatgtc aacgacttct tcaacaagat cgtcaacaaa    1140
aacaatgtga gatgtctcca gcattttttac ggacccaatc atgagcactg ctttaatagg    1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga cttggattt cggaggaata taaatttga tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatcttta ttagtggtgg agcacaata    2280 acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actgaaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttgacaat    3300 gatggcaaga aaattcactg tgctgtgaaa tccttgaaca gaatcactga cataggagaa    3360
```

```
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacacctt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140 acacgaccag cctccttctg ggagacatca tag                                 4173

<210> SEQ ID NO 27
<211> LENGTH: 1390
<212> TYPE: PRT
<213> ORGANISM: Homo sapiens

<400> SEQUENCE: 27

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240
```

```
Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
```

-continued

```
                660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
            690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Gly Gly Ser Thr Ile Thr Gly Val Gly Lys Asn Leu Asn
                755                 760                 765
Ser Val Ser Val Pro Arg Met Val Ile Asn Val His Glu Ala Gly Arg
770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
                820                 825                 830
Leu Ile Tyr Val His Asn Pro Val Phe Lys Pro Phe Glu Lys Pro Val
                835                 840                 845
Met Ile Ser Met Gly Asn Glu Asn Val Leu Glu Ile Lys Gly Asn Asp
            850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
                900                 905                 910
Gln Ala Ile Ser Ser Thr Val Leu Gly Lys Val Ile Val Gln Pro Asp
                915                 920                 925
Gln Asn Phe Thr Gly Leu Ile Ala Gly Val Val Ser Ile Ser Thr Ala
            930                 935                 940
Leu Leu Leu Leu Leu Gly Phe Phe Leu Trp Leu Lys Lys Arg Lys Gln
945                 950                 955                 960
Ile Lys Asp Leu Gly Ser Glu Leu Val Arg Tyr Asp Ala Arg Val His
                965                 970                 975
Thr Pro His Leu Asp Arg Leu Val Ser Ala Arg Ser Val Ser Pro Thr
                980                 985                 990
Thr Glu Met Val Ser Asn Glu Ser  Val Asp Tyr Arg Ala  Thr Phe Pro
            995                 1000                1005
Glu Asp Gln Phe Pro Asn Ser  Ser Gln Asn Gly Ser  Cys Arg Gln
            1010                1015                1020
Val Gln Tyr Pro Leu Thr Asp Met Ser Pro Ile Leu  Thr Ser Gly
            1025                1030                1035
Asp Ser  Asp Ile Ser Ser Pro  Leu Leu Gln Asn Thr  Val His Ile
            1040                1045                1050
Asp Leu  Ser Ala Leu Asn Pro  Glu Leu Val Gln Ala  Val Gln His
            1055                1060                1065
Val Val  Ile Gly Pro Ser Ser  Leu Ile Val His Phe  Asn Glu Val
            1070                1075                1080
```

```
Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 28
<211> LENGTH: 1390
<212> TYPE: PRT
<213> ORGANISM: Homo sapiens

<400> SEQUENCE: 28

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
        35                  40                  45
```

-continued

```
Glu Thr Pro Ile Gln Asn Val Ile Leu His Glu His His Ile Phe Leu
 50                  55                  60
Gly Ala Thr Asn Tyr Ile Tyr Val Leu Asn Glu Asp Leu Gln Lys
 65                  70                  75                  80
Val Ala Glu Tyr Lys Thr Gly Pro Val Leu Glu His Pro Asp Cys Phe
                     85                  90                  95
Pro Cys Gln Asp Cys Ser Ser Lys Ala Asn Leu Ser Gly Gly Val Trp
                100                 105                 110
Lys Asp Asn Ile Asn Met Ala Leu Val Val Asp Thr Tyr Tyr Asp Asp
                115                 120                 125
Gln Leu Ile Ser Cys Gly Ser Val Asn Arg Gly Thr Cys Gln Arg His
    130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                165                 170                 175
Val Ser Ala Leu Gly Ala Lys Val Leu Ser Ser Val Lys Asp Arg Phe
                180                 185                 190
Ile Asn Phe Phe Val Gly Asn Thr Ile Asn Ser Ser Tyr Phe Pro Asp
                195                 200                 205
His Pro Leu His Ser Ile Ser Val Arg Arg Leu Lys Glu Thr Lys Asp
    210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
                260                 265                 270
Thr Phe His Thr Arg Ile Ile Arg Phe Cys Ser Ile Asn Ser Gly Leu
    275                 280                 285
His Ser Tyr Met Glu Met Pro Leu Glu Cys Ile Leu Thr Glu Lys Arg
    290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
    355                 360                 365
Tyr Val Asn Asp Phe Phe Asn Lys Ile Val Asn Lys Asn Asn Val Arg
    370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
    435                 440                 445
Asp Leu Thr Ile Ala Asn Leu Gly Thr Ser Glu Gly Arg Phe Met Gln
    450                 455                 460
Val Val Val Ser Arg Ser Gly Pro Ser Thr Pro His Val Asn Phe Leu
465                 470                 475                 480
```

```
Leu Asp Ser His Pro Val Ser Pro Glu Val Ile Val Glu His Thr Leu
            485                 490                 495
Asn Gln Asn Gly Tyr Thr Leu Val Ile Thr Gly Lys Lys Ile Thr Lys
        500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
            565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
            595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
            645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
        675                 680                 685
His Ile Ser Ile Gly Gly Lys Thr Cys Thr Leu Lys Ser Val Ser Asn
        690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
            725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu Asn
        755                 760                 765
Ser Val Ser Val Pro Arg Met Val Ile Asn Val His Glu Ala Gly Arg
770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
            805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
            835                 840                 845
Met Ile Ser Met Gly Asn Glu Asn Val Leu Glu Ile Lys Gly Asn Asp
850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
            885                 890                 895
Pro Asn Asp Leu Leu Lys Leu Asn Ser Glu Leu Asn Ile Glu Trp Lys
```

```
                    900                 905                 910
Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
        930                 935                 940

Leu Leu Leu Leu Leu Gly Phe Phe Leu Trp Leu Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                 1005

Glu Asp Gln Phe Pro Asn Ser  Ser Gln Asn Gly Ser  Cys Arg Gln
    1010                1015                1020

Val Gln Tyr Pro Leu Thr Asp Met Ser Pro Ile Leu  Thr Ser Gly
    1025                1030                1035

Asp Ser Asp Ile Ser Ser Pro  Leu Leu Gln Asn Thr  Val His Ile
    1040                1045                1050

Asp Leu Ser Ala Leu Asn Pro  Glu Leu Val Gln Ala  Val Gln His
    1055                1060                1065

Val Val Ile Gly Pro Ser Ser  Leu Ile Val His Phe  Asn Glu Val
    1070                1075                1080

Ile Gly Arg Gly His Phe Gly  Cys Val Tyr His Gly  Thr Leu Leu
    1085                1090                1095

Asp Asn Asp Gly Lys Lys Ile  His Cys Ala Val Lys  Ser Leu Asn
    1100                1105                1110

Arg Ile Thr Asp Ile Gly Glu  Val Ser Gln Phe Leu  Thr Glu Gly
    1115                1120                1125

Ile Ile Met Lys Asp Phe Ser  His Pro Asn Val Leu  Ser Leu Leu
    1130                1135                1140

Gly Ile Cys Leu Arg Ser Glu  Gly Ser Pro Leu Val  Val Leu Pro
    1145                1150                1155

Tyr Met Lys His Gly Asp Leu  Arg Asn Phe Ile Arg  Asn Glu Thr
    1160                1165                1170

His Asn Pro Thr Val Lys Asp  Leu Ile Gly Phe Gly  Leu Gln Val
    1175                1180                1185

Ala Lys Gly Met Lys Tyr Leu  Ala Ser Lys Lys Phe  Val His Arg
    1190                1195                1200

Asp Leu Ala Ala Arg Asn Cys  Met Leu Asp Glu Lys  Phe Thr Val
    1205                1210                1215

Lys Val Ala Asp Phe Gly Leu  Ala Arg Asp Met Tyr  Asp Lys Glu
    1220                1225                1230

Tyr Tyr Ser Val His Asn Lys  Thr Gly Ala Lys Leu  Pro Val Lys
    1235                1240                1245

Trp Met Ala Leu Glu Ser Leu  Gln Thr Gln Lys Phe  Thr Thr Lys
    1250                1255                1260

Ser Asp Val Trp Ser Phe Gly  Val Val Leu Trp Glu  Leu Met Thr
    1265                1270                1275

Arg Gly Ala Pro Pro Tyr Pro  Asp Val Asn Thr Phe  Asp Ile Thr
    1280                1285                1290

Val Tyr Leu Leu Gln Gly Arg  Arg Leu Leu Gln Pro  Glu Tyr Cys
    1295                1300                1305
```

-continued

Pro Asp Pro Leu Tyr Glu Val Met Leu Lys Cys Trp His Pro Lys
1310                1315                    1320

Ala Glu Met Arg Pro Ser Phe Ser Glu Leu Val Ser Arg Ile Ser
1325                1330                    1335

Ala Ile Phe Ser Thr Phe Ile Gly Glu His Tyr Val His Val Asn
1340                1345                    1350

Ala Thr Tyr Val Asn Val Lys Cys Val Ala Pro Tyr Pro Ser Leu
1355                1360                    1365

Leu Ser Ser Glu Asp Asn Ala Asp Asp Glu Val Asp Thr Arg Pro
1370                1375                    1380

Ala Ser Phe Trp Glu Thr Ser
1385                1390

<210> SEQ ID NO 29
<211> LENGTH: 908
<212> TYPE: PRT
<213> ORGANISM: Homo sapiens

<400> SEQUENCE: 29

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
                20                  25                  30

Leu His Glu His His Ile Phe Leu Gly Ala Thr Asn Tyr Ile Tyr Val
            35                  40                  45

Leu Asn Glu Glu Asp Leu Gln Lys Val Ala Glu Tyr Lys Thr Gly Pro
        50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

```
Val Phe Asn Ile Leu Gln Ala Ala Tyr Val Ser Lys Pro Gly Ala Gln
290                 295                 300
Leu Ala Arg Gln Ile Gly Ala Ser Leu Asn Asp Ile Leu Phe Gly
305                 310                 315                 320
Val Phe Ala Gln Ser Lys Pro Asp Ser Ala Glu Pro Met Asp Arg Ser
                325                 330                 335
Ala Met Cys Ala Phe Pro Ile Lys Tyr Val Asn Asp Phe Phe Asn Lys
            340                 345                 350
Ile Val Asn Lys Asn Asn Val Arg Cys Leu Gln His Phe Tyr Gly Pro
        355                 360                 365
Asn His Glu His Cys Phe Asn Arg Thr Leu Leu Arg Asn Ser Ser Gly
370                 375                 380
Cys Glu Ala Arg Arg Asp Glu Tyr Arg Thr Glu Phe Thr Thr Ala Leu
385                 390                 395                 400
Gln Arg Val Asp Leu Phe Met Gly Gln Phe Ser Glu Val Leu Leu Thr
                405                 410                 415
Ser Ile Ser Thr Phe Ile Lys Gly Asp Leu Thr Ile Ala Asn Leu Gly
            420                 425                 430
Thr Ser Glu Gly Arg Phe Met Gln Val Val Ser Arg Ser Gly Pro
        435                 440                 445
Ser Thr Pro His Val Asn Phe Leu Leu Asp Ser His Pro Val Ser Pro
450                 455                 460
Glu Val Ile Val Glu His Thr Leu Asn Gln Asn Gly Tyr Thr Leu Val
465                 470                 475                 480
Ile Thr Gly Lys Lys Ile Thr Lys Ile Pro Leu Asn Gly Leu Gly Cys
                485                 490                 495
Arg His Phe Gln Ser Cys Ser Gln Cys Leu Ser Ala Pro Pro Phe Val
            500                 505                 510
Gln Cys Gly Trp Cys His Asp Lys Cys Val Arg Ser Glu Glu Cys Leu
        515                 520                 525
Ser Gly Thr Trp Thr Gln Gln Ile Cys Leu Pro Ala Ile Tyr Lys Val
530                 535                 540
Phe Pro Asn Ser Ala Pro Leu Glu Gly Gly Thr Arg Leu Thr Ile Cys
545                 550                 555                 560
Gly Trp Asp Phe Gly Phe Arg Arg Asn Asn Lys Phe Asp Leu Lys Lys
                565                 570                 575
Thr Arg Val Leu Leu Gly Asn Glu Ser Cys Thr Leu Thr Leu Ser Glu
            580                 585                 590
Ser Thr Met Asn Thr Leu Lys Cys Thr Val Gly Pro Ala Met Asn Lys
        595                 600                 605
His Phe Asn Met Ser Ile Ile Ile Ser Asn Gly His Gly Thr Thr Gln
610                 615                 620
Tyr Ser Thr Phe Ser Tyr Val Asp Pro Val Ile Thr Ser Ile Ser Pro
625                 630                 635                 640
Lys Tyr Gly Pro Met Ala Gly Gly Thr Leu Leu Thr Leu Thr Gly Asn
                645                 650                 655
Tyr Leu Asn Ser Gly Asn Ser Arg His Ile Ser Ile Gly Gly Lys Thr
            660                 665                 670
Cys Thr Leu Lys Ser Val Ser Asn Ser Ile Leu Glu Cys Tyr Thr Pro
        675                 680                 685
Ala Gln Thr Ile Ser Thr Glu Phe Ala Val Lys Leu Lys Ile Asp Leu
690                 695                 700
Ala Asn Arg Glu Thr Ser Ile Phe Ser Tyr Arg Glu Asp Pro Ile Val
705                 710                 715                 720
```

-continued

```
Tyr Glu Ile His Pro Thr Lys Ser Phe Ile Ser Gly Gly Ser Thr Ile
            725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
    770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
        850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr
            900                 905
```